(12) United States Patent
Kim et al.

(10) Patent No.: US 8,729,276 B2
(45) Date of Patent: May 20, 2014

(54) CYANINE COMPOUND FOR LABELING BIOMOLECULE AND PREPARATION METHOD THEREOF

(75) Inventors: Dong Jin Kim, Gyeonggi-do (KR); Young Soo Kim, Gyeonggi-do (KR); Jong Joo Na, Seoul (KR); Jin Woo Park, Incheon (KR); Ki Won Kim, Incheon (KR)

(73) Assignees: Korea Institute of Science and Technology, Seoul (KR); DKC Corporation, Incheon (KR)

( * ) Notice: Subject to any disclaimer, the term of this patent is extended or adjusted under 35 U.S.C. 154(b) by 86 days.

(21) Appl. No.: 13/264,258

(22) PCT Filed: Apr. 2, 2010

(86) PCT No.: PCT/KR2010/002046
§ 371 (c)(1),
(2), (4) Date: Dec. 29, 2011

(87) PCT Pub. No.: WO2010/120058
PCT Pub. Date: Oct. 21, 2010

(65) Prior Publication Data
US 2012/0095187 A1 Apr. 19, 2012

(30) Foreign Application Priority Data
Apr. 17, 2009 (KR) .......................... 10-2009-0033867

(51) Int. Cl.
*C07D 209/02* (2006.01)
(52) U.S. Cl.
USPC ........................................................ 548/455
(58) Field of Classification Search
None
See application file for complete search history.

(56) References Cited

U.S. PATENT DOCUMENTS

| | | | |
|---|---|---|---|
| 5,268,486 A | 12/1993 | Waggoner et al. | |
| 6,002,003 A | 12/1999 | Shen et al. | |
| 6,043,205 A | 3/2000 | Hoshiko et al. | |
| 6,127,134 A | 10/2000 | Minden et al. | |
| 2004/0023408 A1 | 2/2004 | Cotton | |

FOREIGN PATENT DOCUMENTS

WO WO 96/33406 A1 10/1996
WO WO 2004/005933 A1 1/2004

OTHER PUBLICATIONS

Ernest, L. A. et al., *Cyanine Dye Labeling Reagents for Sulfhydryl Groups*, Cytometry 10, (1989), 3-10.
Gruber, H. J. et al., Bioconjugate Chem., vol. 11, pp. 161-166 (2000).
Mujumdar, R. B. et al., *Cyanine Dye Labeling Reagents Containing Isothiocyanate Groups*, Cytometry 10, (1989), 11-19
Mujumdar, R. B. et al., *Cyanine Dye Labeling Reagents: Sulfoindocyanine Succinimidyl Esters*, Bioconjugate Chem. 4, (1993), 105-111.
Mjumdar, S. R. et al., *Cyanine-Labeling Reagents: Sulfobenzindocyanine Succinimidyl Esters*, Bioconjugate Chem. 7, (1996), 356-362.
Southwick, P. L. et al., *Cyanine Dye Labeling Reagents— Carboxymethylindocyanine Succinimidyl Esters*, Cytometry 11, (1990), 418-430.
International Search Report for Application No. PCT/KR2010/002046 dated Jan. 31, 2011.

*Primary Examiner* — Nyeemah A Grazier
(74) *Attorney, Agent, or Firm* — Alston & Bird LLP

(57) ABSTRACT

Disclosed are a novel cyanine compound, represented by the following Formula 1, for labeling biomolecules, and a method for preparing the same.

(1)

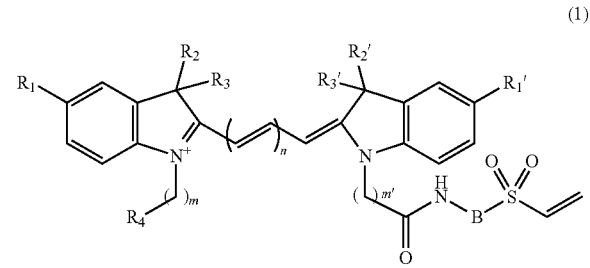

wherein $R_1$, $R_2$, $R_3$, $R_4$, B, m and n are defined as above.

11 Claims, 13 Drawing Sheets
(5 of 13 Drawing Sheet(s) Filed in Color)

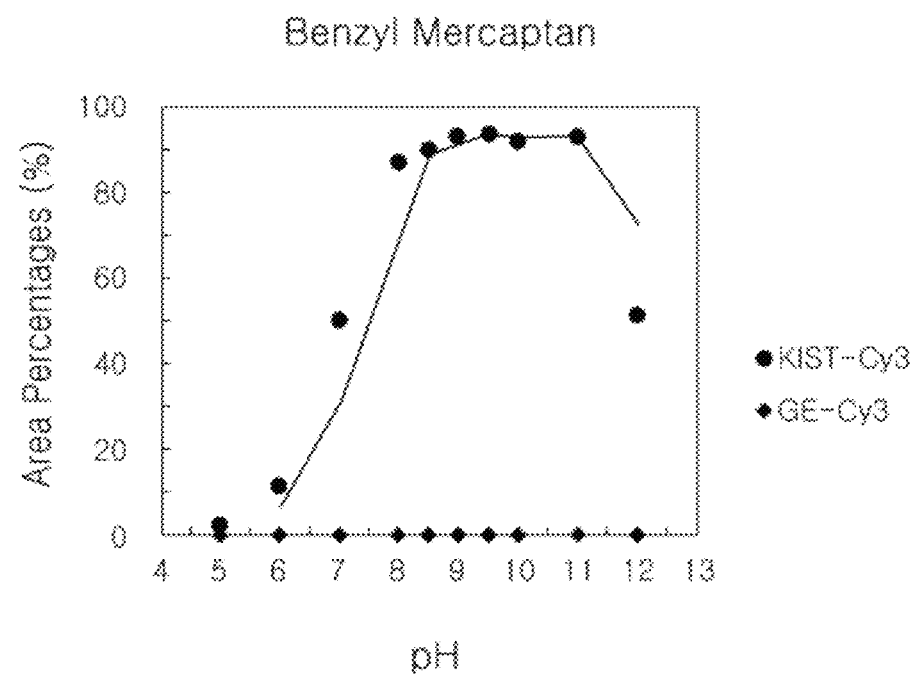

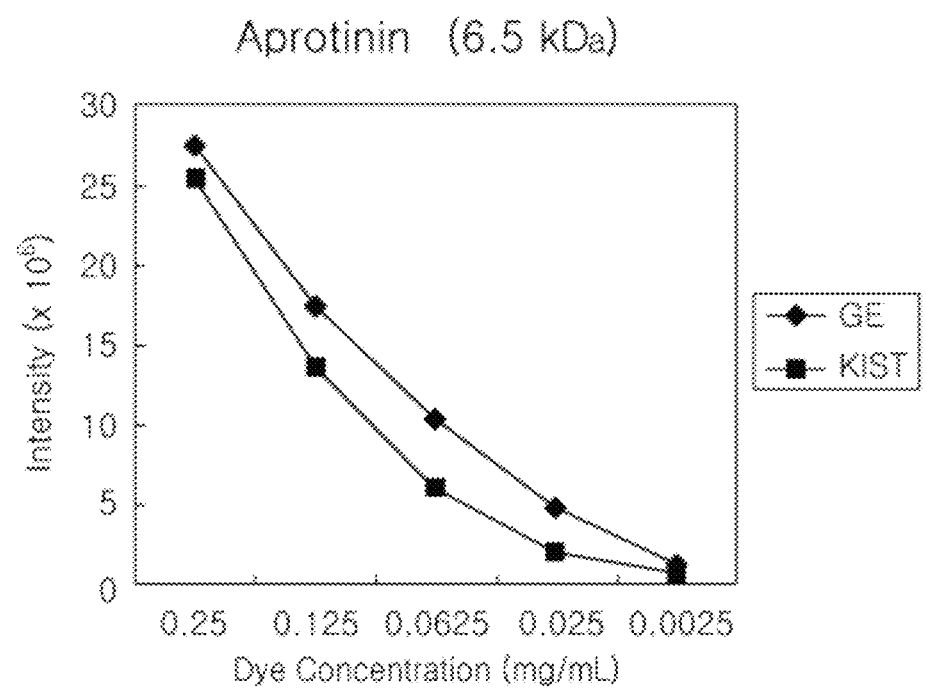

CYANINE COMPOUND FOR LABELING BIOMOLECULE AND PREPARATION METHOD THEREOF

CROSS REFERENCE TO RELATED APPLICATIONS

This application is a national stage application filed under 35 U.S.C. 371 of International Application No. PCT/KR2010/002046, filed Apr. 2, 2010, which claims priority from Korean Application No. 10-2009-0033867, filed Apr. 17, 2009, each of which is incorporated herein in its entirety.

BACKGROUND OF THE INVENTION

1. Field of the Invention

The present invention relates to a novel cyanine compound for fluorescently labeling various biomolecules and a method for preparing the same.

2. Description of the Related Art

Substitution groups in proteins that can be bound to reactive groups in dyes can be inferred from the structure of amino acids (basic units of proteins). For example, amino acid residues, more specifically, amino ($-CH_2CH_2CH_2CH_2NH_2$) for lysine, thiol ($-CH_2SH$) of cystein, imidazole amine of histidine

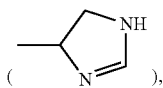

secondary aliphatic hydroxyl group ($-CH_2CH(OH)CH_3$) of threonine, primary aliphatic hydroxyl group ($-CH_2OH$) of serine and phenol hydroxyl group

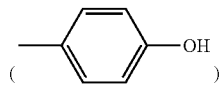

of tyrosine and the like may be mentioned. Also, reactive groups in dyes may be bound to n-terminal amino group ($-COCHRNH_2$) in amino acid. In addition, reactive groups in dyes may be bound to biomolecules such as sugar, glycoprotein and antibodies.

Reactive groups used for dyes or molecules for labeling biomolecules known to date are classified depending on substitution groups bound to biomolecules and are also called trivial names.

The most common reactive groups bound to amine of protein molecules are ester and isothiocyanate, and the most common reactive group bound to thiol of protein molecules is maleimide and reactive groups bound to hydroxyl groups of protein molecules are as follows:

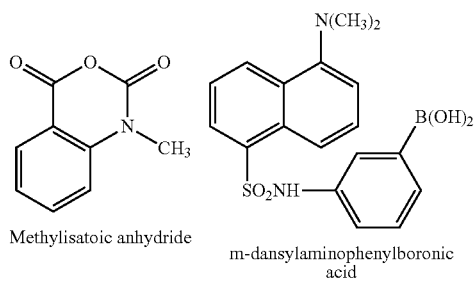

Methylisatoic anhydride m-dansylaminophenylboronic acid

In addition to these reactive groups, numerous researchers and enterprises are designing reactive group intermediates exhibiting superior performance. Most intermediates exhibit short reaction time with biomolecules and superior bonding performance, but are unstable in an aqueous solution state and are vulnerable to heat and produce by-products, while leaving groups are cleaved after reaction.

Water-soluble fluorescent dyes are actively applied to the field of biology. In order to incorporate water-soluble fluorescent dyes into biomolecules, the water-soluble fluorescent dyes should not cause photo-bleaching and quenching under aqueous or hydrophilic solution conditions, have a high molecular extinction coefficient sufficient to absorb a great deal of light, be within 500 nm or higher of visible or near infrared rays far from the fluorescent range of biomolecules and be stable under various pH conditions. However, structures of dyes useful for labeling biomolecules are limited due to various conditions.

All dyes are not fluorescent. Researchers in a variety of fields have developed dyes having fluorescent chromophores. Representative examples of fluorophores known to date include anthranilate, 1-alkylthic isoindoles, pyrrolinones, bimanes, benzoxazole, benzimidazole, benzofuran, naphthalenes, coumarins, stilbenes, carbazoles, phenanthridine, anthracenes, acridines, fluoresceins, eosins, rhodamines, pyrenes, chrysenes and the like. Derivatives similar to these fluorophores are also researched. These fluorophores are incorporated into various reactive groups to be bound to biomolecules and are thus commercially available as various products.

It is noted that these various fluorescent dyes should exhibit strong fluorescence in a medium in which most biomolecules are present, that is, an aqueous solution, in order that the dyes exhibit fluorescence applicable to the field of biology. The most commonly used fluorescent dyes for such application are xanthene-based fluorescein and rhodamine, and polymethine-based cyanine.

Cyanine dyes were first applied to biomolecular-labeling by Dr. Waggoner's team in the Carnegie Mellon University near the end of the 1980's. Dr. Waggoner's team found that binding of cyanine dyes mainly used for cloth dying or optical recording media, into which reactive groups that can be linked to proteins are incorporated, to proteins, causes expression of fluorescence and then reported the following several articles.

[Document 1] Ernst, L. A., Gupta, R. K., Mujumdar, R. B., and Waggoner, A. S. (1989) Cyanine Dye Labeling Reagents for Sulfhydryl groups. Cytometry 10, 3-10.

[Document 2] Mujumdar, R. B., Ernst, L. A., Mujumdar, S. R., and Waggoner, A. S. (1989) Cyanine Dye Labeling Reagents containing Isothiocyanate groups. Cytometry 10, 11-19.

[Document 3] Southwick, P. L., Ernst, L. A., Tauriello, E. W., Stephen, R. P., Mujumdar, R. B., Mujumdar, S. R., Clever, H. A., and Waggoner, A. S. (1990) Cyanine Dye Labeling reagents—Carboxymethylindocyanine Succinimidyl Esters. Cytometry 11, 418-430.

[Document 4] Mujumdar, R. B., Ernst, L. A., Mujumdar, S. R., Lewis, C. J., and Waggoner, A. S. (1993) Cyanine Dye Labeling Reagents: Sulfoindocyanine Succinimidyl Esters. Bioconjugate Chem. 4, 105-111.

[Document 5] Mujumdar, S. R., Mujumdar, R. B., Grant, C. M., and Waggoner, A. S. (1996) Cyanine-Labeling Reagents: Sulfobenzindocyanine Succinimidyl Esters. Bioconjugate Chem. 7, 356-36.

Then, for various applications, numerous researchers introduced protein nucleophiles, that is, amine, thiol and hydroxyl groups, and pigments and fluorescent dyes for labeling biomolecules, into which reactive groups bound to electrophiles, that is, aldehyde, ketone and carboxylic acid groups, are incorporated.

Generally, cyanine dyes exhibit optical and pH stability, have narrow absorption and emission wavelength ranges and are fluorescent in the range of 500 to 800 nm. This fluorescence range of cyanine dyes does not overlap with the self-fluorescence range of biomolecules, thus advantageously making it easy to analyze. In addition, cyanine dyes exhibit high molecular extinction coefficients, although there are slight differences therebetween depending on characteristics of solvent and solubility. The following Formulas represent a generic structure of cyanine dyes shown in the documents and basic structures of hetero compounds known as derivatives.

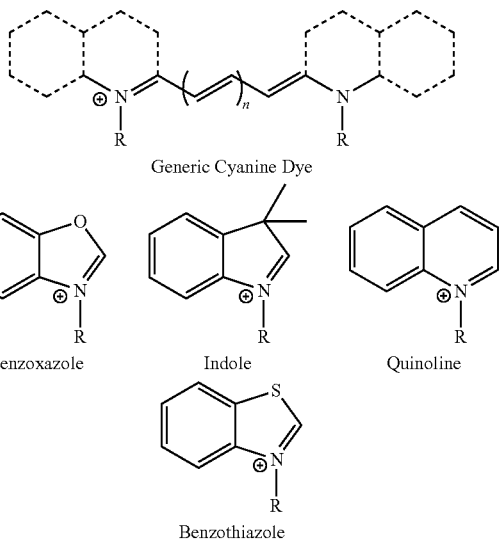

Most commercially available cyanine dyes have indole structures as hetero rings and succinimidyl ester as reactive groups. The Formula represented below is a representative structure of cyanine dyes, which are commercially available under the trade names Cy3, Cy5 and Cy7 from GE healthcare Co., Ltd.

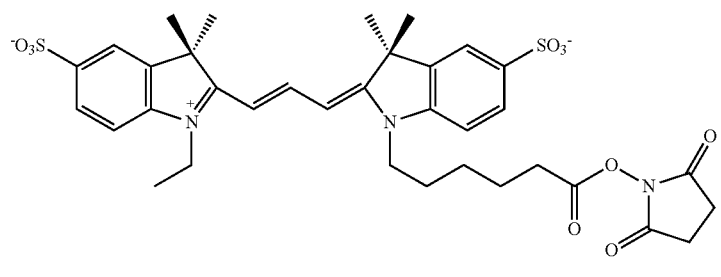

Cy3 (Commercial)

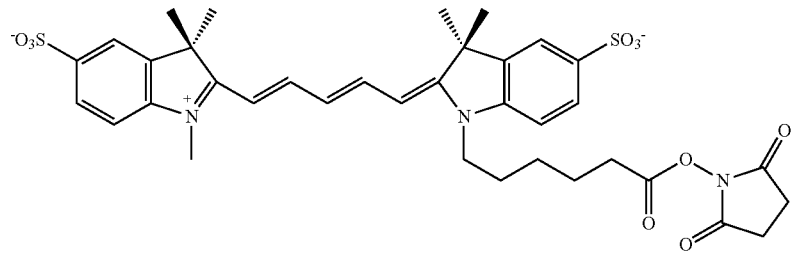

Cy5 (Commercial)

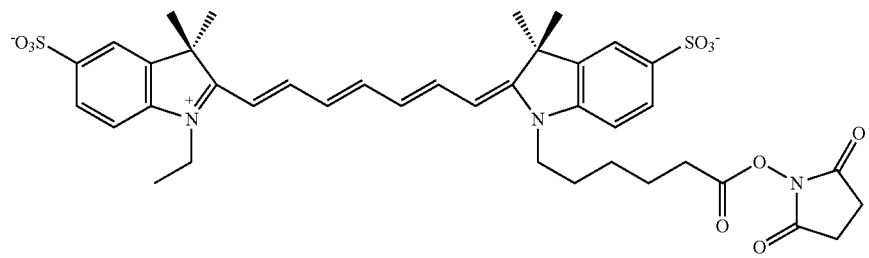

Cy7 (Commercial)

Unlike cloth dyes requiring various colors, fluorescent dyes for labeling biomolecules having a wide fluorescence wavelength range are not necessarily preferable. This is the reason that wavelengths of equipment using or measuring fluorescence are limited. Unless novel fluorescence analysis methods or apparatuses are developed, optical equipment is improved, or performance thereof is suited for dyes, variations in chromogens or structures varying light-absorption or light-emission wavelength ranges are not significant in view of commercialization in the field of dyes for labeling biomolecules.

It is known that like dyes having different chromogens, cyanine dyes have polymethine as a chromogen, regardless of incorporation of reactive groups, and thus substantially maintain fluorescence properties and undergo almost no variation in light-absorption and light-emission wavelengths.

Cyanine-labeling dyes having succinimidyl ester, used for labeling biomolecules, are dyed in a carbonate or phosphate buffer solution. Generally, the buffer is used in a concentration of 0.1M and the reaction is carried out at room temperature.

A dye is dissolved in N,N-dimethylformamide (DMF) or N,N-dimethyl sulfoxide (DMSO). 1 mg of the dye is dissolved in 100 μl of solvent and the resulting solution is then aliquoted. The dye is used in an excess of 5- to 100-fold equivalents with respect to biomolecules to be stained because, although a protein molecule is used in an amount of one equivalent, the number of amino, hydroxyl or thiol groups targeted by the reaction is much greater. Dyes require higher aqueous solution stability, in order for the dyes to be permeated into complicated protein structures and thus react therewith. However, it is disadvantageous that succinimidyl ester cannot be stably maintained for a long period of time.

SUMMARY OF THE INVENTION

Therefore, the present invention has been made in view of the above problems, and it is one object of the present invention to provide a novel cyanine compound which may be widely used to identify biomolecules such as proteins, lipids or carbohydrates in the field of proteomics and optical molecular imaging, and a method for preparing the same.

In accordance with the present invention, the above and other objects can be accomplished by the provision of a novel cyanine compound represented by Formula 1 below:

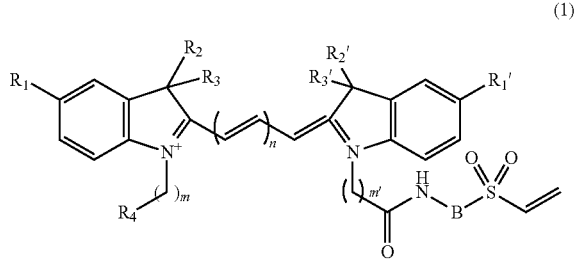

(1)

wherein $R_1$ and $R_1'$ are each independently hydrogen, a sulfonic acid group or a sulfonic acid base;

$R_2$, $R_2'$, $R_3$ and $R_3'$ are each independently hydrogen or a $C_1$-$C_6$ alkyl group;

$R_4$ is hydrogen, a $C_1$-$C_6$ alkyl group, a carboxyl group, —CONH(CH$_2$)$_L$SO$_2$CH=CH$_2$, —CONH-para-(C$_6$H$_4$)SO$_2$CH=CH$_2$ or —CONH-meta-(C$_6$H$_4$)SO$_2$CH=CH$_2$;

B is (CH$_2$)$_l$, para-(C$_6$H$_4$) or meta-(C$_6$H$_4$);

m and m' are each independently an integer of 1 to 5; and

L, l and n are each independently an integer of 1 to 5, and a method for preparing the same.

In accordance with another aspect, provided is a method for labeling biomolecules, nanoparticles or organic compounds with the compound of Formula 1 in the presence of various solvents, for example, in a buffer solution (so-called, binding protocol).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which:

FIG. 5C shows absorbance (650 nm) of the reaction product of benzyl mercaptan therewith;

FIG. 7I illustrates fluorescence intensity of aprotinin.

DETAILED DESCRIPTION OF THE INVENTION

Figure 1:
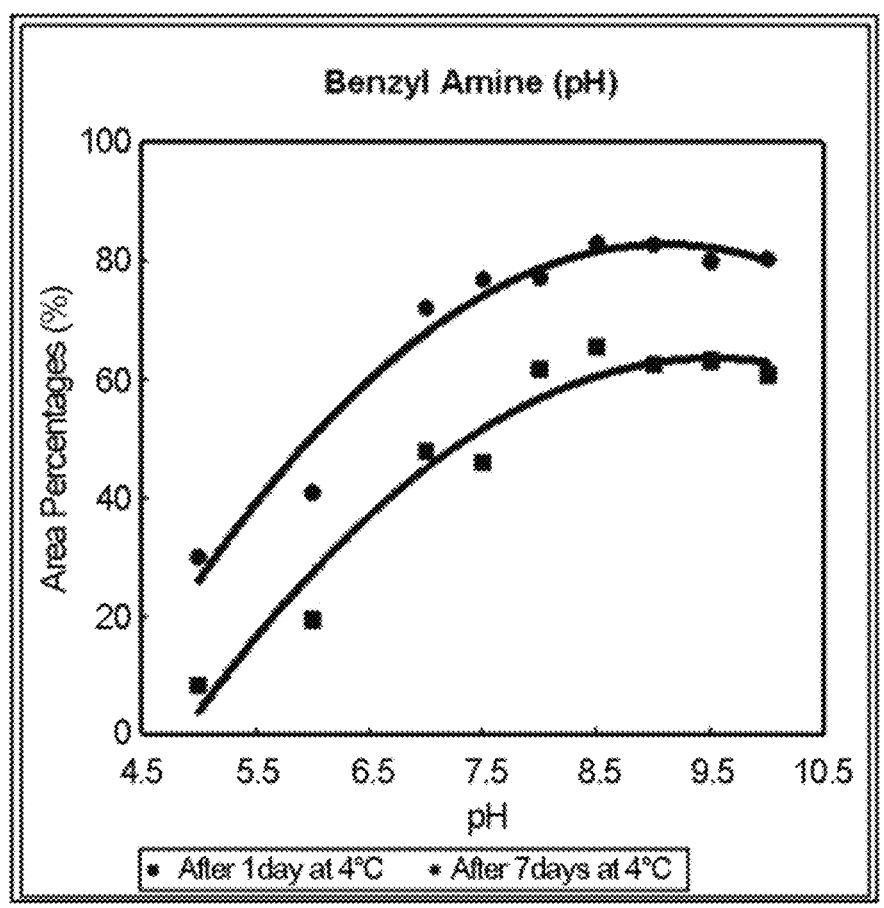
FIG. 1 illustrates absorbance (at 550 nm) of the compound 1-16 confirmed in Example 22.

The most commonly used dye reactive group for protein staining is succinimidyl ester that can be bound to the amines of amino acids. For example, U.S. Pat. Nos. 5,268,486, 6,043,025 and 6,127,134 (GE healthcare) and PCT laid-open No 96/33406 illustrate a method for staining biomolecules such as antibodies or peptides with various cyanine dye structures into which succinimidyl ester is incorporated. However, this succinimidyl ester is not stable in an aqueous solution and necessarily produces N-hydroxy succinimide as a by-product, during staining.

Accordingly, the present invention aims to develop dye products that do not produce by-products after dying with biomolecules. In addition, taking into consideration the fact that bio-labeling methods using conventional succinimidyl ester are well known, a dying method enabling easy labeling of proteins using a conventional method has been developed to exert superior performance. Also, dying methods performed in the presence of various buffer solutions are suggested.

The cyanine compound of Formula 1 is characterized in that vinyl sulfone is incorporated therein. Vinyl groups of the vinyl sulfone are bound to nucleophiles of biomolecules in accordance with the following mechanism and the compound of Formula 1 thus does not produce by-products after reaction with biomolecules.

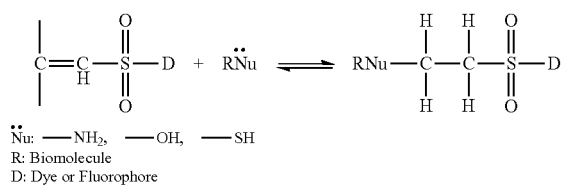

Nu: —NH$_2$, —OH, —SH
R: Biomolecule
D: Dye or Fluorophore

The cyanine dye compounds of the present invention are designed to target water as a medium and be stable against heat, when they are applied to most biomolecules.

In addition, the present invention is directed to a method for preparing the novel cyanine compound represented by Formula 1.

Hereinafter, the method for preparing the novel cyanine compound represented by Formula 1 will be described in detail.

In accordance with the method for preparing the compound of Formula 1, a compound of Formula 2 reacts with a compound of Formula 3, as depicted in Reaction Scheme 1a, to obtain a compound of Formula 4a, which is used as a starting material.

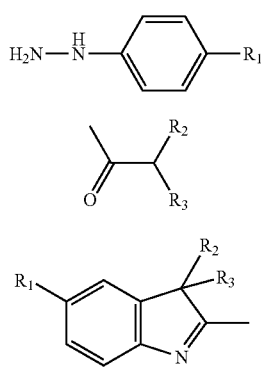

[Reaction Scheme 1a]

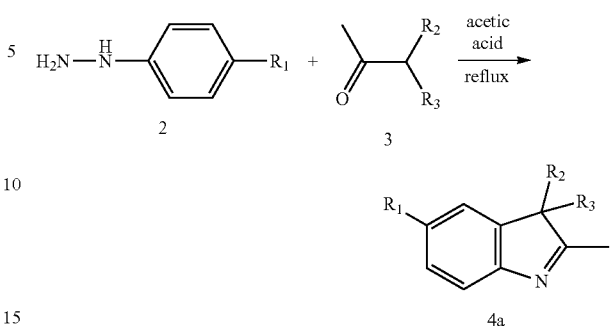

In Formulae 2 to 4 and Reaction Scheme 1a, $R_1$, $R_2$ and $R_3$ are defined as in Formula 1.

When $R_1$ of Formula 4a is a sulfonic acid group, the compound of Formula 4a is treated with an inorganic base represented by general formula "MOH", preferably, potassium hydroxide or sodium hydroxide, most preferably, potassium hydroxide, to obtain a compound of Formula 4b, in which $R_1$ is a sulfonic acid base, which may be used as a starting material, as depicted in Reaction Scheme 1b below:

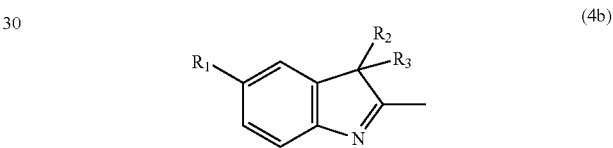

[Reaction Scheme 1b]

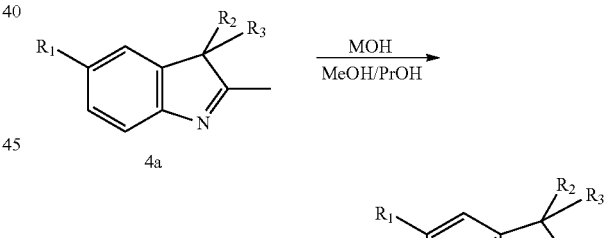

In Reaction Scheme 1b, M is potassium or sodium, $R_2$ and $R_3$ are defined as in Formula 1, $R_1$ of Formula 4a is a sulfonic acid group, and $R_1$ of Formula 4b is a sulfonic acid base.

In order to prepare the compound of Formula 1, first, the compound of Formula 4a or 4b reacts with compounds of the following Formulae 5 and 7, to obtain a compound of Formula 6a or 6b, as depicted in Reaction Schemes 2 and 3.

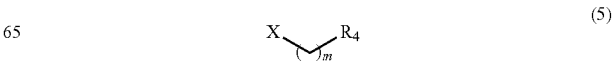

-continued

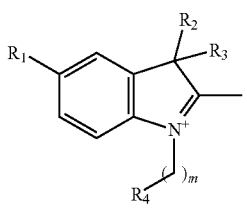
(6a)

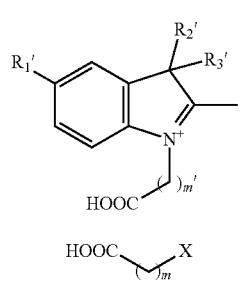
(6b)

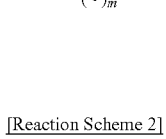
(7)

[Reaction Scheme 2]

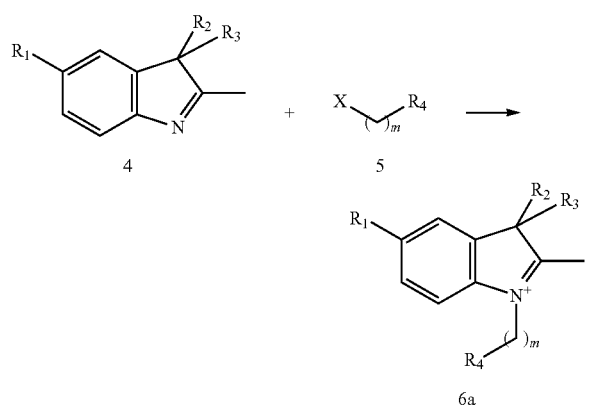

[Reaction Scheme 3]

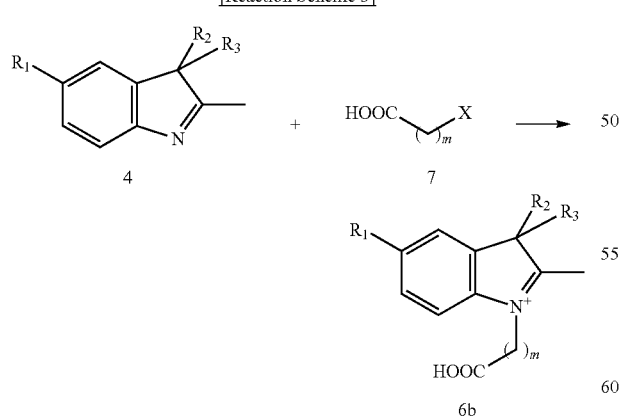

In Formulae 5 to 7 and Reaction Schemes 2 and 3, $R_1$, $R_2$, $R_3$, $R_4$ and m are each independently defined as in Formula 1 and X is a halogen atom selected from the group consisting of fluorine, chlorine, bromine and iodine.

Reaction Scheme 2 illustrates a method for preparing a compound of Formula 6a wherein $R_4$ is hydrogen or an alkyl group having 1 to 6 carbon atoms, and Reaction Scheme 3 illustrates a method for preparing a compound of Formula 6b wherein $R_4$ is a carboxyl group.

Then, the compound of Formula 6a or 6b reacts with the following compound of Formula 8 to obtain a compound of Formula 9.

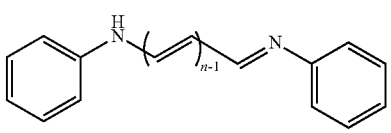
(8)

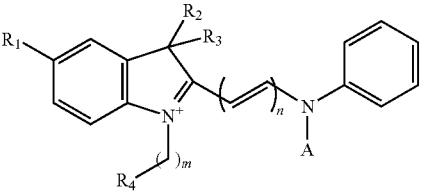
(9)

[Reaction Scheme 4]

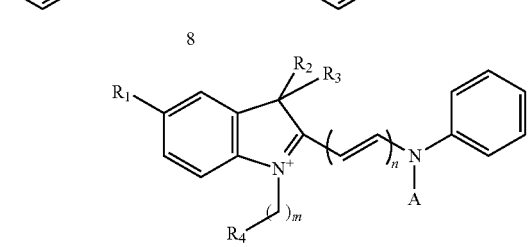

In Formulae 8 and 9, and Reaction Scheme 4, $R_1$, $R_2$, $R_3$, $R_4$, m and n are each independently defined as in Formula 1, and A is hydrogen or an acetyl group.

The compound of Formula 8 is N,N-diphenyl formamidine (DPF), when n is 1, the compound of Formula 8 is malondialdehyde dianil hydrochloride (MDH), when n is 2, and the compound of Formula 8 is glutaconaldehyde dianil hydrochloride (GDH), when n is 3.

Then, the compound of Formula 9 reacts with a compound of Formula 6b to obtain a compound of Formula 10, as depicted in Reaction Scheme 5 below.

(10)

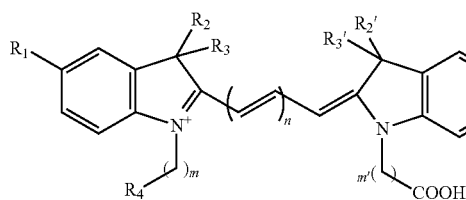

[Reaction Scheme 5]

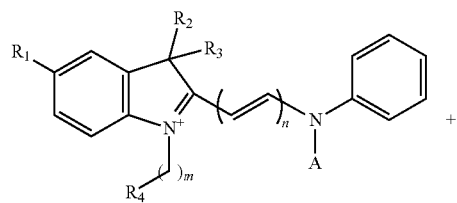

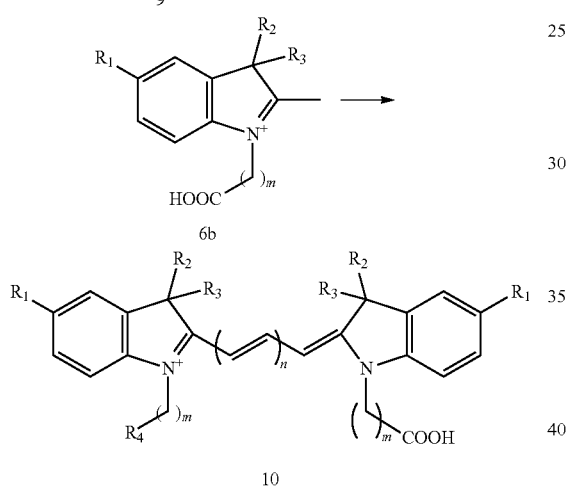

In Formula 10 and Reaction Scheme 5, $R_1$, $R_2$, $R_3$, $R_4$, m and n are each independently defined as in Formula 1. The two $R_1$, may be the same as or different from each other, the two $R_2$ may also be the same as or different from each other, and the two $R_3$ may also be the same as or different from each other. In addition, the two m may also be the same as or different from each other.

Then, the compound of Formula 10 reacts with, 1'-carbonyl diimidazole (CDI) or N,N-disuccinimidyl carbonate (DSC) to obtain a compound of Formula 11a or 11b, as depicted in Reaction Scheme 6 below.

(11a)

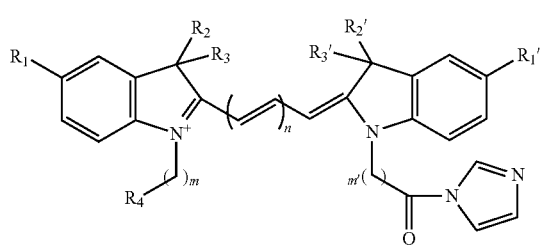

(11b)

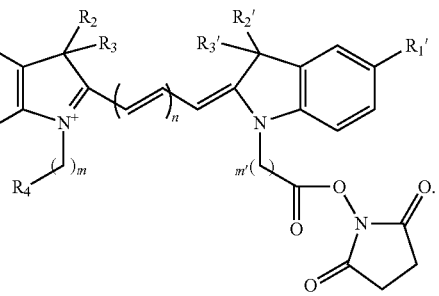

In Formulae 11a and 11b, $R_1$, $R_2$, $R_3$, $R_4$, m and n are each independently defined as in Formula 1. The two $R_1$ may be the same as or different from each other, the two $R_2$ may also be the same as or different from each other, and the two $R_3$ may also be the same as or different from each other. In addition, the two m may also be the same as or different from each other.

[Reaction Scheme 6]

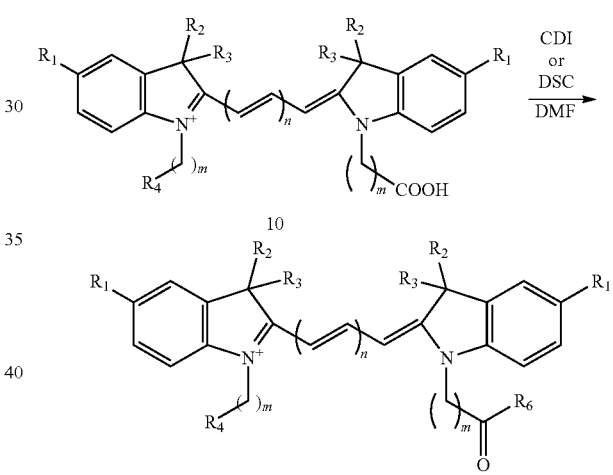

In Reaction Scheme 6, $R_1$, $R_2$, $R_3$, $R_4$, m and n are each independently defined as in Formula 1, $R_6$ is an imidazole group in Formula 11a, and $R_6$ is a succinimidyloxy group in Formula 11b. The two $R_1$ may be the same as or different from each other, the two $R_2$ may also be the same as or different from each other, and the two $R_3$ may also be the same as or different from each other. In addition, the two m may be also the same as or different from each other.

Then, the compound of Formula 11a or 11b reacts with a compound represented by Formula 12 in the presence of a Hunig's base to obtain a compound of Formula 1, as depicted in Reaction Scheme 7 below.

(12)

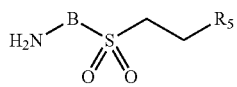

[Reaction Scheme 7]

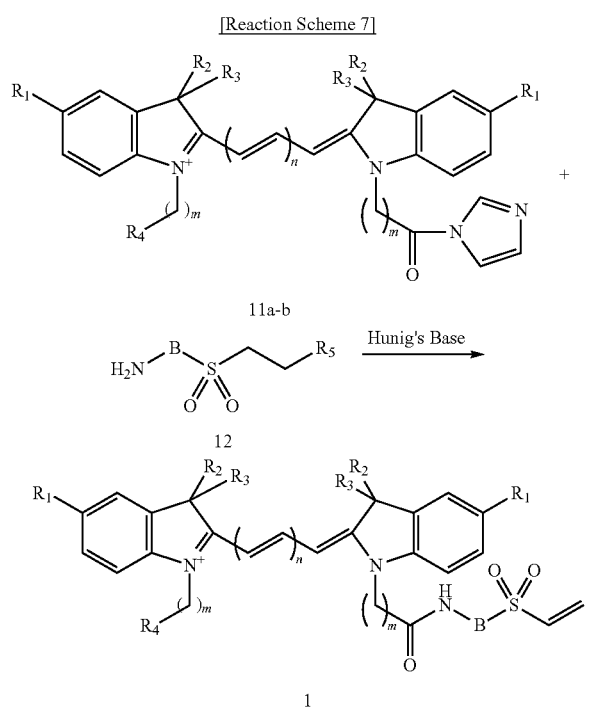

In Formula 12 and Reaction Scheme 7, $R_1$, $R_2$, $R_3$, $R_4$, m and n are each independently defined as in Formula 1, $R_5$ is a halogen atom selected from the group consisting of fluorine, chlorine, bromine and iodine, or a sulfato group ($-OSO_3H$), B is $(CH_2)_l$, p-$(C_6H_4)$ or m-$(C_6H_4)$, and l is an integer of 1 to 5. The two $R_1$ may be the same as or different from each other, the two $R_2$ may also be the same as or different from each other, and the two $R_3$ may also be the same as or different from each other. In addition, the two m may also be the same as or different from each other.

In addition, the present invention is directed to a method for labeling biomolecules, nanoparticles or organic compounds containing an amine group, a hydroxyl group or a thiol group using the novel cyanine compound of Formula 1 (binding protocol).

Preferably, the biomolecules are selected from the group consisting of proteins, peptides, carbohydrates, sugars, lipids, antibodies, proteoglycans, glycoproteins and siRNA.

The labeling is carried out by binding the compound of Formula 1 to biomolecules, nanoparticles or organic compounds, specifically, to the amine, hydroxyl or thiol groups present in the biomolecules, nanoparticles or organic compounds through reaction of vinyl sulfone present in the compound of Formula 1 with the amine, hydroxyl or thiol group.

Like conventional cyanine dyes having succinimidyl ester, the compound of Formula 1 can readily stain proteins through reaction therewith.

Accordingly, the labeling is carried out by reacting the compound of Formula 1 with the biomolecules, nanoparticles or organic compounds at pH 5 to 12 using, as a solvent, a buffer solution selected from the group consisting of a phosphate buffer solution, a carbonate buffer solution and a tris buffer solution, an organic solvent selected from the group consisting of dimethyl sulfoxide, dimethyl formamide, methanol, ethanol and acetonitrile, or water. The reaction is carried out at a temperature of 20 to 80° C. for 30 minutes to 48 hours.

Also, the present invention is directed to a material selected from biomolecules, nanoparticles and organic compounds labeled with the compound of Formula 1.

Biomolecules are generally dissolved in a predetermined buffer solution in a package unit. In order to secure stability of biomolecules, additional buffer solutions or pH are frequently required, making stability control through parameters difficult. The compound of Formula 1 readily reacts with proteins under various buffer conditions, reaction temperatures and pH to express fluorescence, thus being suitable for use in biomolecular labeling.

EXAMPLES

Hereinafter, the present invention will be described with reference to Examples and Comparative tests in detail. The following examples are for illustrative purposes only and are not intended to limit the scope of the present invention.

First, test apparatuses, analysis equipment and reagents used for Examples and Comparative tests will be described in detail.

The apparatuses used herein for FT-NMR spectroscopic analysis were Avance 300 and 400 (Bruker Co. Ltd.) and 1200L Quadrupole was used for LC/MS (Varian Co. Ltd.) in accordance with electrospray ionization (ESI). Voyager MALDI-TOF DE was used as a mass spectrometer for MALDI-TOF M/S.

The absorption wavelengths and maximum absorption wavelengths of synthesized dyes were measured with an HP 8452 diode array spectrophotometer (Hewlett-Packard), and luminescence values at luminescent wavelengths and maximum luminescent wavelengths were obtained using LS-55 (Perkin Elmer Co.).

Column chromatography to separate and purify organic compounds was carried out using kiesel gel 60 (230-400 mesh, Merck & Company Inc.) as a silica gel in the case of a normal phase. A glass substrate on which silica gel 60 GF254 (0.25 mm, Merck) was coated was used for thin layer chromatography (TLC). The identification of the compound through TLC was carried out using ultraviolet light at 254 nm and 365 nm, or a 20 to 30% ethanolic phosphomolybdic acid (PMA) solution or $KMnO_4$ as a chromogen. In the case of reverse phase, TLC was carried out using a glass substrate on which silica gel 60 RP-18 $F_{254S}$ (0.25 mm, Merck) was coated, and column chromatography was carried out using a Lichroprep RP-18 reverse phase column (40 to 63 µm, Merck) coupled to Fraction Collector R-660 as an apparatus for medium pressure liquid chromatography (MPLC, Buchi). HPLC was carried out using Bondapak C18 10 µm 125A (Waters) coupled to 1100 series (Agilent).

The apparatus for gel electrophoresis used herein was PowerPac Basic Power Supply (Catalog No. 164-5050, BIO-RAD) coupled to an SE 260 mini-vertical gel electrophoresis unit (Amersham Biosciences). PAGEr Gold Precast Gels (Polyacrylamide gels for protein electrophoresis, 10 to 20% Tris-Glycine gels, Catalog No. 59506, Lonza) were used as gels. The running and loading buffers for SDS-PAGE tests were directly prepared under the following conditions prior to use.

Preparation of 5× Running Buffer
3 g of Tris (Trizma base, Sigma)
14.4 g of Glycine (Sigma)
100 mL of distilled water refrigerated after preparation
Preparation of 5× Loading Buffer
0.6 mL of 1 M Tris (Trizma base, Sigma)
5 mL of 50% glycerol
2 mL of 10% SDS 0.5 mL of 2-mercaptanethanol 1.9 mL of 10% distilled water (instead of bromophenol blue)

Proteins used herein were Size Markers commercially available from GE Healthcare Co., Ltd. and Takara Co., Ltd. A Geliance 600 (Perkin Elmer) was used to observe the labeled biomolecules and measure fluorescence intensity. Light sources used herein were Geliance UV Epi (Catalog No. L7110026) and Geliance Blue Epi (Catalog No. L7110027). The measurement was carried out using a UV Filter, Geliance Short Pass Filter (500-600 nm), Geliance Long Pass Filter (580 to 660 nm), and Geliance Blue Light Filter (550-600 nm) as filters in accordance with fluorescence wavelengths.

Reagents used herein were products available from Aldrich Co., Ltd. and TCI Co., Ltd. Solvents requiring purification were purified in accordance with a known method prior to use. Unless specifically mentioned, all reactions were carried out under nitrogen current. NMR solvents used herein were DMSO-$d_6$ or $D_2O$ available from Aldrich Co., Ltd. and Cambridge Isotope Laboratories Inc. Relative positions of signals were determined based on tetramethylsilane (TMS) in a solvent or an NMR solvent. Chemical shift was expressed in ppm from a standard material and data of chemical shift multiplicity (s=singlet, d=doublet, t=triplet, m=multiplet), intergration and coupling constant (Hz) were sequentially recorded.

Example 1

Preparation of Compound 1-1

(1) Synthesis of Compound 4-1

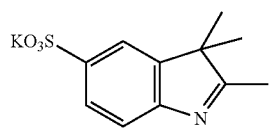

4-1 p-hydrazinobenzenesulfonic acid (10 g, 53 mmol, 1 eq, Aldrich) and 3-methyl-2-butanone (17.18 mL, 160 mmol, 3.02 eq, TCI) were added to acetic acid (30 mL), and the resulting mixture was heated under reflux for 4 hours. The reaction mixture was allowed to cool to ambient temperature and the resulting solid particles were filtered. The filtrate was washed with ethyl acetate two or three times and dried under reduced pressure (11.34 g, 89%).

$R_f$=0.68 (RP-C18, acetonitrile/water 1:4 v/v)

A solution of the solid substance (5.073 g, 21.2 mmol, 1 eq) thus prepared in methanol (35 mL) was added dropwise to a solution of potassium hydroxide (1.427 g, 25.4 mmol, 1.2 eq) in propanol (35 mL), and the mixture was stirred at ambient temperature for 24 hours and filtered to obtain a yellow particulate solid (5.35 g, 90%).

$R_f$=0.68 (RP-C18, acetonitrile/water 1:4 v/v)

$^1$H NMR (300 MHz, $D_2O$): δ 7.60 (s, 1H), 7.58 (d, 1H, J=8.32 Hz), 7.32 (d, 1H, J=7.99 Hz), 2.08 (s, 3H), 1.06 (s, 6H)

(2) Synthesis of Compound 6a-1

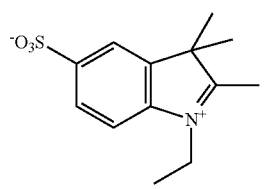

6a-1

The compound 4-1 (20 g, 72.1 mmol, 1 eq) and ethyl iodide (110 mL, 1.375 mmol, 19 eq, TCI) were added to the solid thus obtained and the mixture was heated under reflux for 24 hours. The reaction mixture was allowed to cool to ambient temperature, the ethyl iodide was removed, and the residue was washed with 50 mL of acetone three or four times, filtered, and dried under reduced pressure at 40° C. to obtain a pink solid (18.37 g, 95%).

$R_f$=0.18 (RP-C18, acetonitrile/water 1:4 v/v)

$^1$H NMR (400 MHz, $D_2O$): δ 7.99 (s, 1H), 7.88 (d, 1H, J=8.23 Hz), 7.80 (d, 1H, J=8.46 Hz), 4.43 (m, 2H), 1.52-1.40 (m, 12H)

LC/MS, $C_{13}H_{18}NO_3S^+$, calculated value: 268.1, measured value: 268.16

(3) Synthesis of Compound 6B-1

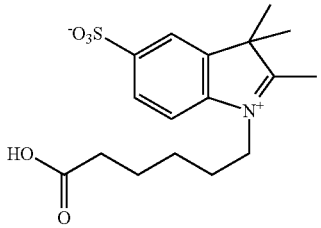

6b-1

The compound 4-1 (2.774 g, 10 mmol, 1 eq) and 6-bromo-n-hexanoic acid (2.34 g, 12 mmol, 1.2 eq, Aldrich) were heated under reflux in 15 mL of 1,2-dichlorobenzene for 12 hours. The reaction mixture was allowed to cool to ambient temperature, the solvent was removed, isopropyl alcohol was added to the residue, and the resulting mixture was filtered and dried under reduced pressure to obtain a pink solid (2.653 g, 75%).

$R_f$=0.08 (RP-C18, acetonitrile/water 1:4 v/v)

$^1$H NMR (400 MHz, $D_2O$): δ 8.00 (s, 1H), 7.90 (d, 1H, J=8.86 Hz), 7.77 (d, 1H, J=8.43 Hz), 4.37 (t, 2H, J=7.46 Hz), 2.25 (t, 2H, J=7.01 Hz), 1.85 (m, 2H), 1.57-1.26 (m, 13H)

LC/MS, $C_{17}H_{24}NO_5S^+$, calculated value: 354.14, measured value: 354.18

(4) Synthesis of Compound 9-1

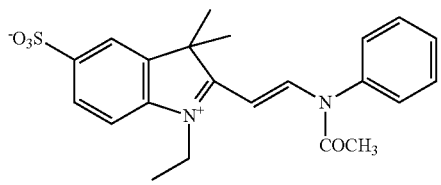

9-1

The compound 6a-1 (16 g, 59.8 mmol, 1 eq) and DPF (13.2 g, 67.3 mmol, 1.125 eq, TCI) were added to a solution consisting of 40 mL of acetic acid and 40 mL of anhydrous acetic acid, and the resulting mixture was heated under reflux for 4 hours. The reaction mixture was allowed to cool to ambient temperature, the solution was removed, ethyl acetate was added to the residue to produce a solid, and the resulting solid was filtered and dried under reduced pressure (12.97 g, 57%).

$R_f$=0.25 (RP-C18, acetonitrile/water 1:4 v/v)

$^1$H NMR (300 MHz, DMSO-$d_6$): δ 7.85 (s, 1H), 7.70 (dd, 1H, J=1.35 Hz, 1.32 Hz), 7.53-7.45 (m, 7H), 7.29 (dd, 1H, J=1.92 Hz, 6.66 Hz), 4.13 (m, 2H), 1.70 (s, 6H), 1.32 (t, 3H, J=7.05 Hz)

LC/MS, $C_{20}H_{23}N_2O_3S^+$, calculated value: 371.14, measured value: 370.98

(5) Synthesis of Compound 10-1

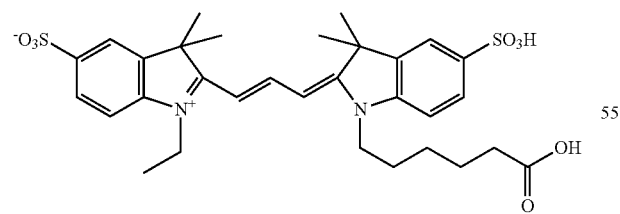

10-1

The compound 9-1 (1.01 g, 2.429 mmol, 1 eq) and the compound 6b-1 (0.86 g, 2.429 mmol, 1 eq) were added to a solution consisting of 5 mL of anhydrous acetic acid and 5 mL of pyridine and the mixture was allowed to react at 110° C. for 4 hours. The reaction mixture was allowed to cool to ambient temperature, and a solid was precipitated through addition of ethyl acetate, was filtered and dried under reduced pressure. The resulting product was purified by RP-C18 reverse phase chromatography using 15% acetonitrile aqueous solution as an eluent to obtain a pure compound 10-1 (0.37 g, 24%).

$R_f$=0.70 (RP-C18, acetonitrile/water 3:7 v/v)

$^1$H NMR (300 MHz, $D_2O$): δ 8.38 (t, 1H, J=13.5 Hz), 7.78 (s, 2H), 7.73 (t, 2H, J=7.42 Hz), 7.23 (dd, 2H, J=5.25 Hz, 7.97 Hz), 6.24 (dd, 2H, J=4.79 Hz, 4.56 Hz), 3.97 (m, 4H), 2.23 (t, 2H, J=7.26 Hz), 1.73-1.20 (m, 21H)

LC/MS, $C_{31}H_{39}N_2O_8S_2^+$, calculated value: 631.21, measured value: 631.31

$\lambda_{abs}$ (water): 549 nm, $\lambda_{fl}$ (water): 573 nm

(6) Synthesis of Compound 1-1

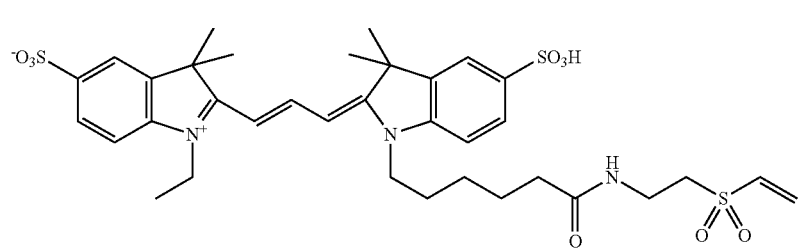

1-1

The compound 10-1 (110 mg, 0.174 mmol, 1 eq) was dissolved in DMF (22 mL) and the temperature was elevated to 55° C. 0.11 mL of pyridine was added to the solution and a solution of DSC (135 mg, 0.527 mmol, 3.02 eq, Aldrich) in DMF (2.5 mL) was added dropwise thereto. The resulting mixture was stirred for one hour, a red solid was a precipitated through addition of ethyl acetate, was washed several times with ethyl acetate and ether and filtered. The filtrate was dissolved in DMF (20 mL), 0.302 mL of Hunig's base was added thereto, a solution of 2-(2'-chloroethylsulfonyl)ethylamine hydrochloride (36 mg, 0.174 mmol, 1 eq) dissolved in 1 mL of DMF was dropwise added thereto, and the resulting mixture was stirred for 12 hours or longer. The reaction mixture was extracted in water and methylene chloride (dichloromethane), and distilled under reduced pressured at 35 to 40° C. to remove the solvent. The residue was purified by RP-C18 reverse phase chromatography using 15% acetonitrile aqueous solution as an eluent to obtain a pure compound 1-1 (106.4 mg, 82%).

$R_f$=0.65 (RP-C18, acetonitrile/water 3:7 v/v)

$^1$H NMR (400 MHz, DMSO-$d_6$): δ 8.32 (t, 1H, J=13.4 Hz), 8.02 (t, 1H, J=4.9 Hz), 7.80 (s, 2H), 7.67 (m, 2H), 7.39 (dd, 2H, J=2.88 Hz, 3 Hz), 6.96 (dd, 1H, J=9.92 Hz, 9.92 Hz), 6.53 (dd, 2H, J=4.24 Hz, 4.32 Hz), 6.23 (m, 2H), 4.17-4.09 (m, 4H), 3.21 (m, 2H), 2.04 (t, 2H, J=6.96 Hz), 1.69-1.28 (m, 23H)

LC/MS, $C_{35}H_{44}N_3O_9S_3^-$, calculated value: 746.22, measured value: 746.27

$\lambda_{abs}$ (water): 549 nm ($\epsilon$=1.222×10$^5$M$^{-1}$ cm$^{-1}$), $\lambda_{fl}$ (water): 574 nm

Example 2

Preparation of Compound 1-2

(1) Synthesis of Compound 9-2

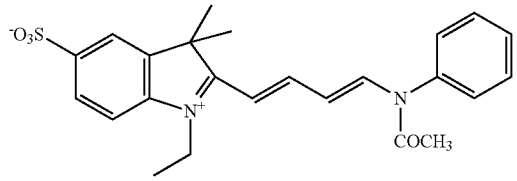

9-2

The compound 6a-1 (2.2 g, 8.23 mmol, 1 eq) and MDH (2.55 g, 9.88 mmol, 1.2 eq, TCI) were heated under reflux in a solution consisting of 10 mL of acetic acid and 10 mL of anhydrous acetic acid for 4 hours. The reaction mixture was allowed to cool to ambient temperature, the solvent was removed, a solid is precipitated through addition of ethyl acetate was filtered and then dried under reduced pressure (3.47 g, 96%).

$R_f$=0.20 (RP-C18, acetonitrile/water 1:4 v/v)

(2) Synthesis of Compound 10-2

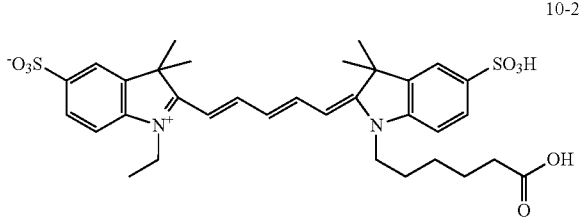

10-2

The compound 9-2 (6.40 g, 14.6 mmol, 1 eq) and the compound 6b-1 (5.12 g, 14.6 mmol, 1 eq) were added to 80 mL of pyridine and the resulting mixture was allowed to react at 60° C. for 4 hours. The reaction mixture was allowed to cool to ambient temperature, and a blue solid was precipitated through addition of ethyl acetate, was filtered and dried under reduced pressure. The resulting product was purified by RP-C18 reverse phase chromatography using 25% acetonitrile aqueous solution as an eluent to obtain a pure compound 10-2 (2.09 g, 22%).

$R_f$=0.58 (RP-C18, acetonitrile/water 3:7 v/v)

$^1$H NMR (400 MHz, DMSO-$d_6$): δ 8.34 (t, 2H, J=13.2 Hz), 7.80 (s, 2H), 7.63 (d, 2H, J=8.16 Hz), 7.30 (dd, 2H, J=2.80 Hz, 2.76 Hz), 6.58 (t, 1H, J=12.2 Hz), 6.30 (dd, 2H, J=8.64 Hz, 8.56 Hz), 4.13-4.06 (m, 4H), 1.98 (t, 2H, J=6.84 Hz), 1.72-1.18 (m, 21H)

LC/MS, $C_{33}H_{39}N_2O_8S_2^-$, calculated value: 655.22, measured value: 655.24

$λ_{abs}$ (water): 647 nm, $λ_{fl}$ (water): 678 nm (3) Synthesis of Compound 1-2

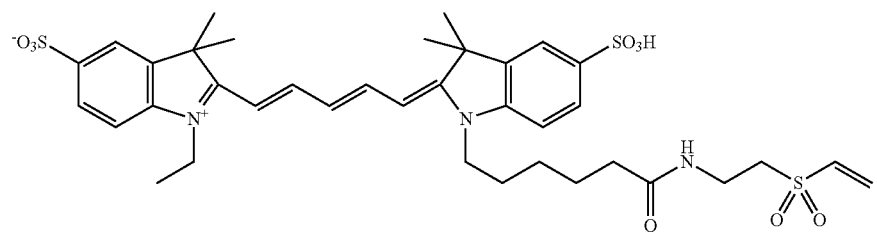

1-2

The compound 10-2 (20 mg, 0.0305 mmol, 1 eq) was dissolved in DMF (4 mL) and the temperature was elevated to 55° C. 0.02 mL of pyridine was added to the solution and a solution of DSC (40 mg, 0.156 mmol, 5.13 eq) in DMF (0.35 mL) was dropwise added thereto. The resulting mixture was stirred for one hour and a blue solid precipitated through addition of ethyl acetate was filtered and washed several times with ethyl acetate and ether. The filtrate was dissolved in DMF (4 mL), 40 mg of Hunig's base was added thereto, a solution of 2-(2'-chloroethylsulfonyl)ethyl amine hydrochloride (6.5 mg, 0.0312 mmol, 1.03 eq) dissolved in 0.1 mL of DMF was dropwise added thereto, and the resulting mixture was stirred at ambient temperature for 12 hours or longer. The reaction mixture was extracted in water and methylene chloride (dichloromethane), and distilled under reduced pressured at 35 to 40° C. to remove the solvent. The residue was purified by RP-C18 reverse phase chromatography using a 15% acetonitrile aqueous solution as an eluent to obtain a pure compound 1-2 (18.5 mg, 79%).

$R_f$=0.58 (RP-C18, acetonitrile/water 3:7 v/v)

$^1$H NMR (300 MHz, DMSO-$d_6$): δ 8.35 (t, 2H, J=13.0 Hz), 8.00 (t, 1H, J=5.21 Hz), 7.81 (s, 2H), 7.62 (d, 2H, J=10.3 Hz), 7.31 (d, 2H, J=7.50 Hz), 6.98 (dd, 1H, J=9.91 Hz, 9.92 Hz), 6.62 (t, 1H, J=12.3 Hz), 6.32-6.21 (m, 4H), 4.13-4.07 (m, 4H), 3.25 (m, 2H), 2.03 (t, 2H, J=7.13 Hz), 1.68-1.23 (m, 23H)

LC/MS, $C_{37}H_{48}N_3O_9S_3^+$, calculated value: 774.25, measured value: 774.29

$\lambda_{abs}$ (water): 648 nm (c=2.012×10$^5$M$^{-1}$ cm$^{-1}$), $\lambda_{fl}$ (water): 679 nm

Example 3

Preparation of Compound 1-3

(1) Synthesis of Compound 9-3

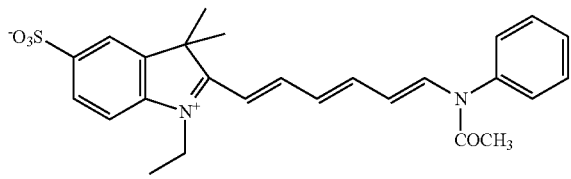

9-3

The compound 6a-1 (2.2 g, 8.23 mmol, 1 eq) and GDH (2.812 g, 9.87 mmol, 1.2 eq, TCI) were added to 10 mL of anhydrous acetic acid and the resulting mixture was allowed to react at 100° C. for one hour. The reaction mixture was allowed to cool to ambient temperature and a solid precipitated using ethyl acetate was filtered and dried under reduced pressure (2.92 g, 76%).

$R_f$=0.80 (RP-C18, acetonitrile/water 1:2 v/v)

(2) Synthesis of Compound 10-3

The compound 9-3 (7.2 g, 17.5 mmol, 1 eq) and the compound 6b-1 (5.94 g, 17.5 mmol, 1 eq) were dissolved in 108 mL of pyridine and the resulting mixture was allowed to react at 40° C. for one hour. The reaction mixture was allowed to cool to ambient temperature, and a green solid was precipitated through addition of ethyl acetate was filtered and dried under reduced pressure. The residue was purified by RP-C18 reverse phase chromatography using 30% acetonitrile aqueous solution as an eluent to obtain a pure compound 10-3 (2.59 g, 23%).

$R_f$=0.38 (RP-C18, acetonitrile/water 3:7 v/v)

$^1$H NMR (400 MHz, DMSO-d$_6$): δ 7.87 (t, 2H, J=12.8 Hz), 7.72 (m, 3H), 7.50 (d, 2H, J=11.9 Hz), 7.28 (d, 2H, J=8.24 Hz), 6.58-6.49 (m, 2H), 6.36 (d, 2H, J=13.7 Hz), 4.10-4.03 (m, 4H), 1.98 (t, 2H), 1.70-1.22 (m, 21H)

LC/MS, C$_{35}$H$_{41}$N$_2$O$_8$S$_2$$^-$, calculated value: 681.23, measured value: 681.28

$\lambda_{abs}$ (water): 748 nm, $\lambda_{fl}$ (water): 786 nm

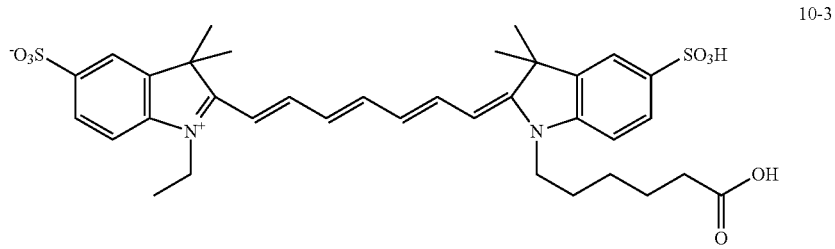

10-3

(3) Synthesis of Compound 1-3

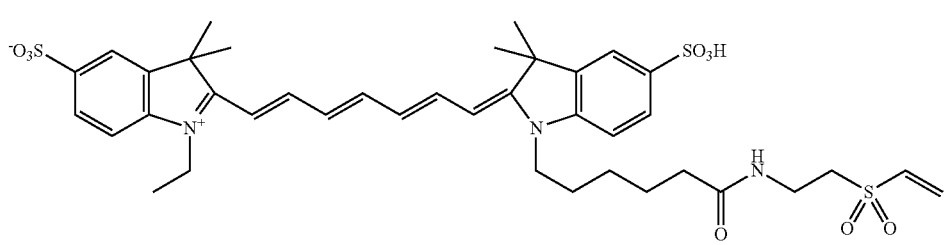

1-3

The compound 10-3 (20.8 mg, 0.0305 mmol, 1 eq) was dissolved in DMF (4 mL) and the temperature was elevated to 55° C. 0.02 mL of pyridine was added to the solution and a solution of DSC (23.6 mg, 0.0921 mmol, 3.02 eq) in DMF (0.3 mL) was dropwise added thereto. The resulting mixture was stirred for one hour, a green solid was precipitated through addition of ethyl acetate was filtered, while washing with ethyl acetate and ether several times. The filtrate was dissolved in DMF (4 mL), 40 mg of Hunig's base was added thereto, a solution of 2-(T-chloroethylsulfonyl)ethyl amine hydrochloride (6.5 mg, 0.0312 mmol, 1.03 eq) dissolved in 0.1 mL of DMF was dropwise added thereto, and the resulting mixture was stirred at ambient temperature for 12 hours or longer. The reaction mixture was extracted in water and methylene chloride (dichloromethane), and distilled under reduced pressured at 35 to 40° C. to remove the solvent. The residue was purified by RP-C18 reverse phase chromatography using 15% acetonitrile aqueous solution as an eluent to obtain a pure compound 1-3 (17.9 mg, 73%).

$R_f$=0.50 (RP-C18, acetonitrile/water 3:7 v/v)

$^1$H NMR (400 MHz, DMSO-$d_6$): δ 8.03 (t, 1H), 7.88-7.60 (m, 7H), 7.29 (dd, 2H, J=3.24 Hz, 3.23 Hz), 6.97 (m, 1H), 6.54 (m, 2H), 6.39-6.22 (m, 4H), 4.10-4.03 (m, 4H), 3.23 (m, 2H), 2.03 (t, 2H, J=7.08 Hz), 1.62-1.12 (m, 23H)

LC/MS, $C_{39}H_{50}N_3O_9S_3^+$, calculated value: 800.27, measured value: 800.32

$\lambda_{abs}$ (water): 748 nm ($\epsilon$=1.464×10$^5$M$^{-1}$ cm$^{-1}$), $\lambda_{fl}$ (water): 790 nm Examples 4 to 15

The compounds of Examples 4 to 15 (compounds 1-4 to 1-15) were prepared using a method similar to that of Examples 1 to 3. Data of the structures of these compounds are given below:

Example 4

Preparation of Compounds 1-4

(1) Compound 6a-2

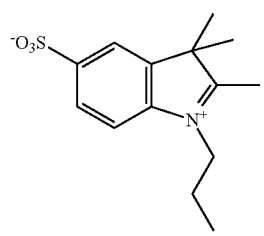

6a-2

(19.81 g, 98%)

$R_f$=0.45 (RP-C18, acetonitrile/water 1:4 v/v)

(2) Compound 9-4

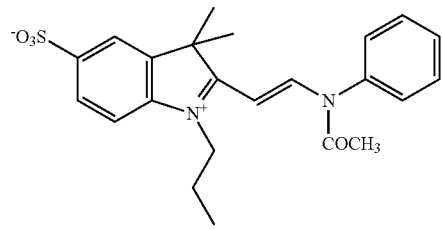

9-4

(10.28 g, 85%)

$R_f$=0.10 (RP-C18, acetonitrile/water 1:4 v/v)

(3) Compound 10-4

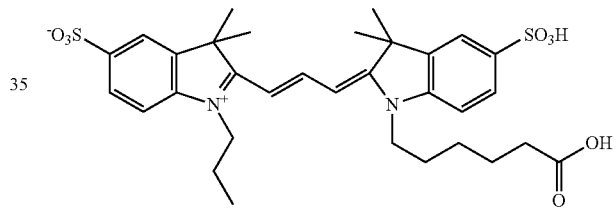

10-4

(3.06 g, 20.6%)

$R_f$=0.49 (RP-C18, acetonitrile/water 3:7 v/v)

$^1$H NMR (300 MHz, DMSO-$d_6$): δ 8.34 (t, 1H, J=13.2 Hz), 7.78 (s, 2H), 7.65 (d, 2H, J=8.04 Hz), 7.39 (m, 2H), 6.56 (dd, 2H, J=13.16 Hz, 13.44 Hz), 4.10 (m, 4H), 1.88 (t, 2H, J=6.88 Hz), 1.77-1.38 (m, 21H), 0.96 (t, 3H, J=7.24 Hz)

LC/MS, $C_{32}H_{39}N_2O_8S_2^-$, calculated value: 643.22, measured value: 643.29

$\lambda_{abs}$ (water): 550 nm, $\lambda_{fl}$ (water): 574 nm (4) Compound 1-4

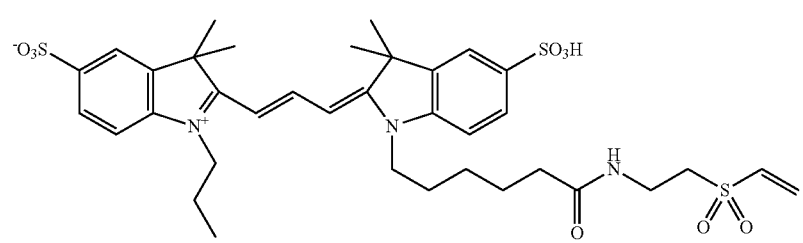

1-4

(39.5 mg, 84%)

$R_f$=0.55 (RP-C18, acetonitrile/water 3:7 v/v)

$^1$H NMR (400 MHz, DMSO-$d_6$): δ 8.35 (t, 1H, J=13.4 Hz), 7.99 (m, 1H), 7.79 (s, 2H), 7.66 (d, 2H, J=7.86 Hz), 7.39 (dd, 2H, J=8.68 Hz, 8.60 Hz), 6.96 (dd, 1H, J=9.90 Hz, 9.96 Hz), 6.51 (t, 2H, J=9.25 Hz), 6.23 (m, 2H), 4.09 (m, 4H), 3.21 (m, 2H), 2.05 (m, 2H), 1.76-1.24 (m, 23H), 0.96 (t, 3H, J=6.99 Hz)

LC/MS, $C_{36}H_{46}N_3O_9S_3^-$, calculated value: 760.24, measured value: 760.30

*$\lambda_{abs}$ (water): 551 nm, $\lambda_{fl}$ (water): 576 nm

Example 5

Preparation of Compounds 1-5

(1) Compound 9-5

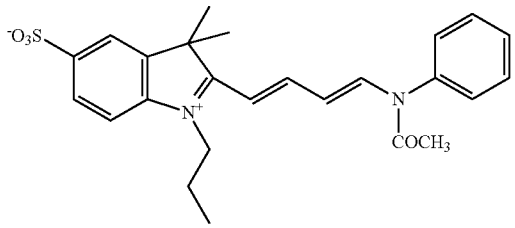

9-5

(9.12 g, 71%)

$R_f$=0.13 (RP-C18, acetonitrile/water 1:4 v/v)

(2) Compound 10-5

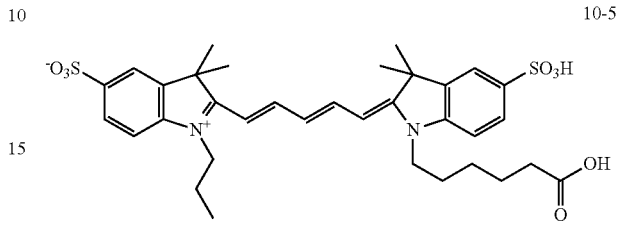

10-5

(2.17 g, 16%)

$R_f$=0.49 (RP-C18, acetonitrile/water 3:7 v/v)

$^1$H NMR (400 MHz, DMSO-$d_6$): δ 8.34 (t, 2H, J=12.8 Hz), 7.79 (s, 2H), 7.61 (d, 2H, J=7.80 Hz), 7.31 (t, 2H, J=9.2 Hz), 6.59 (t, 1H, J=12.1 Hz), 6.30 (dd, 2H, J=3.53 Hz, 3.47 Hz), 4.05 (m, 4H), 1.97 (t, 2H, J=6.96 Hz), 1.72-1.22 (m, 21H), 0.92 (t, 3H, J=7.24 Hz)

LC/MS, $C_{34}H_{41}N_2O_8S_2^-$, calculated value: 669.23, measured value: 669.30

$\lambda_{abs}$ (water): 649 nm, $\lambda_{fl}$ (water): 668 nm (3) Compound 1-5

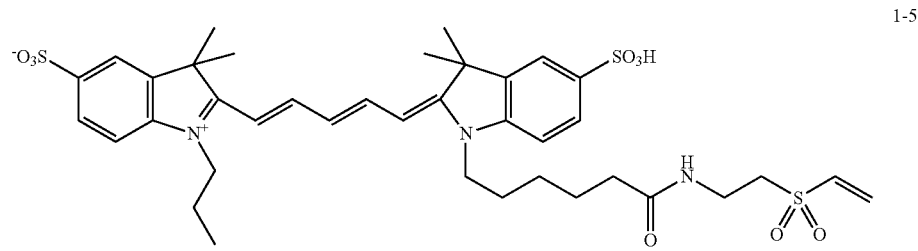

1-5

(43.1 mg, 88.3%)

$R_f$=0.55 (RP-C18, acetonitrile/water 3:7 v/v)

$^1$H NMR (300 MHz, DMSO-$d_6$): δ 8.34 (t, 2H, J=12.6 Hz), 7.97 (t, 1H), 7.80 (s, 2H), 7.62 (d, 2H, J=7.8 Hz), 7.31 (t, 2H), 6.95 (dd, 1H, J=9.88 Hz, 9.96 Hz), 6.58 (t, 1H, J=11.9 Hz), 6.33-6.21 (m, 4H), 4.06 (m, 4H), 3.21 (t, 2H, J=6.88 Hz), 2.03 (t, 2H, J=6.96 Hz), 1.74-1.24 (m, 23H), 0.93 (t, 3H, J=7.24 Hz)

LC/MS, $C_{38}H_{48}N_3O_9S_3^-$, calculated value: 786.26, measured value: 786.34

$\lambda_{abs}$ (water): 649 nm, $\lambda_{fl}$ (water): 672 nm

Example 6

Preparation of Compounds 1-6

(1) Compound 9-6

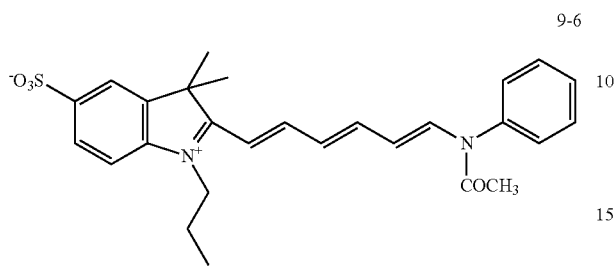

9-6

(5.49 g, 65%)

$R_f$=0.55 (RP-C18, acetonitrile/water 1:2 v/v)

(2) Compound 10-6

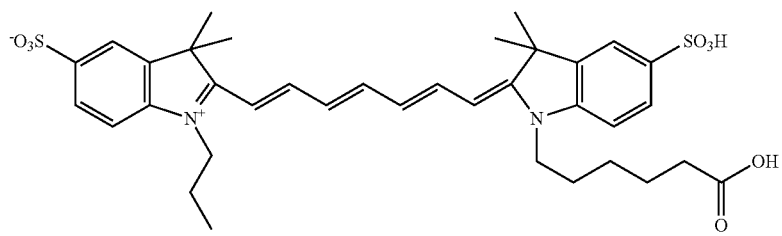

10-6

(2.60 g, 20%)

$R_f$=0.37 (RP-C18, acetonitrile/water 3:7 v/v)

$^1$H NMR (300 MHz, DMSO-$d_6$): δ 7.92-7.73 (m, 5H), 7.62 (d, 2H, J=8.13 Hz), 7.30 (t, 2H, J=7.62 Hz), 6.50 (t, 2H), 6.38 (dd, 2H, J=3.84 Hz, 4.05 Hz), 4.04 (m, 4H), 2.01 (t, 2H, J=6.96 Hz), 1.75-1.23 (m, 21H), 0.94 (t, 3H, J=7.29 Hz)

LC/MS, $C_{36}H_{43}N_2O_8S_2^-$, calculated value: 695.25, measured value: 695.29

$\lambda_{abs}$ (water): 749 nm, $\lambda_{fl}$ (water): 790 nm (3) Compound 1-6

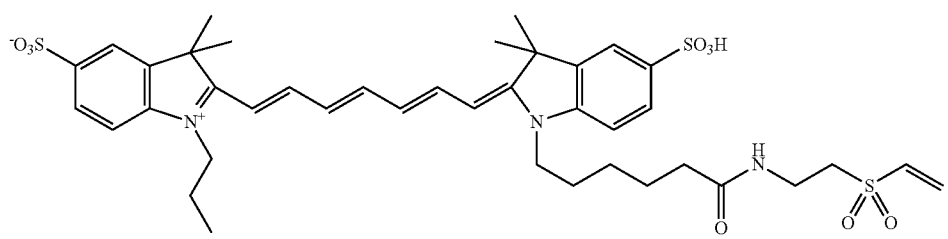

1-6

(35.5 mg, 70%)

$R_f$=0.48 (RP-C18, acetonitrile/water 3:7 v/v)

$^1$H NMR (400 MHz, DMSO-$d_6$): δ 7.98 (m, 1H), 7.87 (t, 2H, J=10.6 Hz), 7.73 (m, 3H), 7.61 (d, 2H, J=8.08 Hz), 7.29 (dd, 2H, J=8.21 Hz, 8.40 Hz), 6.96 (dd, 1H, J=10.1 Hz, 10.1 Hz), 6.54 (t, 2H, J=12.1 Hz), 6.36 (t, 2H, J=14.1 Hz), 6.23 (m,

2H), 4.03 (m, 4H), 3.22 (m, 2H), 2.03 (t, 2H, J=7.26 Hz), 1.74-1.22 (m, 23H), 0.93 (t, 3H, J=7.22 Hz)

LC/MS, $C_{40}H_{50}N_3O_9S_3^-$, calculated value: 812.27, measured value 812.35

$\lambda_{abs}$ (water): 749 nm, $\lambda_{fl}$ (water): 789 nm

Example 7

Preparation of Compounds 1-7

(1) Compound 6a-3

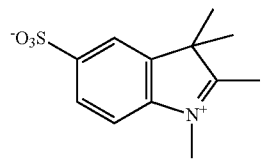

6a-3

(13.45 g, 82%)

$R_f$=0.13 (RP-C18, acetonitrile/water 1:4 v/v)

(2) Compound 9-7

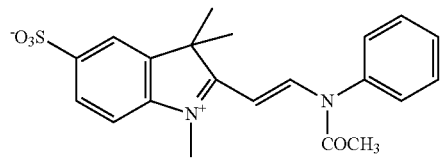

9-7

(6.48 g, 52%)

$R_f$=0.33 (RP-C18, acetonitrile/water 1:4 v/v)

(3) Compound 10-7

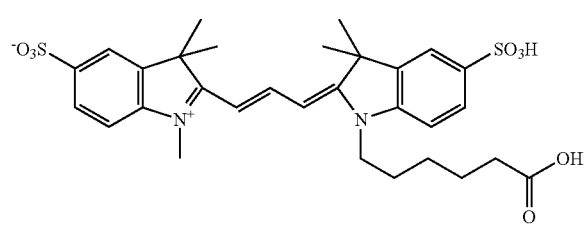

10-7

(0.94 g, 27%)

$R_f$=0.80 (RP-C18, acetonitrile/water 3:7 v/v)

$^1$H NMR (300 MHz, D$_2$O): δ 7.95 (m, 1H), 7.84-7.62 (m, 4H), 7.46 (d, 2H, J=7.89 Hz), 6.51 (d, 2H, J=8.22 Hz), 4.41 (t, 2H, J=8.07 Hz), 3.56 (s, 3H), 1.90 (m, 2H), 1.70-1.24 (m, 18H)

MALDI-TOF M/S, $C_{30}H_{37}N_2O_8S_2^+$, calculated value: 617.2, measured value: 617.53

$\lambda_{abs}$ (water): 546 nm, $\lambda_{fl}$ (water): 570 nm (4) Compound 1-7

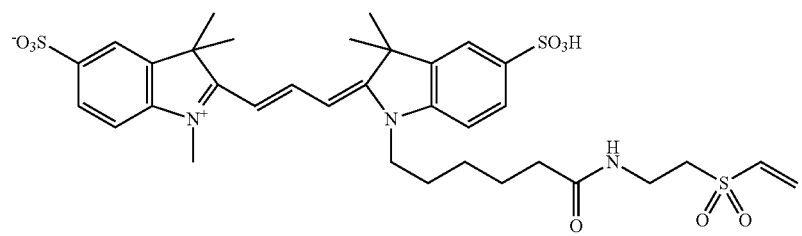

1-7

(37.2 mg, 82%).

$R_f$=0.71 (RP-C18, acetonitrile/water 3:7 v/v)

$^1$H NMR (300 MHz, DMSO-d$_6$): δ 8.31 (t, 1H), 8.06 (t, 1H, J=5.86 Hz), 7.64 (s, 2H), 7.65 (m, 2H), 7.38 (dd, 2H, J=4.32 Hz, 4.36 Hz), 6.97 (dd, 1H, J=9.36 Hz, 9.96 Hz), 6.46 (dd, 2H, J=5.24 Hz, 5.36 Hz), 6.23 (m, 2H), 4.08 (m, 4H), 3.64 (s, 3H), 3.21 (t, 2H, J=6.72 Hz), 2.04 (t, 2H, J=6.84 Hz), 1.68-1.23 (m, 20H)

LC/MS, $C_{34}H_{42}N_3O_9S_3^-$, calculated value: 732.21, measured value: 732.47

$\lambda_{abs}$ (water): 549 nm, $\lambda_{fl}$ (water): 568 nm

Example 8

Preparation of Compound 1-8

(1) Compound 9-8

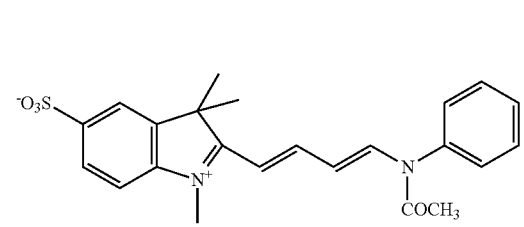

9-8

(2.05 g, 74%)

$R_f$=0.25 (RP-C18, acetonitrile/water 1:4 v/v)

(2) Compound 10-8

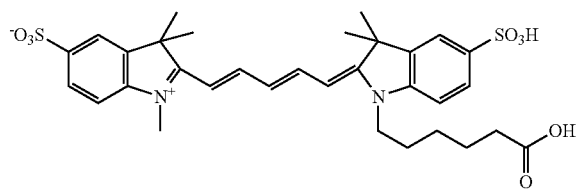

10-8

(0.88 g, 15%)

$R_f$=0.63 (RP-C18, acetonitrile/water 3:7 v/v)

$^1$H NMR (300 MHz, DMSO-$d_6$): δ 7.91 (t, 2H, J=13.7 Hz), 7.74-7.69 (m, 4H), 7.24 (t, 2H, J=8.43 Hz), 6.45 (t, 1H, J=12.5 Hz), 6.16-6.11 (m, 2H), 3.98 (t, 2H, J=5.95 Hz), 3.49 (s, 3H), 2.11 (t, 2H, J=7.06 Hz), 1.73-1.34 (m, 18H)

LC/MS, $C_{32}H_{37}N_2O_8S_2^-$, calculated value: 641.20, measured value: 641.27

$λ_{abs}$ (water): 646 nm, $λ_{fl}$ (water): 666 nm (3) Compound 1-8

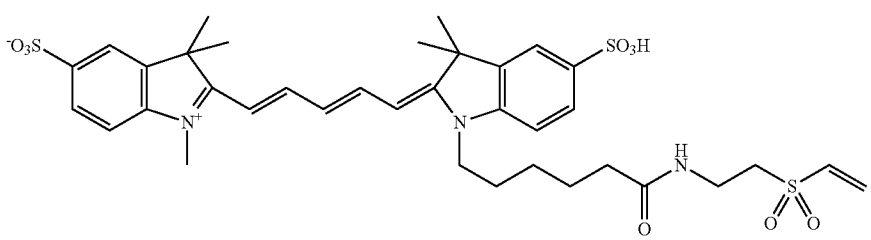

1-8

(38.1 mg, 81%)

$R_f$=0.63 (RP-C18, acetonitrile/water 3:7 v/v)

$^1$H NMR (400 MHz, DMSO-$d_6$): δ 8.34 (t, 2H, J=13.5 Hz), 8.00-7.94 (m, 3H), 7.79 (s, 2H), 7.61 (t, 2H, J=8.04 Hz), 7.30 (dd, 2H, J=3.04 Hz, 3.00 Hz), 6.97 (dd, 1H, J=10.5 Hz, 10.2 Hz), 6.57 (t, 1H, J=12.2 Hz), 6.31-6.21 (m, 4H), 4.06 (m, 2H), 3.58 (s, 3H), 3.21 (t, 2H, J=6.64 Hz), 2.02 (t, 2H, J=7.08 Hz), 1.67-1.24 (m, 20H)

LC/MS, $C_{36}H_{44}N_3O_9S_3^-$, calculated value: 758.22, measured value: 758.47

$λ_{abs}$ (water): 646 nm, $λ_{fl}$ (water): 674 nm

Example 9

Preparation of Compound 1-9

(1) Compound 9-9

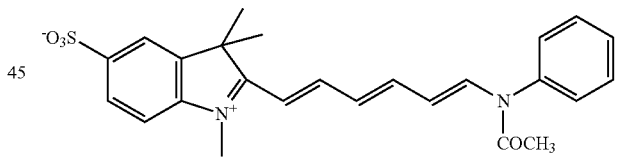

9-9

(11.49 g, 80.9%)

$R_f$=0.83 (RP-C18, acetonitrile/water 1:2 v/v)

(2) Compound 10-9

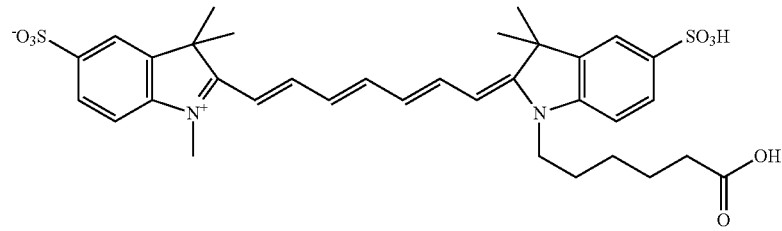

10-9

(1.33 g, 16%)

*$R_f$=0.43 (RP-C18, acetonitrile/water 3:7 v/v)

$^1$H NMR (300 MHz, DMSO-$d_6$): δ 7.80-7.62 (m, 5H), 7.33 (t, 2H, J=13.2 Hz), 7.17 (t, 2H, J=7.32 Hz), 6.34 (t, 2H, 12.2 Hz), 6.06 (dd, 2H, J=5.26 Hz, 5.05 Hz), 3.92 (m, 2H), 3.44 (s, 3H), 2.10 (t, 2H, J=7.45 Hz), 1.90-1.20 (m, 18H)

LC/MS, $C_{34}H_{39}N_2O_8S_2^-$, calculated value: 667.22, measured value: 667.33

$\lambda_{abs}$ (water): 746 nm, $\lambda_{fl}$ (water): 783 nm (3) Compound 1-9

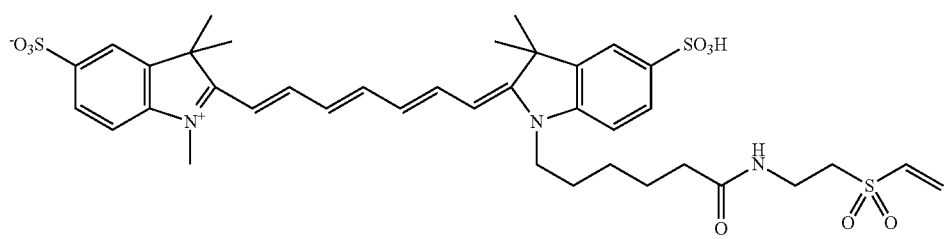

1-9

(40.6 mg, 84%)

$R_f$=0.57 (RP-C18, acetonitrile/water 3:7 v/v)

$^1$H NMR (400 MHz, DMSO-$d_6$): δ 8.00 (m, 1H), 7.88-7.86 (m, 2H), 7.73 (m, 3H), 7.61 (t, 2H, J=6.64 Hz), 7.28 (dd, 2H, J=8.12 Hz, 8.00 Hz), 7.10-6.90 (m, 1H), 6.53-6.49 (m, 2H); 6.34-6.22 (m, 4H), 4.02 (m, 2H), 3.57 (s, 3H), 3.22 (t, 2H), 2.03 (t, 2H), 1.74-1.22 (m, 20H)

LC/MS, $C_{38}H_{46}N_3O_9S_3^-$, calculated value: 784.24, measured value: 784.47

$\lambda_{abs}$ (water): 746 nm, $\lambda_{fl}$ (water): 792 nm

Example 10

Preparation of Compound 1-10

(1) Compound 6a-4

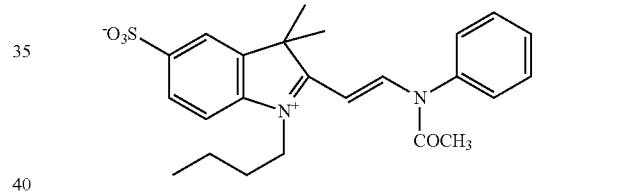

6a-4

(5.65 g, 96%)

$R_f$=0.58 (RP-C18, acetonitrile/water 1:4 v/v)

(2) Compound 9-10

9-10

(1.75 g, 56.1%)

$R_f$=0.08 (RP-C18, acetonitrile/water 1:4 v/v)

(3) Compound 10-10

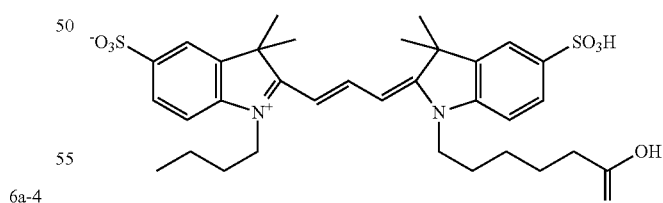

10-10

(1.09 g, 23.3%)

$R_f$=0.61 (RP-C18, acetonitrile/water 3:7 v/v)

$^1$H NMR (400 MHz, DMSO-$d_6$): δ 8.34 (t, 1H, J=13.4 Hz), 7.86 (s, 2H), 7.79 (d, 2H, J=7.72 Hz), 7.38 (d, 2H, J=6.16 Hz), 6.56 (dd, 2H, J=13.6 Hz, 13.5 Hz), 4.11 (m, 4H), 1.92 (t, 2H, J=6.96 Hz), 1.76-1.22 (m, 25H), 0.92 (t, 3H, J=7.2 Hz)

L/C M/S, $C_{33}H_{41}N_2O_8S_2^-$, calculated value: 657.23, measured value: 657.28

$\lambda_{abs}$ (water): 551 nm, $\lambda_{fl}$ (water): 567 nm (4) Compound 1-10

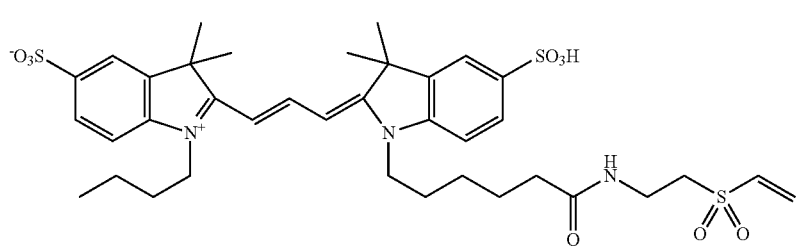

(187.4 mg, 81.9%)

$R_f$=0.60 (RP-C18, acetonitrile/water 3:7 v/v)

$^1$H NMR (400 MHz, DMSO-$d_6$): δ 8.36 (t, 1H), 8.02 (t, 1H), 7.81 (s, 2H), 1.68 (d, 2H), 7.40 (dd, 2H), 6.97 (dd, 1H), 6.53 (dd, 2H), 6.23 (m, 2H), 4.12 (m, 4H), 3.22 (t, 2H), 2.05 (t, 2H), 1.75-1.18 (m, 27H), 0.93 (t, 3H)

LC/MS, $C_{37}H_{48}N_3O_9S_3^-$, calculated value: 774.26, measured value: 774.53

$\lambda_{abs}$ (water): 551 nm ($\epsilon$=1.738×10$^5$ M$^{-1}$ cm$^{-1}$), $\lambda_{fl}$ (water): 568 nm Example 11

Preparation of Compound 1-11

(1) Compound 9-11

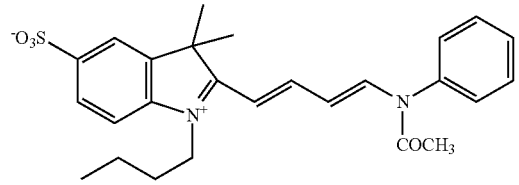

(2.92 g, 88%)

$R_f$=0.08 (RP-C18, acetonitrile/water 1:4 v/v)

(2) Compound 10-11

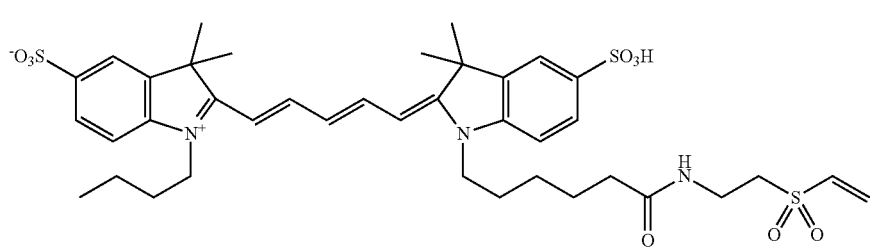

(1.15 g, 23.6%)

$R_f$=0.42 (RP-C18, acetonitrile/water 3:7 v/v)

$^1$H NMR (400 MHz, DMSO-$d_6$): δ 8.34 (t, 2H, J=12.0 Hz), 7.80 (s, 2H), 7.62 (d, 2H, J=7.20 Hz), 7.32 (m, 2H), 6.59 (t, 1H, J=11.5 Hz), 6.31 (m, 2H), 4.08 (m, 4H), 2.04 (t, 2H), 1.77-1.21 (m, 25H), 0.90-0.79 (m, 3H)

LC/MS, $C_{35}H_{43}N_2O_8S_2^-$, calculated value: 683.25, measured value: 683.33

$\lambda_{abs}$ (water): 649 nm, $\lambda_{fl}$ (water): 668 nm (3) Compound 1-11

1-11

(185 mg, 76.9%)

$R_f$=0.51 (RP-C18, acetonitrile/water 3:7 v/v)

$^1$H NMR (400 MHz, DMSO-d$_6$): δ 8.35 (t, 2H, J=12.4 Hz), 8.00 (t, 1H), 7.80 (s, 2H), 7.61 (d, 2H, J=8.32 Hz), 7.30 (dd, 2H, J=4.00 Hz, 4.20 Hz), 6.96 (m, 1H), 6.58 (t, 1H), 6.31-6.21 (m, 4H), 4.07 (m, 4H), 3.22 (t, 2H, J=6.60 Hz), 2.03 (t, 2H, J=7.04 Hz), 1.53-1.22 (m, 27H), 0.91 (t, 3H, J=7.28 Hz)

LC/MS, C$_{39}$H$_{50}$N$_3$O$_9$S$_3^-$, calculated value: 800.27, measured value: 800.36

$\lambda_{abs}$ (water): 649 nm ($\epsilon$=2.024×10$^5$ M$^{-1}$ cm$^{-1}$), $\lambda_{fl}$ (water): 670 nm

Example 12

Preparation of Compound 1-12

(1) Compound 9-12

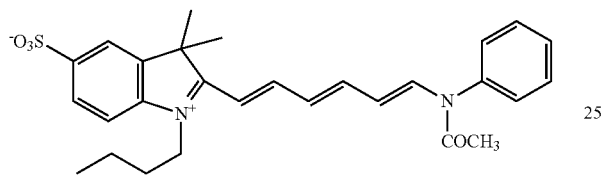

9-12

(2.52 g, 71.8%)
R$_f$=0.42 (RP-C18, acetonitrile/water 1:2 v/v)

(2) Compound 10-12

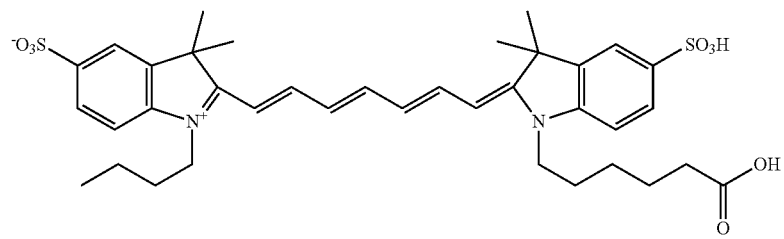

10-12

(1.26 g, 25.0%)
R$_f$=0.35 (RP-C18, acetonitrile/water 3:7 v/v)
$^1$H NMR (400 MHz, DMSO-d$_6$): δ 7.79-7.73 (m, 5H), 7.61 (d, 2H, J=6.84 Hz), 7.29 (dd, 2H, J=3.48 Hz, 3.16 Hz), 6.56 (t, 2H, J=12.1 Hz), 6.36 (d, 2H, J=13.6 Hz), 4.04 (m, 4H), 2.01 (t, 2H), 1.50-1.33 (m, 25H), 0.90 (t, 3H, J=7.16 Hz)

LC/MS, C$_{37}$H$_{45}$N$_2$O$_8$S$_2^-$, calculated value: 709.26, measured value: 709.34

$\lambda_{abs}$ (water): 749 nm, $\lambda_{fl}$ (water): 778 nm (3) Compound 1-12

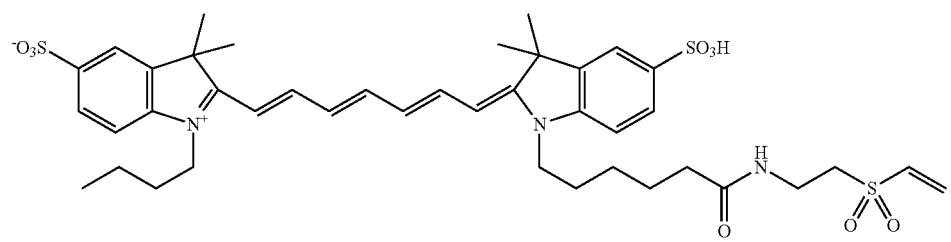

1-12

(171.7 mg, 69.1%)

$R_f$=0.44 (RP-C18, acetonitrile/water 3:7 v/v)

$^1$H NMR (400 MHz, DMSO-$d_6$): δ 8.02-7.72 (m, 6H), 7.63 (d, 2H), 7.28 (m, 2H), 6.98 (dd, 1H), 6.55 (t, 2H), 6.36 (dd, 2H), 6.28-6.22 (m, 2H), 4.05 (m, 4H), 3.23 (m, 2H), 2.02 (t, 2H), 1.70-1.21 (m, 23H), 0.92 (t, 3H)

LC/MS, $C_{41}H_{52}N_3O_9S_3^-$, calculated value: 826.29, measured value: 826.80

$λ_{abs}$ (water): 749 nm (c=1.817×10$^5$M$^{-1}$ cm$^{-1}$), $λ_{fl}$ (water): 779 nm Example 13

Preparation of Compound 1-13

(1) Compound 6b-2

(10.18 g, 64%)

$R_f$=0.13 (RP-C18, acetonitrile/water 1:4 v/v)

(2) Compound 10-13

(1.47 g, 24%)

$R_f$=0.71 (RP-C18, acetonitrile/water 3:7 v/v)

$^1$H NMR (300 MHz, DMSO-$d_6$): δ 8.35 (t, 1H, J=13.5 Hz), 7.79 (s, 2H), 7.68 (d, 2H, J=8.22 Hz), 7.41 (m, 2H), 6.57 (dd, 2H, J=5.00 Hz, 4.78 Hz), 4.18-4.11 (m, 4H), 2.05 (t, 2H), 1.69-0.83 (m, 19H)

LC/MS, $C_{30}H_{35}N_2O_8S_2^-$, calculated value: 615.18, measured value: 615.28

$λ_{abs}$ (water): 549 nm, $λ_{fl}$ (water): 572 nm (3) Compound 1-13

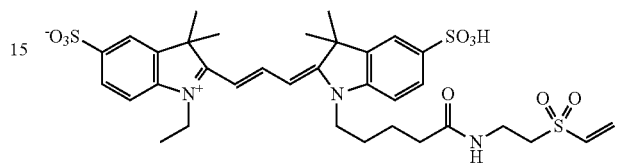

(96.8 mg, 75.8%)

$R_f$=0.70 (RP-C18, acetonitrile/water 3:7 v/v)

$^1$H NMR (400 MHz, DMSO-$d_6$): ε 8.34 (t, 1H, J=13.7 Hz), 8.07 (m, 1H), 7.80 (s, 2H), 7.67 (d, 2H, J=7.60 Hz), 7.39 (dd, 2H, J=3.80 Hz, 3.92 Hz), 6.94 (dd, 1H, J=9.96 Hz, 10.1 Hz), 6.51 (d, 2H, J=13.3 Hz), 6.21 (m, 2H), 4.08 (m, 4H), 3.21 (t, 2H, J=6.72 Hz), 2.04 (t, 2H, J=6.84 Hz), 1.68-1.23 (m, 20H)

LC/MS, $C_{34}H_{44}N_3O_9S_3^+$, calculated value: 734.22, measured value: 734.07

$λ_{abs}$ (water): 549 nm, $λ_{fl}$ (water): 566 nm

Example 14

Preparation of Compound 1-14

(1) Compound 10-14

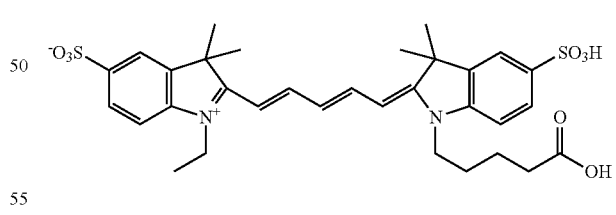

(1.66 g, 25.8%)

$R_f$=0.63 (RP-C18, acetonitrile/water 3:7 v/v) $^1$H NMR (300 MHz, DMSO-$d_6$): δ 7.90 (t, 2H, J=13.1 Hz), 7.74-7.68 (m, 4H), 7.24 (d, 2H, J=8.29 Hz), 6.46 (t, 1H, J=12.8 Hz), 6.17 (dd, 2H, J=10.5 Hz, 10.7 Hz), 3.98 (dd, 4H, J=7.05 Hz, 6.86 Hz), 2.16 (t, 2H, J=7.15 Hz), 1.83-1.23 (m, 18H)

LC/MS, $C_{32}H_{37}N_2O_8S_2^-$, calculated value: 641.2, measured value: 641.0

$λ_{abs}$ (water): 647 nm, $λ_{fl}$ (water): 675 nm (2) Compound 1-14

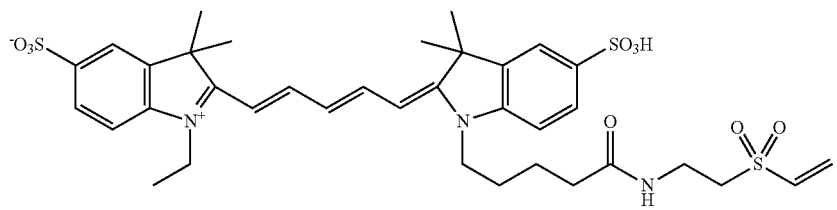

(16.0 mg, 70%)

$R_f$=0.60 (RP-C18, acetonitrile/water 3:7 v/v)

$^1$H NMR (400 MHz, DMSO-$d_6$): δ 8.32 (t, 2H, J=12.9 Hz), 8.04 (t, 1H), 7.80 (s, 2H), 7.62 (t, 2H, J=6.84 Hz), 7.30 (dd, 2H, J=3.56 Hz, 3.52 Hz), 7.00-6.90 (m, 1H), 6.56 (t, 1H), 6.31-6.19 (m, 4H), 4.10 (m, 4H), 3.20 (m, 2H), 2.11 (t, 2H), 1.67-0.95 (m, 21H)

LC/MS, $C_{36}H_{44}N_3O_9S_3^-$, calculated value: 758.22, measured value 758.33

$λ_{abs}$ (water): 647 nm, $λ_{fl}$ (water): 671 nm

Example 15

Preparation of Compound 1-15

(1) Compound 10-15

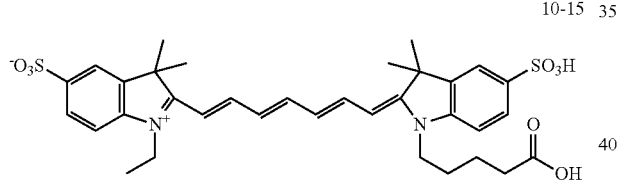

(1.32 g, 20%)

$R_f$=0.52 (RP-C18, acetonitrile/water 3:7 v/v)

$^1$H NMR (300 MHz, DMSO-$d_6$): δ 7.79-7.66 (m, 5H), 7.36 (t, 2H, J=12.1 Hz), 7.21 (d, 2H, J=7.89 Hz), 6.40 (t, 2H, J=12.8 Hz), 6.14 (dd, 2H, J=3.09 Hz, 4.58 Hz), 3.99-3.97 (m, 4H), 2.17 (t, 2H, J=6.23 Hz), 1.83-1.24 (m, 19H)

LC/MS, $C_{34}H_{39}N_2O_8S_2^-$, calculated value: 667.22, measured value: 667.46

$λ_{abs}$ (water): 747 nm, $λ_{fl}$ (water): 784 nm (2) Compound 1-15

$R_f$=0.52 (RP-C18, acetonitrile/water 3:7 v/v)

$^1$H NMR (300 MHz, DMSO-$d_6$): δ 8.08-7.61 (m, 8H), 7.28 (m, 2H), 7.00-6.90 (m, 1H), 6.54 (t, 2H, J=12.9 Hz), 6.36 (dd, 2H, J=5.64 Hz, 3.81 Hz), 6.25-6.19 (m, 2H), 4.10 (m, 4H), 3.22 (m, 2H), 2.13 (m, 2H, J=7.26 Hz), 1.75-1.20 (m, 21H)

LC/MS, $C_{38}H_{46}N_3O_9S_3^-$, calculated value: 784.24, measured value: 784.34

$λ_{abs}$ (water): 747 nm, $λ_{fl}$ (water): 786 nm

Example 16

Preparation of Compound 1-16

(1) Synthesis of Compound 6B-3

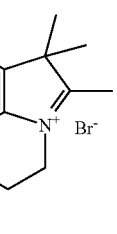

2,3,3-trimethylindolenine (7.96 g, 50 mmol, 1 eq, Aldrich) and 6-bromo-n-hexanoic acid (11.7 g, 60 mmol, 1.2 eq, Aldrich) were heated under reflux in 50 mL of 1,2-dichlorobenzene for 12 hours. The reaction mixture was allowed to cool to ambient temperature, the solvent was removed, and a solid was precipitated through addition of ethyl acetate was filtered and dried under reduced pressure to obtain a pink particulate solid (13.1 g, 73.9%).

$R_f$=0.8 (normal phase, methylene chloride/hexane/methanol 5:1:1 v/v)

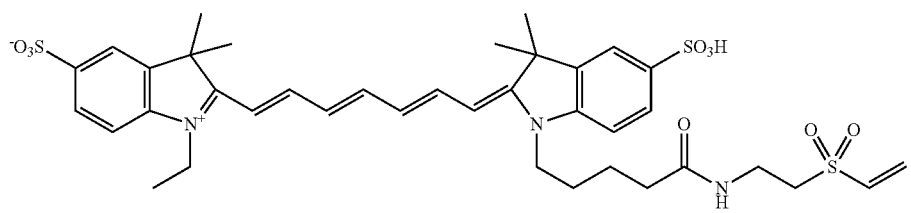

(15.9 mg, 67.3%)

$^1$H NMR (300 MHz, CD$_3$OD): δ 7.91-7.87 (m, 1H), 7.80-7.79 (m, 1H), 7.67-7.69 (m, 2H), 4.56-4.51 (t, J=7.7 Hz, 2H), 2.38-2.33 (t, J=7.7 Hz, 2H), 2.03-1.98 (m, 2H), 1.80-1.52 (m, 10H)

(2) Synthesis of Compound 9-13

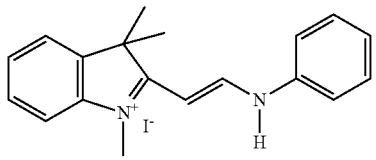
9-13

1,2,3,3-tetramethyl-3H-indoliumiodide (2.00 g, 6.65 mmol, 1 eq, Aldrich) and DPF (1.34 g, 6.863 mmol, 1.03 eq, TCI) were dissolved in 25 mL of acetic acid and the resulting mixture was heated under reflux for one hour. The reaction mixture was allowed to cool to ambient temperature, filtered and recrystallized two or three times in a solution of ethanol and ether. The resulting orange particles were filtered and dried under reduced pressure (2.31 g, 78%).

$R_f$=0.55 (normal phase, methylene chloride/hexane/methanol 5:1:1 v/v)

$^1$H NMR (400 MHz, DMSO-d$_6$): δ 9.27-9.22 (d, J=13.8 Hz, 1H), 7.75-7.49 (m, 9H), 5.62-5.59 (d, J=13.8 Hz, 1H), 3.92 (s, 3H), 2.14 (s, 3H), 1.83 (s, 6H), 1.71 (s, 3H)

(3) Synthesis of Compound 10-16

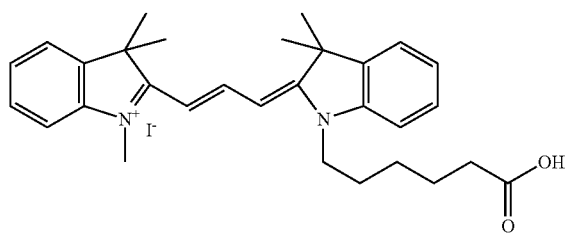
10-16

The compound 9-13 (2.97 g, 8.4 mmol, 1 eq) and the compound 6b-3 (3.75 g, 8.4 mmol, 1 eq) were dissolved in a solution consisting of 300 mL of ethanol and 3 mL of triethylamine and the resulting solution was heated under reflux for 30 minutes. The reaction mixture was allowed to cool to ambient temperature, distilled under reduced pressure and dried. The resulting product was purified by normal chromatography using a mixed eluent of dichloromethane, methanol and hexane (5:1:1) to obtain a pure compound 10-16 (2.36 g, 48%).

$R_f$=0.67 (normal phase, methylene chloride/hexane/methanol 5:1:1 v/v)

$^1$H NMR (400 MHz, DMSO-d$_6$): δ 8.37-8.30 (dd, J=11.8 Hz, 14.5 Hz, 1H), 7.65-7.63 (d, J=6.5 Hz, 2H), 7.46-7.36 (m, 4H), 7.29-7.24 (m, 2H), 6.54-6.51 (d, J=13.3 Hz, 2H), 4.09 (m, 2H), 3.64 (s, 3H), 2.32-2.28 (t, 2H), 1.69-1.42 (m, 18H)

LC/MS, C$_{30}$H$_{37}$N$_2$O$_2^+$, calculated value: 457.28, measured value: 457.8

λ$_{abs}$ (methanol): 546 nm, λ$_{fl}$ (methanol): 564 nm (4) Synthesis of Compound 1-16

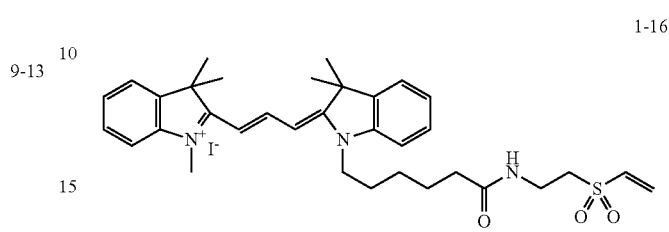
1-16

A solution of CDI (240 mg, 1.5 mmol, 1.5 eq) in DMF (2.5 mL) was added dropwise to a solution of the compound 10-16 (460 mg, 1 mmol, 1 eq) in DMF (5 mL). The resulting mixture was stirred for 30 minutes, 160 mg of Hunig's base was added thereto, a solution of 2-(2'-chloroethylsulfonyl)ethylamine hydrochloride (210 mg, 1 mmol, 1 eq) in 2.5 mL of DMF was added dropwise thereto, and the resulting mixture was stirred at ambient temperature for 24 hours. A solid was precipitated through addition of ether, filtered and purified by normal chromatography using a mixed eluent of dichloromethane, methanol and hexane (5:1:1) to obtain a pure compound 1-16 (0.37 g, 52%).

$R_f$=0.68 (normal phase, methylene chloride/hexane/methanol 5:1:1 v/v)

$^1$H NMR (300 MHz, DMSO-d$_6$): δ 8.31 (t, 1H), 8.06 (t, J=5.86 Hz, 1H), 7.64 (d, J=7.36 Hz, 2H), 7.44 (m, 4H), 7.30 (m, 2H), 6.97 (dd, J=9.93 Hz, 9.91 Hz, 1H), 6.48 (d, J=13.5 Hz, 2H), 6.25 (m, 2H), 4.11-4.07 (m, 2H), 3.65 (s, 3H), 3.22 (t, J=6.58 Hz, 2H), 2.06 (t, J=7.04 Hz, 2H), 1.69-1.42 (m, 20H)

LC/MS, C$_{34}$H$_{44}$N$_3$O$_3$S$^+$, calculated value: 574.31, measured value: 574.22

λ$_{abs}$ (methanol): 546 nm, λ$_{fl}$ (methanol): 564 nm

Example 17

Preparation of Compound 1-17

(1) Synthesis of Compound 9-14

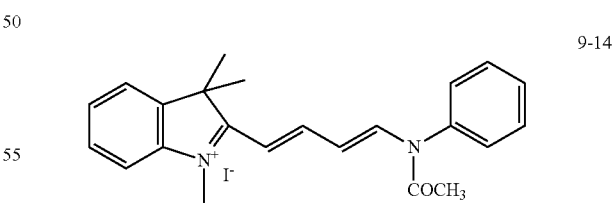
9-14

1,2,3,3-tetramethyl-3H-indoliumiodide (1 g, 3.865 mmol, 1 eq) and MDH (1.106 g, 3.672 mmol, 0.95 eq, TCI) were dissolved in a solution consisting of 5 mL of acetic acid and 5 mL of anhydrous acetic acid, and the resulting mixture was heated under reflux for four hours. The reaction mixture was allowed to cool to ambient temperature, the solvent was removed, and a solid was precipitated by addition of ethyl acetate, filtered, washed with n-butanol several times and dried under reduced pressure (1.56 g, 90%).

$R_f$=0.60 (normal phase, methylene chloride/methanol 5:1 v/v)

$^1$H NMR (400 MHz, DMSO-d$_6$): δ 8.87-8.83 (d, J=13.2 Hz, 1H), 8.47-8.44 (t, J=14.9, 1H), 7.75-7.49 (m, 9H), 6.83-6.79 (d, J=14.9, 1H), 5.62-5.59 (dt, J=12.9 Hz, 11.5 Hz, 1H), 3.76 (s, 3H), 2.15 (s, 3H), 1.97 (s, 6H), 1.66 (s, 3H)

(2) Synthesis of Compound 10-17

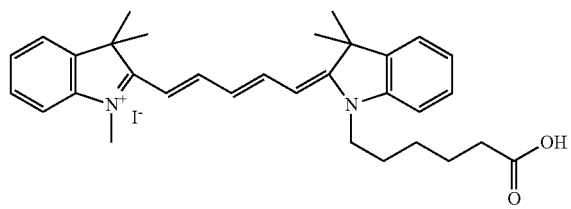

10-17

The compound 9-14 (1 g, 4.49 mmol, 1 eq) was reacted with the compound 6b-3 (1.23 g, 10 mmol, 1.35 eq) in the presence of a mixed solvent of 15 mL of anhydrous acetic acid and 15 mL of pyridine at 110° C. for 4 hours. The reaction mixture was allowed to cool to ambient temperature, and a blue solid was precipitated through addition of ethyl acetate, filtered and dried under reduced pressure. The resulting product was purified by normal chromatography using a mixed eluent of dichloromethane, methanol and hexane (5:1:1) to obtain a pure compound 10-17 (0.35 g, 13%).

$R_f$=0.70 (normal phase, methylene chloride/hexane/methanol 5:1:1 v/v)

$^1$H NMR (400 MHz, DMSO-d$_6$): δ 8.34-8.27 (t, J=14 Hz, 2H), 7.60-7.58 (d, J=8 Hz, 2H), 7.37-7.36 (m, 4H), 7.23 (m, 2H), 6.57-6.51 (t, J=12 Hz, 1H), 6.30-6.22 (dd, J=12 Hz, 14 Hz, 2H), 4.07 (bt, 2H), 3.65 (s, 3H), 2.18-2.15 (t, J=12 Hz, 2H), 1.95-1.91 (m, 2H), 1.66-1.30 (m, 16H)

LC/MS, C$_{32}$H$_{39}$N$_2$O$_2^+$, calculated value: 483.3, measured value: 483.11

λ$_{abs}$ (methanol): 641 nm, λ$_{em}$ (methanol): 678 nm (3) Synthesis of Compound 1-17

A solution of CDI (73 mg, 0.45 mmol, 1.5 eq) in DMF 0.8 mL was added dropwise to a solution of the compound 10-17 (150 mg, 0.3 mmol, 1 eq) in DMF 3.5 mL. The resulting mixture was stirred for 30 minutes, 49 mg of Hunig's base was added dropwise thereto, a solution of 2-(2'-chloroethyl-sulfonyl)ethylamine hydrochloride (63 mg, 0.3 mmol, 1 eq) in 0.8 mL of DMF was added dropwise thereto and the resulting mixture was stirred at ambient temperature for 24 hours. A solid was precipitated through addition of ether and was purified by normal chromatography using a mixed eluent of dichloromethane, methanol and hexane (5:1:1) to obtain a pure compound 1-17 (0.106 g, 49%).

$R_f$=0.67 (normal phase, methylene chloride/hexane/methanol 5:1:1 v/v)

$^1$H NMR (400 MHz, DMSO-d$_6$): δ 8.31 (t, J=13 Hz, 2H), 8.02 (m, 1H), 7.60 (d, J=7.28 Hz, 2H), 7.36 (d, J=4.48 Hz, 4H), 7.22 (m, 2H), 6.96 (dd, J=10.0 Hz, 9.96 Hz, 1H), 6.55 (t, J=12.2 Hz, 1H), 6.24 (m, 4H), 4.06 (m, 2H), 3.68 (s, 3H), 3.20 (t, J=6.68 Hz, 2H), 2.03 (t, J=7.24 Hz, 2H), 1.66-1.20 (m, 20H)

LC/MS, C$_{36}$H$_{46}$N$_3$O$_3$S$^+$, calculated value: 600.33, measured value: 600.12.

λ$_{abs}$ (water): 641 nm, λ$_{fl}$ (water): 678 nm

Example 18

Preparation of Compound 1-18

(1) Synthesis of compound 9-15

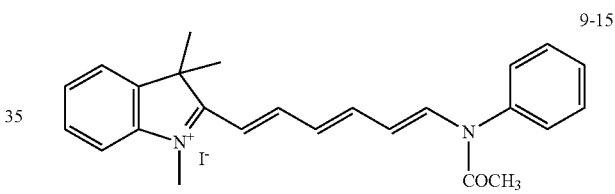

9-15

1,2,3,3-tetramethyl-3H-indoliumiodide (6.626 g, 22 mmol, 1 eq) and GDH (6.265 g, 22 mmol, 1 eq, TCI) were dissolved in 16 mL of anhydrous acetic acid and the resulting solution was allowed to react at 100° C. for one hour. The reaction mixture was allowed to cool to ambient temperature, a solid was precipitated through addition of distilled water and was purified, and the residue was washed several times with distilled water and dried under reduced pressure (5.88 g, 54%).

$R_f$=0.7 (normal phase, methylene chloride/methanol 5:1 v/v)

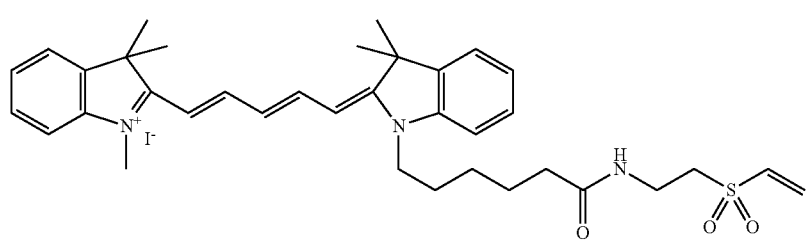

1-17

$^1$H NMR (400 MHz, CDCl$_3$): δ 8.19-8.15 (d, J=13.7 Hz, 1H), 7.84-6.89 (m, 13H), 5.45-5.39 (dt, J=13.4 Hz, 11.7 Hz, 1H), 4.2 (s, 3H), 1.92 (s, 3H), 1.72 (s, 6H), 1.64 (s, 3H)

(2) Synthesis of Compound 10-18

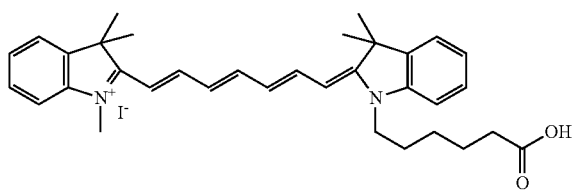

10-18

The compound 9-15 (0.5 g, 1 mmol, 1 eq) and the compound 6b-3 (3.54 g, 1 mmol, 1 eq) were dissolved in 7 mL of pyridine and the resulting solution was stirred at 40° C. for 30 minutes. The reaction mixture was allowed to cool to ambient temperature and the solvent was removed by distillation under reduced pressure. The residue was purified by normal chromatography using a mixed eluent of dichloromethane, methanol, hexane (5:1:1) to obtain a pure compound 10-18. (0.175 g, 28%)

R$_f$=0.88 (normal phase, methylene chloride/methanol 5:1 v/v)

$^1$H NMR (400 MHz, CDCl$_3$): δ 7.87-7.74 (m, 3H), 7.58-7.55 (d, J=9.0 Hz, 2H), 7.40-7.33 (m, 4H), 7.25-7.21 (m, 2H), 6.55-6.49 (m, 2H), 6.35-6.30 (d, J=13.9 Hz, 2H), 4.04-4.02 (m, 2H), 3.58 (s, 3H), 2.22-2.17 (t, J=15 Hz, 2H), 1.67-1.26 (m, 18H)

LC/MS, C$_{34}$H$_{41}$N$_2$O$_2$$^+$, calculated value: 509.32, measured value: 509.25

λ$_{abs}$ (methanol): 740 nm, λ$_{fl}$ (methanol): 775 nm (3) Synthesis of Compound 1-18

The compound 10-18 (153 mg, 0.3 mmol, 1 eq) was dissolved in DMF (3.5 mL) and a solution of CDI (73 mg, 0.45 mmol, 1.5 eq) in DMF (0.8 mL) was added dropwise to the solution. The resulting mixture was stirred for 30 minutes, 49 mg of Hunig's base was added dropwise thereto, a solution of 2-(2'-chloroethylsulfonyl)ethylamine hydrochloride (63 mg, 0.3 mmol, 1 eq) in 0.8 mL of DMF was added dropwise thereto, and the resulting mixture was stirred at ambient temperature for 24 hours. A solid was precipitated through addition of ether, filtered and purified by normal chromatography using a mixed eluent of dichloromethane, methanol, hexane (5:1:1) to obtain a pure compound 1-18 (0.114 g, 52%).

R$_f$=0.81 (normal phase, methylene chloride/methanol 5:1 v/v)

$^1$H NMR (400 MHz, CDCl$_3$): δ 8.03 (t, 1H), 7.87-7.75 (m, 3H), 7.57 (dd, J=2.19 Hz, 2.31 Hz, 2H), 7.38 (m, 4H), 7.22 (m, 2H), 6.97 (dd, J=9.9 Hz, 9.9 Hz, 1H), 6.52 (m, 2H), 6.35-6.22 (m, 4H), 4.03 (m, 2H), 3.58 (s, 3H), 3.21 (m, 2H), 2.05 (t, J=7.2 Hz, 2H), 1.67-1.26 (m, 20H)

LC/MS, C$_{38}$H$_{48}$N$_3$O$_3$S$^+$, calculated value: 626.34, measured value: 626.38

λ$_{abs}$ (methanol): 741 nm, λ$_{fl}$ (methanol): 773 nm

Examples 19 to 21

The compounds (compounds 1-19 to 21) of examples 19 to 21 were prepared in a manner similar to that used in Examples 1 to 3. The data showing structures of these compounds are given below:

Example 19

Preparation of Compound 1-19

(1) Compound 9-16

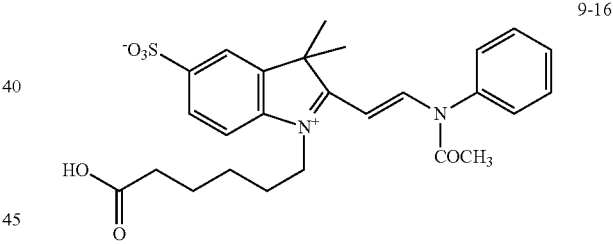

9-16

(1.83 g, 73.3%)

R$_f$=0.05 (RP-C18, acetonitrile/water 1:4 v/v)

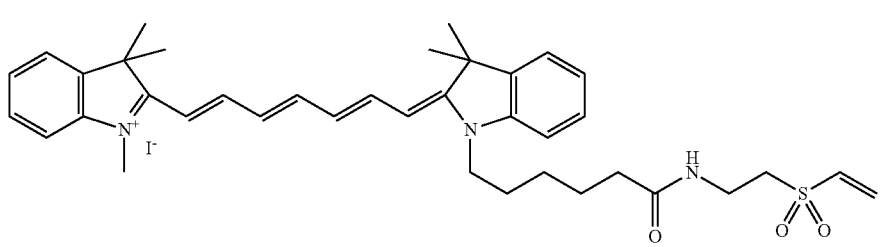

1-18

(2) Compound 10-19

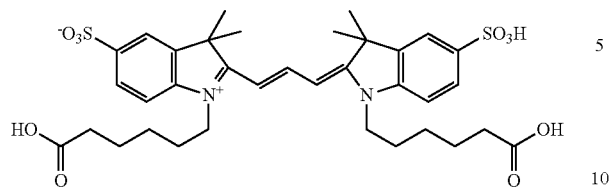

10-19

(0.63 g, 17.5%)

$R_f$=0.40 (RP-C18, acetonitrile/water 3:7 v/v)

$^1$H NMR (300 MHz, DMSO-$d_6$): δ 8.35 (t, 1H, J=12.2 Hz), 7.79 (s, 2H), 7.65 (d, 2H, J=8.37 Hz), 7.39 (d, 2H, J=8.27 Hz), 6.50 (d, 2H, J=13.1 Hz), 4.10 (m, 4H), 2.08 (t, 4H), 1.80-1.20 (m, 24H)

LC/MS, $C_{35}H_{43}N_2O_{10}S_2^-$, calculated value: 715.24, measured value: 715.18

$\lambda_{abs}$ (water): 551 nm, $\lambda_{fl}$ (water): 569 nm (3) Compound 1-19

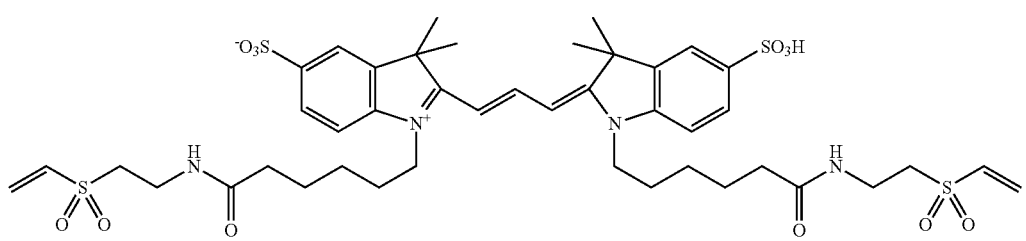

1-19

(98.7 mg, 51.9%)

$R_f$=0.45 (RP-C18, acetonitrile/water 3:7 v/v)

$^1$H NMR (300 MHz, DMSO-$d_6$): δ 8.30 (t, 1H, J=13.5 Hz), 8.06-8.00 (m, 2H), 7.80 (s, 2H), 7.66 (d, 2H, J=8.22 Hz), 7.39 (d, 2H, J=8.19 Hz), 6.97 (dd, 2H, J=9.87 Hz, 9.84 Hz), 6.50 (d, 2H, J=13.3 Hz), 6.24 (m, 4H), 4.11 (m, 4H), 3.22 (t, 2H, J=6.42 Hz), 3.09 (m, 2H), 2.06 (m, 4H), 1.70-1.14 (m, 28H)

LC/MS, $C_{43}H_{57}N_4O_{12}S_4^-$, calculated value: 949.29, measured value: 949.32

$\lambda_{abs}$ (water): 551 nm, $\lambda_{fl}$ (water): 571 nm

Example 20

Preparation of Compound 1-20

(1) Compound 9-17

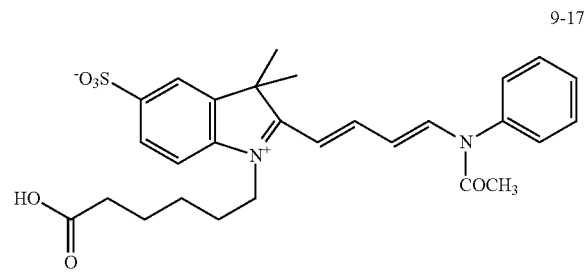

9-17

(3.96 g, 75.4%)

$R_f$=0.05 (RP-C18, acetonitrile/water 1:4 v/v)

(2) Synthesis of Compound 10-20

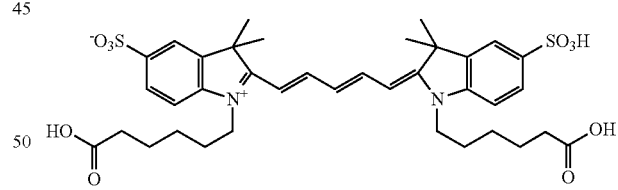

10-20

(1.15 g, 20.6%)

$R_f$=0.35 (RP-C18, acetonitrile/water 3:7 v/v)

$^1$H NMR (300 MHz, DMSO-$d_6$): δ 8.34 (t, 2H, J=12.9 Hz), 7.79 (s, 2H), 7.61 (d, 2H, J=8.13 Hz), 7.30 (d, 2H, J=8.28 Hz), 6.64 (t, 1H, J=11.9 Hz), 6.27 (d, 2H, J=13.8 Hz), 4.06 (m, 4H), 1.99 (t, 4H, J=6.81 Hz), 1.80-1.23 (m, 24H)

LC/MS, $C_{37}H_{45}N_2O_{10}S_2^-$, calculated value: 741.25, measured value: 741.36

$\lambda_{abs}$ (water): 649 nm, $\lambda_{fl}$ (water): 674 nm (3) Compound 1-20
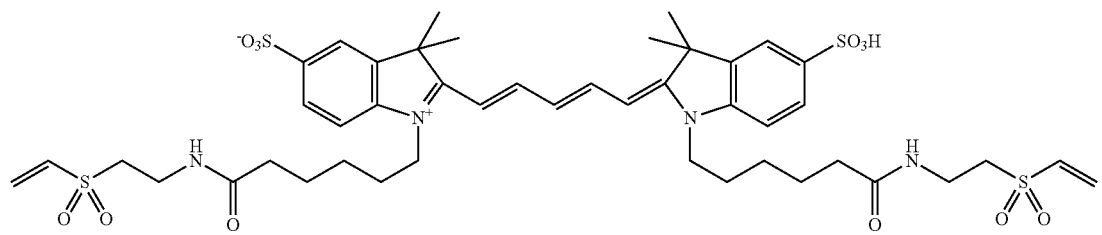
(47.1 mg, 48.2%)
$R_f$=0.42 (RP-C18, acetonitrile/water 3:7 v/v)
$^1$H NMR (400 MHz, DMSO-$d_6$): δ 8.35 (t, 2H, J=13.1 Hz), 8.19-7.99 (m, 2H), 7.80 (s, 2H), 7.61 (d, 2H, J=8.20 Hz), 7.31 (d, 2H, J=8.28 Hz), 6.97 (dd, 2H, J=10.0 Hz, 9.96 Hz), 6.61 (t, 1H, J=12.4 Hz), 6.31-6.21 (m, 4H), 4.07 (m, 4H), 3.22 (m, 2H), 3.13 (m, 2H), 2.18 (t, 2H, J=7.20 Hz), 2.03 (t, 2H, J=7.28 Hz), 1.67-1.20 (m, 28H)
LC/MS, $C_{45}H_{59}N_4O_{12}S_4^-$, calculated value: 975.3, measured value: 975.47
$\lambda_{abs}$ (water): 649 nm, $\lambda_{fl}$ (water): 675 nm
Example 21
Preparation of Compound 1-21
(1) Compound 9-18
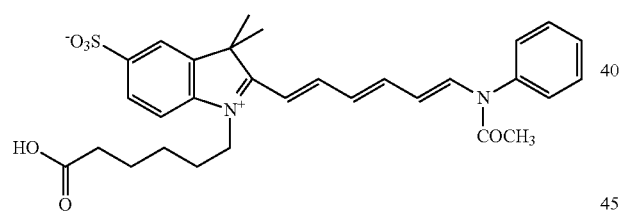
(5.82 g, 99%)
$R_f$=0.3 (RP-C18, acetonitrile/water 1:2 v/v)
(2) Compound 10-21
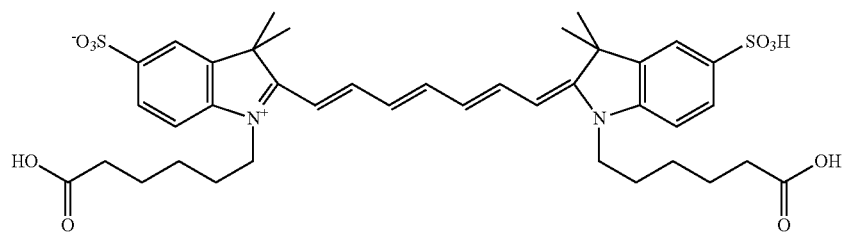
(1.26 g, 33%)

$R_f$=0.32 (RP-C18, acetonitrile/water 3:7 v/v)

$^1$H NMR (300 MHz, DMSO-$d_6$): δ 7.70-7.62 (m, 6H), 7.28 (t, 1H, J=12.8 Hz), 7.14 (d, 2H, J=8.38 Hz), 6.28 (t, 2H, J=12.6 Hz), 6.02 (d, 2H, J=13.6 Hz), 3.90 (m, 4H), 2.12 (t, 4H, J=7.28 Hz), 1.69-1.31 (m, 24H)

LC/MS, $C_{39}H_{47}N_2O_{10}S_2^-$, calculated value: 767.27, measured value: 767.44

$\lambda_{abs}$ (water): 749 nm, $\lambda_{fl}$ (water): 786 nm (3) Compound 1-21

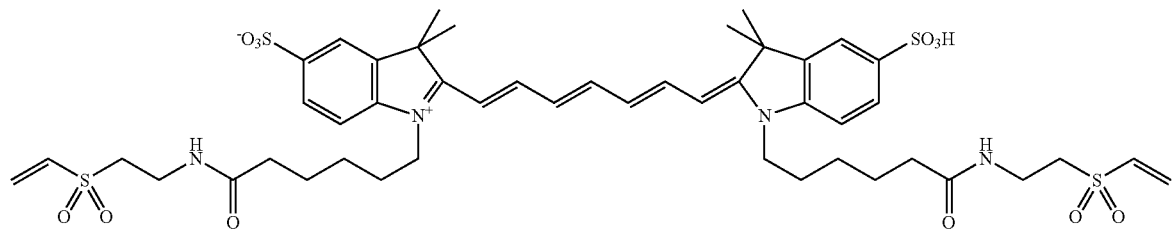

1-21

(42.3 mg, 42.2%)

$R_f$=0.38 (RP-C18, acetonitrile/water 3:7 v/v)

$^1$H NMR (300 MHz, DMSO-$d_6$): δ 8.01 (t, 2H, J=5.68 Hz), 7.86 (t, 2H, J=13.1 Hz), 7.75-7.73 (m, 3H), 7.61 (d, 2H, J=8.20 Hz), 7.28 (d, 2H, J=8.48 Hz), 6.97 (dd, 2H, J=9.96 Hz, 9.92 Hz), 6.54 (t, 2H, J=11.9 Hz), 6.34 (d, 2H, J=13.6 Hz), 6.26-6.22 (m, 4H), 4.11 (m, 4H), 3.21 (t, 4H, J=6.80 Hz), 2.03 (t, 4H, J=7.24 Hz), 1.62-1.23 (m, 28H)

LC/MS, $C_{47}H_{61}N_4O_{12}S_4^-$, calculated value: 1001.32, measured value: 1001.50

$\lambda_{abs}$ (water): 750 nm, $\lambda_{fl}$ (water): 792 nm

Example 22

Testing of Binding Force to Amine Compound

A dilution of 0.1306 μmol of benzyl amine (molecular weight: 107.16, Aldrich) in 10 μl of DMF was added to a 0.1M phosphate buffer solution (pH 5, 20 μl), and 1 μl of a solution of the compound 1-16 (1 mg) in DMF was mixed with the resulting solution. Similarly, a solution of benzyl amine and the compound 1-16 was prepared using the phosphate buffer solution (pH 6, 7, 7.5, 8, 8.5, 9, 9.5 and 10) and the resulting solution was allowed to react at 40° C. for 30 minutes. It is estimated that reaction of the benzyl amine with the compound 1-16 causes production of a compound having the structure represented by Formula 13 below:

After reaction, retention time (RT) of benzyl amine, the compound 1-16 and the product (compound 13) were confirmed by HPLC to obtain a reaction yield. At this time, methanol was used as a mobile phase, flow rate was 2.5 mL/min and analysis time was 80 minutes, and multi-scanning was carried out at wavelengths of 254, 365, 450, 550 and 650 nm. FIG. 1 shows absorbance at a wavelength of 550 nm. In FIG. 1, "■" is a value analyzed from the reaction product stored at 4° C. for one day, and "●" is a value obtained from the reaction product 7 days after the afore-mentioned analysis. As can be seen from FIG. 1, the reaction yield is 60% or higher in the range of pH 8.5 to 9.0, and the reaction yield is 80% or higher in the range of pH 8.5 to 9.0, since the reaction is slow even at a low temperature for a long time. Accordingly, the compound 1-16 of the present invention exhibits superior stability and considerably excellent binding force to the amine compound.

Example 23

Protein Staining Test (1)

Each vial of one pack of Amershame™ LMW calibration kit (17-0446-01) for SDS electrophoresis commercially available from GE healthcare Co., Ltd. contained six kinds of marker proteins (576 μg), so-called, phosphorylase b (97 kD, 67 μg), albumin (66 kD, 83 μg), ovalbumin (45 kD, 147 μg), carbonic anhydrase (30 kD, 83 μg), a trypsin inhibitor (20.1 kD, 80 μg), and α-lactalbumin (14.4 kD, 116 μg).

A phosphate buffer solution (250 μl, 0.1 M) was added to one vial containing the marker proteins at ambient temperature (20° C.) and was aliquoted in an amount of 25 μl to four e-tubes (25 μg protein/25 μl buffer, 6.9×10$^{-5}$ μmol in 25 μl buffer solution).

The compound 1-1 (1 mg) was dissolved in 100 μl of DMF, 1 μl of the solution was placed in the afore-mentioned e-tube, and the resulting mixture was homogeneously mixed using a vortex shaker and a centrifuge. The e-tube was placed in a heating block set to 30° C. and the reaction was proceeded.

(13)

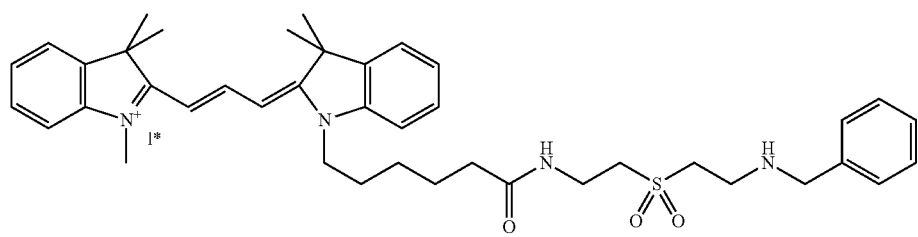

After one hour, one e-tube was collected and stored at −20° C. The reaction of one e-tube was finished after one, two and 16 hours. Finally, the reaction times were adjusted to one, two, four and 20 hours.

In addition, the solution of the compound 1-1 was collected in an amount of 0.25 µl, and reacted in the same manner as in the reaction of the solution of 1 µl.

Figure 2A:
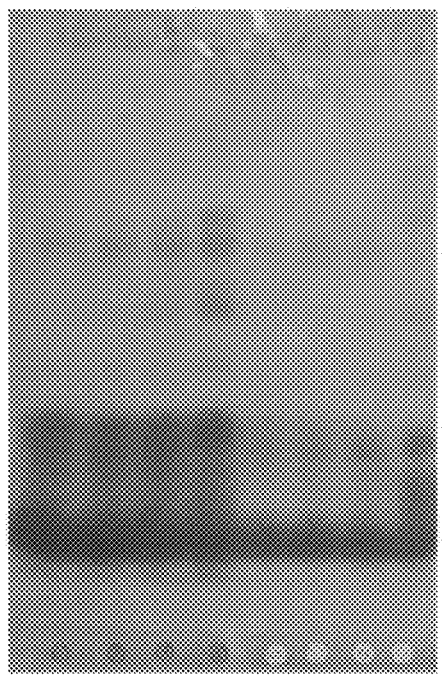
FIG. 2A is an image wherein proteins, which were labeled in Example 23 and subjected to development by gel electrophoresis, were observed by the naked eye.
Figure 2B:
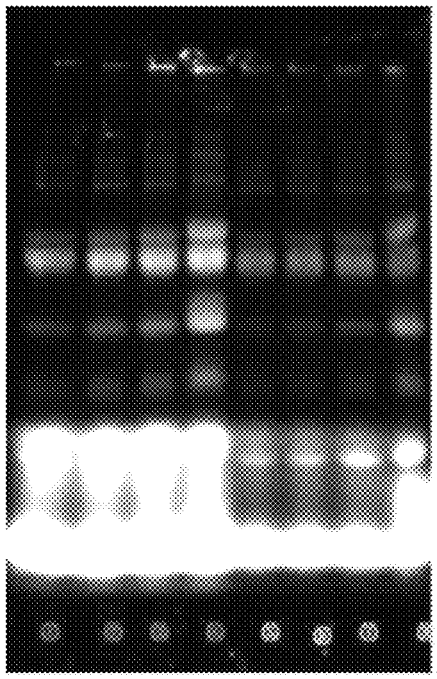
FIG. 2B is a fluorescence image of the proteins.

The reaction product of the solution (1 µl) of the compound 1-1 and the reaction product of the solution (0.25 µl) of the compound 1-1 were loaded in an amount of 15 µA and separated via gel electrophoresis. The results thus obtained are shown in FIGS. 2A and 2B. Electrophoresis was carried out at 125V for two hours.

FIG. 2A is an image observed by the naked eye and FIG. 2B is a fluorescent image. In FIG. 2, ① to ④ are obtained from 1 µl of a dye solution and ⑤ to ⑧ are obtained from 0.25 µl of a dye solution. As can be seen from FIG. 2, as an amount of the compound used increases, protein lanes appear clearer, and as staining time increases, the staining is more efficient and various proteins are homogeneously stained.

Example 24

Protein Staining Test (2)

Phosphate buffer solutions (pH 5, 6, 7, 7.5, 8, 8.5, 9 and 10) were prepared, the reaction was carried out using the same marker proteins and the same compound (compound I-1) as in example 23, and using all of the dye compound solutions in an amount of 0.5 µl for 2 hours.

Figure 3A:
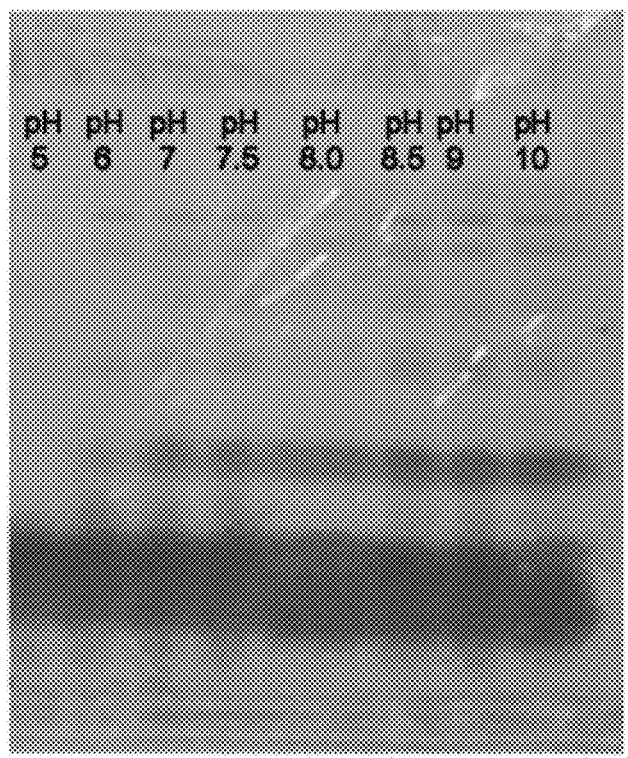
FIG. 3A is an image wherein proteins, which were labeled in Example 24 and subjected to development by gel electrophoresis, were observed by the naked eye.
Figure 3B:
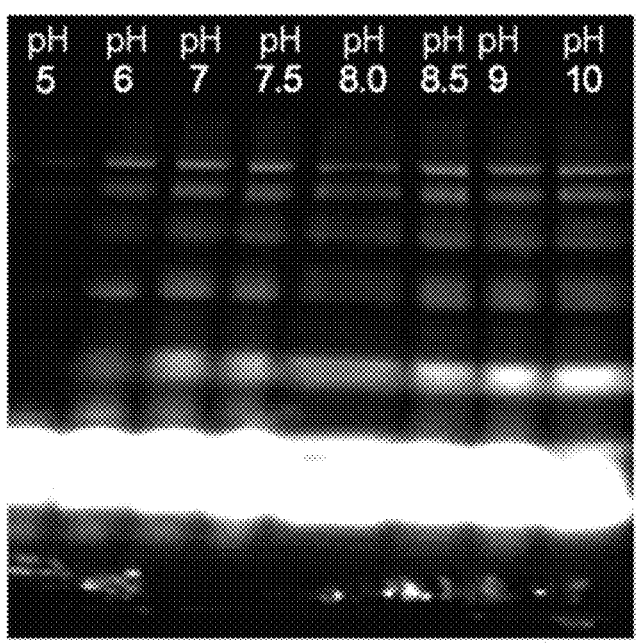
FIG. 3B is a fluorescence image of the proteins.

Gel electrophoresis was carried out in the same manner as in example 23, and an image observed by the naked eye (FIG. 3A) and a fluorescent image obtained using a Geliance 600 (FIG. 3B) are shown in FIG. 3. As can be seen from FIG. 3, proteins were stained very little at pH 5, whereas stained proteins were observed by both the naked eye and fluorescence analysis in the overall pH range and in particular, proteins which reacted with buffer solutions (pH 8.5 to 10) exhibited the strongest fluorescence.

Example 25

Protein Staining Test (3)

Each vial of one pack of Amershame™ HMW calibration kit (17-0445-01) for native electrophoresis (GE healthcare Co., Ltd.) contained five marker proteins (250 µg), that is, thyroglobulin (665 kD, 76 µg (30.4%)), ferritin (440 kD, 50 µg (20%), catalase (232 kD, 36 µg (14.4%), lactate dehydrogenase (140 kD, 48 µg (19.2%)), and bovine serum albumin (67 kD, 40 µg (16%)). The proteins were dissolved in 500 µl of water in each vial and filtered using VIVASPIN 500 (10 kD, Sartorius) and filtering was repeated several times with addition of water, to completely remove materials except the proteins. A 1 µl aliquot of the residue was placed in each of ten e-tubes.

Phosphate buffer solutions, carbonate buffer solutions and tris buffer solutions in concentrations of 0.1 M, 0.01 M and 0.001 M were prepared, a total of the 9 buffer solutions with various concentrations were added in an amount of 18 µl to the previously-prepared e-tubes, and the same volume of distilled water was added to the one remaining e-tube.

The compound 1-1 (1 mg) was dissolved in 100 µl of DMF, 1 µl of the solution was collected and added to the previously prepared 10 e-tubes, and the resulting mixtures were homogeneously mixed using a vortex shaker and centrifuge.

Figure 4A:
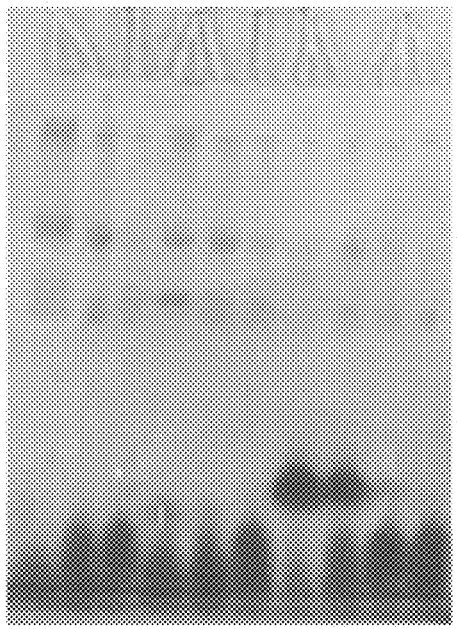
FIG. 4A is an image wherein proteins, which were labeled in Example 25 and subjected to development by gel electrophoresis, were observed by the naked eye.
Figure 4B:
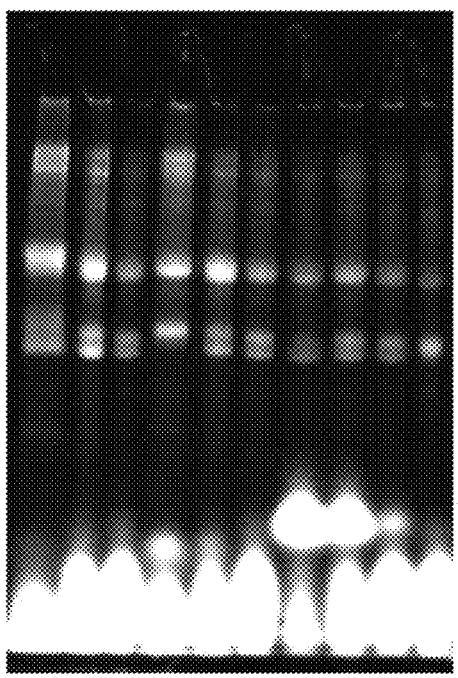
FIG. 4B is a fluorescence image of the proteins.

The e-tubes were added to the heating block set to 36.5° C. and the reaction was allowed to proceed for 4 hours. Gel electrophoresis was carried out in the same manner as in example 23. An image observed by the naked eye (FIG. 4A) and a fluorescence image obtained using a Geliance 600 (FIG. 4B) are shown in FIG. 4. Marker proteins (GE healthcare) used herein were developed for SDS-PAGE applications, but staining thereof may be confirmed, although they can be accurately separated depending on sizes. In each image, ten lanes, that is, 0.1 M, 0.01M, and 0.001M phosphate buffer solutions 0.1 M, 0.01M and 0.001M carbonate buffer solutions, and 0.1 M, 0.01M and 0.001M tris-buffer solutions are arranged from the left to the right in this order, and the rightmost lane is obtained by reaction in water. Proteins reacted in water are generally stained well and, from the fluorescence image, it can be seen that the 0.01M phosphate and carbonate buffer solutions exhibited the most efficient expression, in particular, and 0.01 M phosphate buffer solution exhibited the most superior fluorescence.

Comparative Test (1)

1 mg of Amershame™ Cy™5 Mono NHS Ester (PA15101, GE Cy5, GE healthcare) and 1 mg of the compound 1-2 were dissolved in 100 µl of DMF, and the solution was tested in the same manner as in example 22. GE Cy5 and the compound 1-2 have different molecular weights. For this reason, when the compound was aliquoted in an amount of 1 the amount of the GE dye corresponds to 0.01376 µmol, and the amount of the compound 1-2 corresponds to 0.01339 µmol. Dilutions of equivalent moles of benzyl amine, benzyl alcohol (molecular weight: 108.14, Aldrich) and benzyl mercaptan (molecular weight: 124.20, Aldrich) in 20 µl of DMF were prepared.

6 sets, each including 12 phosphate buffer solutions (0.1 M, 229 µl) having different pHs (i.e., pH 5, 6, 7, 7.5, 8, 8.5, 9, 9.5, 10, 11, 11.5 and 12) were prepared. One set included 1 µl of GE Cy5 dye solution and 20 µl of benzyl amine. In the same manner, the benzyl alcohol and benzyl mercaptan were mixed with the GE Cy5 dye solution. In the same manner, the solution of the compound 1-2 and three types of benzyl compounds were reacted with three sets of phosphate buffer solutions. 64 e-tubes thus prepared were reacted in a heating block at 36.5° C. for 4 hours.

Formula 14 below has a structure represented by the compound wherein the dye of GE Cy5 is bound to benzyl amine.

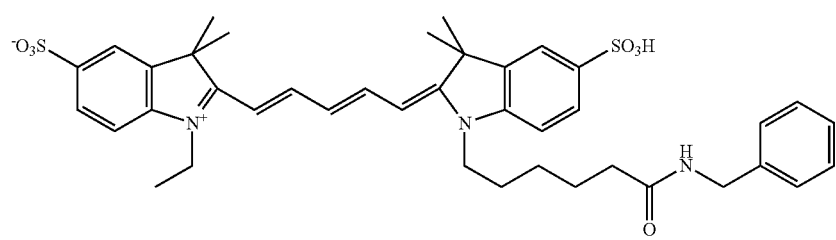

(14)

LC/MS, $C_{40}H_{46}N_3O_7S_2^-$, calculated value: 744.28, measured value: 744.37

Meanwhile, Formulae 15 to 17 below have structures represented by compounds wherein the compound 1-2 of the present invention is bound to benzyl amine, benzyl alcohol and benzyl mercaptan.

obtain a reaction yield. At this time, a 20% acetonitrile solution was used as a mobile phase, flow rate was 1 mL/min and analysis time was 30 minutes, and multi-scanning was carried out at wavelengths of 254, 365, 600, 650 and 700 nm.

Figure 5A:
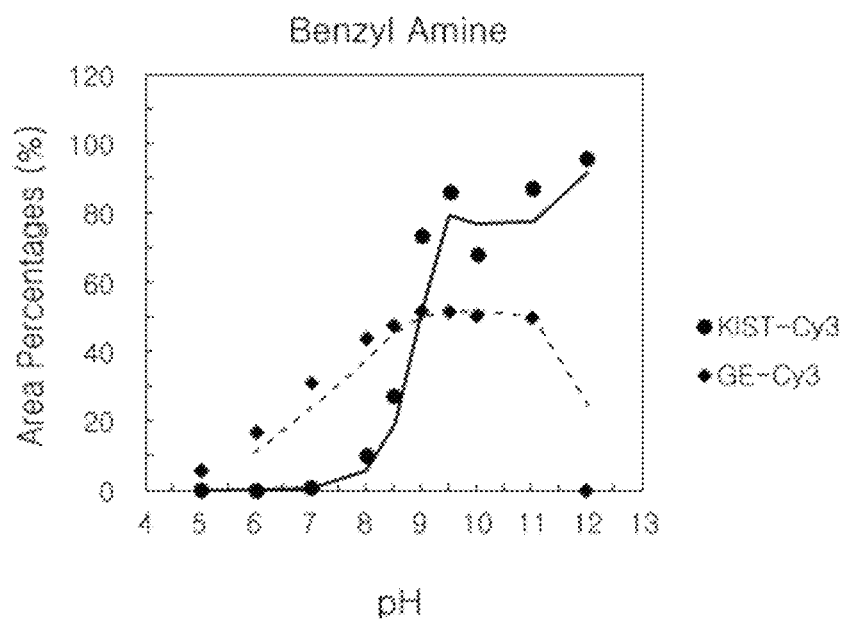
FIG. 5A illustrates absorbance (at 650 nm) of the reaction product obtained by reaction of benzyl amine with the GE Cy5 dye and the compound 1-2 in Comparative Test (1)
Figure 5B:
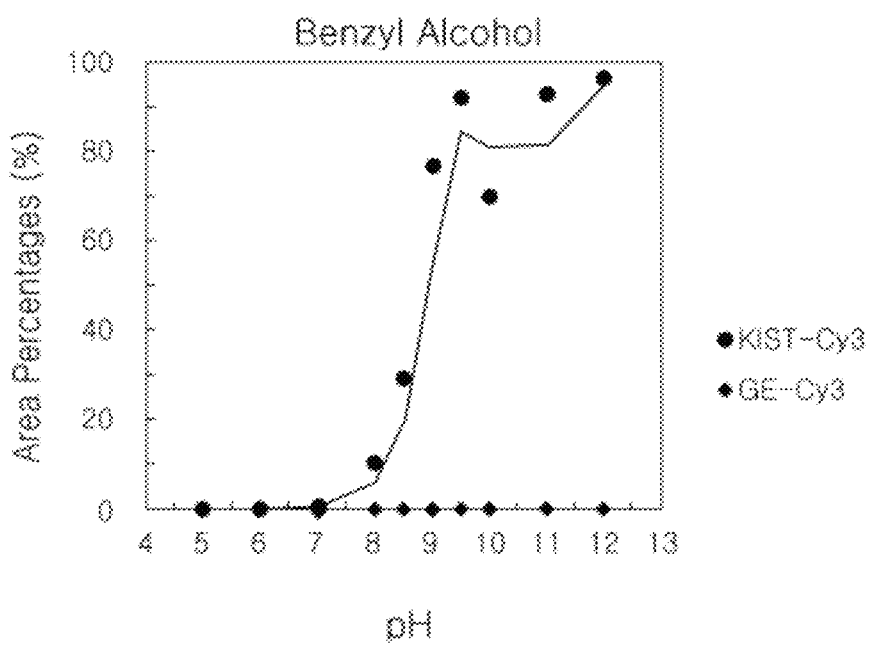
FIG. 5B shows absorbance (at 650 nm) of a reaction product of benzyl alcohol therewith.

The reaction yield, based on absorbance at a wavelength of 650 nm, is shown in FIGS. 5A to 5C.

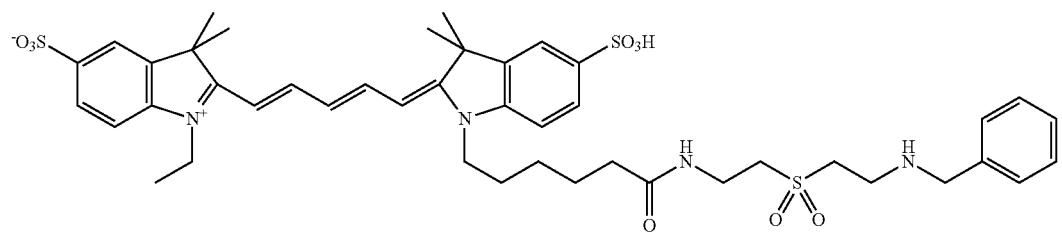

(15)

LC/MS, $C_{44}H_{55}N_4O_9S_3^-$, calculated value: 879.31, measured value: 879.57

As shown in 5A to 5C, the compound 1-2 of the present invention reacts with benzyl amine, benzyl alcohol and ben-

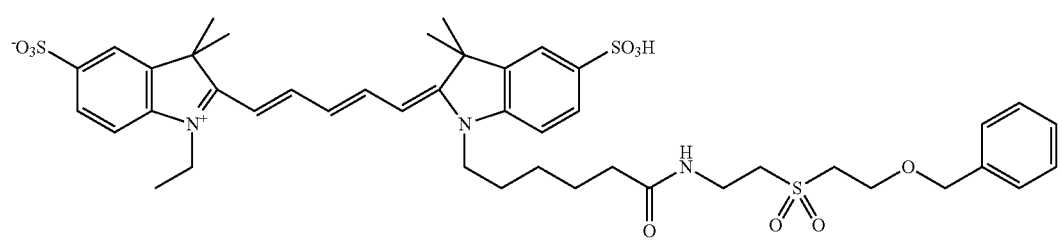

(16)

LC/MS, $C_{44}H_{54}N_3O_{10}S_3^-$, calculated value: 880.3, measured value: 880.53 zyl mercaptan at a high yield, in particular, exhibited a reaction yield of about 90% in the range of pH 9 to 11. GE Cy5 dye

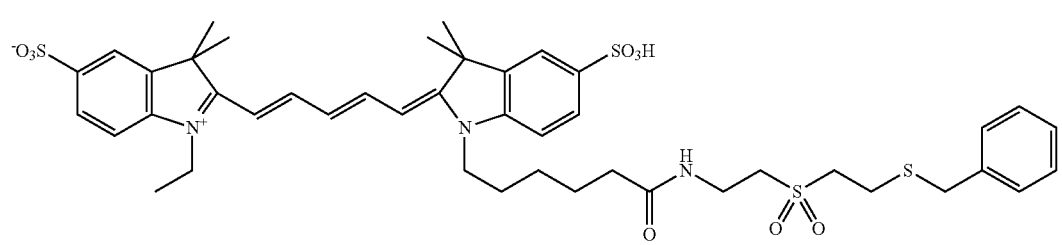

(17)

LC/MS, $C_{44}H_{55}N_3O_9S_4$, calculated value: 897.28, measured value: 897.03

Retention time (RT) of benzyl amine, the compound 1-16 and the product (compound 13) were confirmed by HPLC to reacts only with benzyl amine, to obtain a yield of 50% in the range of pH 9 to 11, whereas it does not react with benzyl alcohol or benzyl mercaptan. These results can be supported by the fact that, when the molecular weight was measured by LC/MS, the molecular weight of the structure wherein the dye of GE Cy5 is bound to benzyl alcohol or benzyl mercaptan was not obtained. These test results indicate that the compound of Formula 1 exhibits superior binding force to a compound containing amine, hydroxyl or thiol groups.

Comparative Test (2)

One tube containing protein molecular weight marker (Broad, Code No. 3452 available from Takara Bio Inc.) comprises proteins (18 μg/μl, total volume of 50 μl), a tris buffer solution, EDTA, NaCl and glycerol. The proteins include 9 kinds of proteins, namely, myosin (200 kD), β-galactosidase (116 kD), phosphorylase B (97.2 kD), serum albumin (66.4 kD), ovalbumin (44.3 kD), carbonic anhydrase (29 kD), a trypsin inhibitor (20.1 kD), lysozyme (14.3 kD) and aprotinin (6.5 kD). The protein aqueous solution (available from Takara Bio Inc.) was filtered using VIVASPIN 500 (5 kD, Sartorius), and a 1 μl aliquot of the resulting filtrate was placed in each of ten e-tubes.

18 μl of a phosphate buffer solution (pH 8.5 0.1 M) was placed in the previously prepared 10 e-tubes. For the five e-tubes, 1 mg of Amershame™ Cy™3 Mono NHS Ester available from GE healthcare (PA13101, hereinafter referred to as "GE Cy3") and 1 mg of the compound 1-1 were dissolved in 100 μl of DMF. The solution of GE Cy3 and the compound 1-1 were aliquoted in amounts of 0.25 μl, 0.125 μl, 0.0625 0.025 μl and 0.0025 and DMF was added to adjust the final volume of these solutions to 1 μl such that the volumes of these solutions were equivalent. The prepared 5 dye solutions were placed in the 10 e-tubes containing the previously prepared proteins, and the resulting mixture was homogeneously mixed using a vortex shaker and a centrifuge. Each e-tube was reacted in a heating block at 36.5° C. for 4 hours.

Figure 6A:
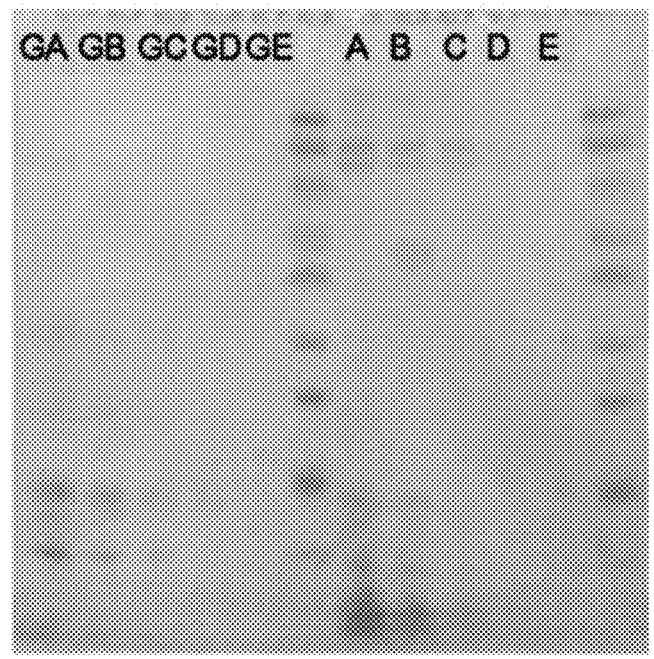
FIG. 6A is an image wherein proteins, which were labeled in Comparative Test (2) and subjected to development by gel electrophoresis, were observed by the naked eye.
Figure 6B:
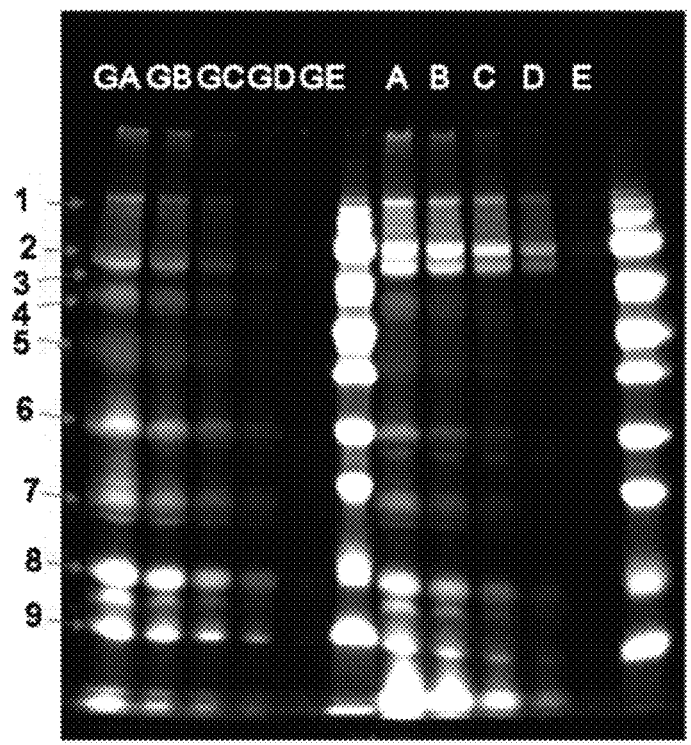
FIG. 6B is a fluorescence image of the proteins.
Figure 7A:
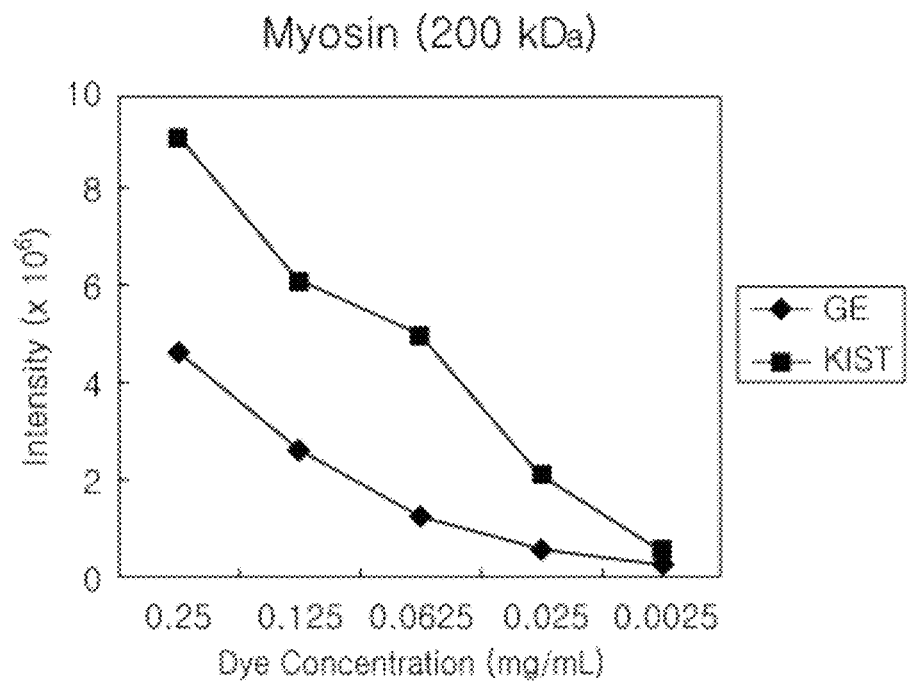
FIG. 7A illustrates fluorescence intensity of myosin labeled in Comparative Test (2) and developed by gel electrophoresis.
Figure 7B:
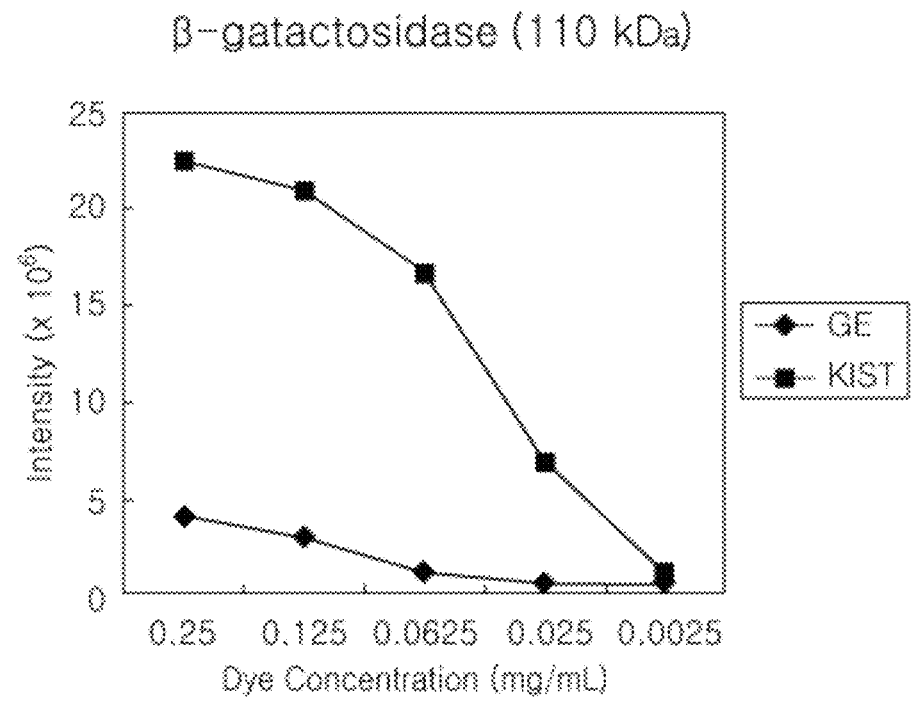
FIG. 7B illustrates fluorescence intensity of β-galactosidase.
Figure 7C:
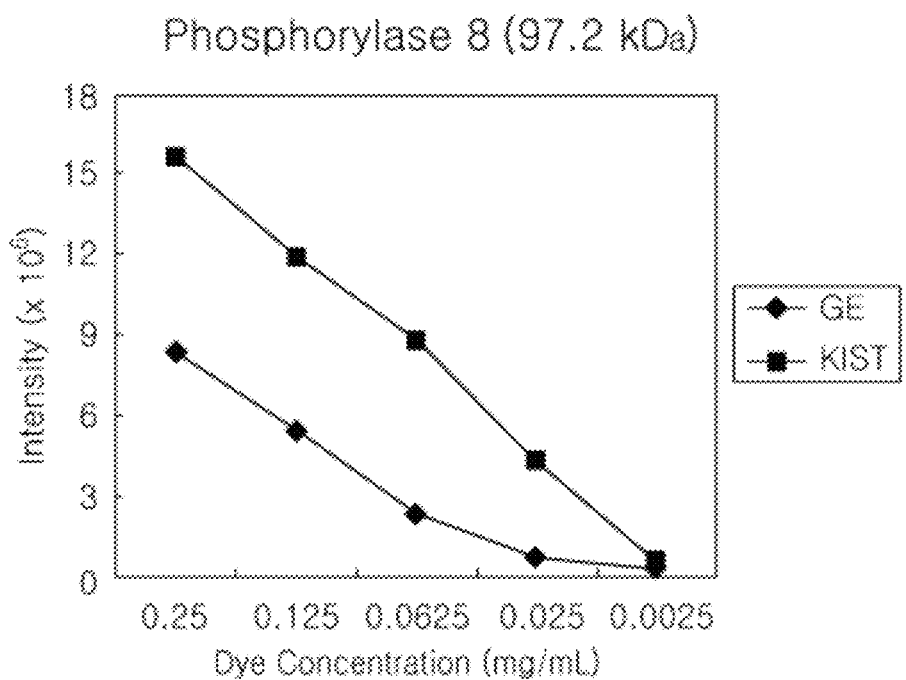
FIG. 7C illustrates fluorescence intensity of phosphorylase B.
Figure 7D:
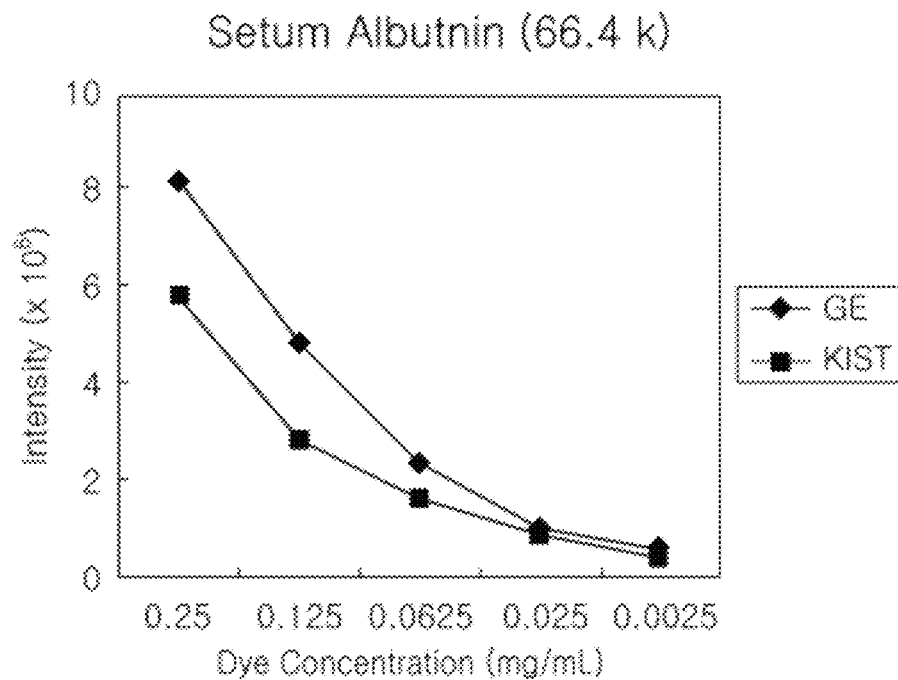
FIG. 7D illustrates fluorescence intensity of serum albumin.
Figure 7E:
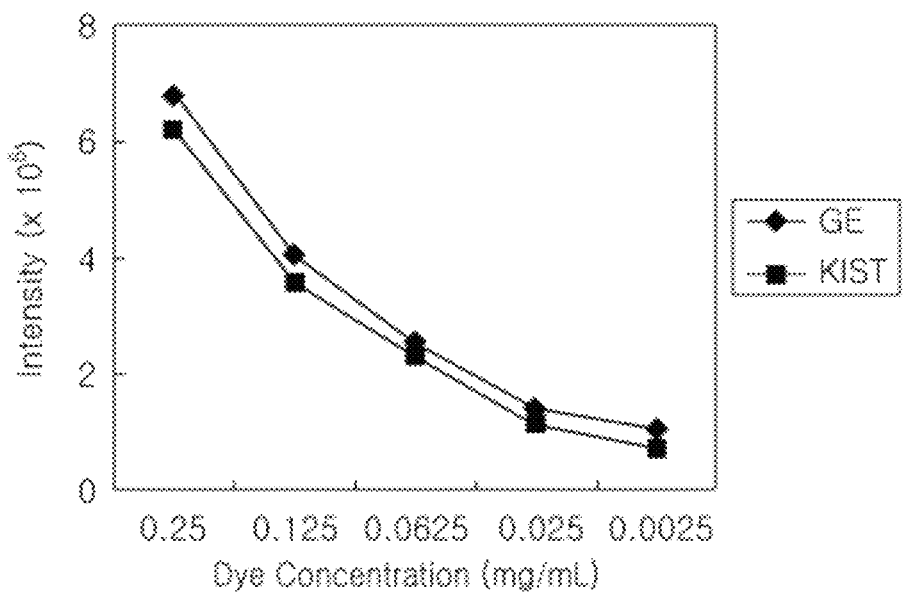
FIG. 7E illustrates fluorescence intensity of ovalbumin.
Figure 7F:
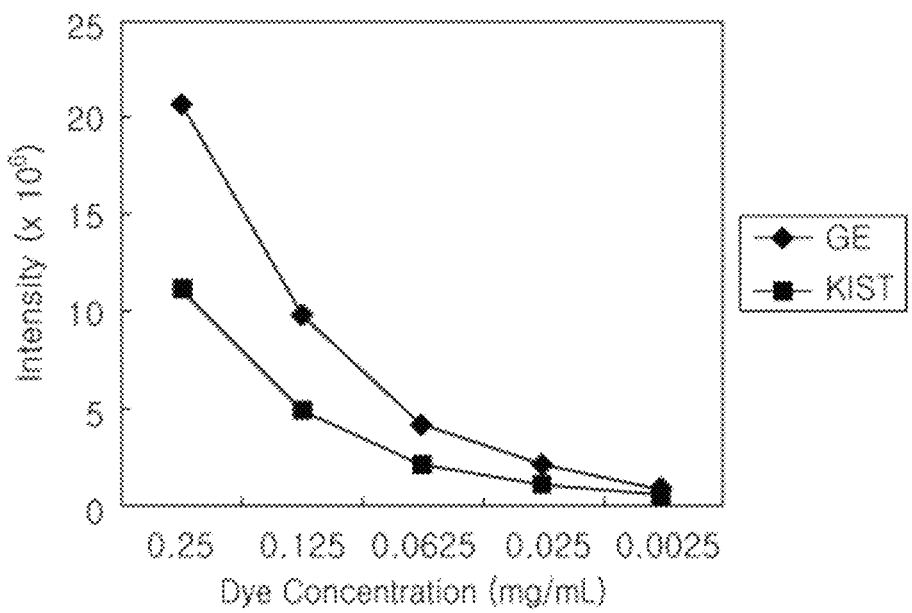
FIG. 7F illustrates fluorescence intensity of carbonic anhydrase.
Figure 7G:
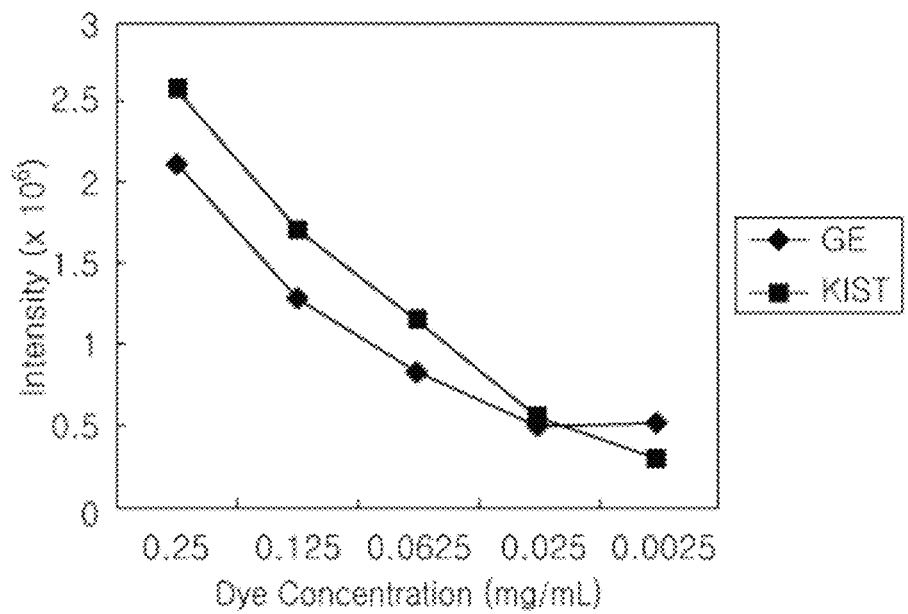
FIG. 7G illustrates fluorescence intensity of trypsin inhibitor.
Figure 7H:
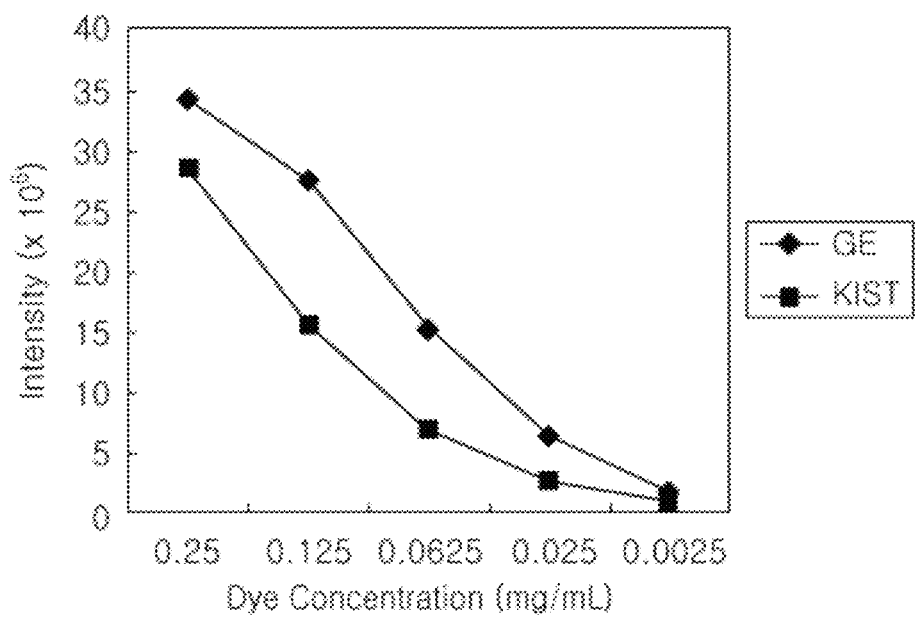
FIG. 7H illustrates fluorescence intensity of lysozyme.

Gel electrophoresis was carried out in the same manner as in Example 23, an image observed by the naked eye (FIG. 6A), and a fluorescence image obtained using a Geliance 600 (FIG. 6B) are shown in FIG. 6. In the images, references, GA to GE are obtained from the GE Cy3 dye, A to E are obtained from the compound 1-1 of the present invention, and $6^{th}$ to $12^{th}$ lanes of a gel image are color size markers. (Takara, Prosieve Color Protein Marker, Cat. No. 50550). As can be seen from FIG. 6, for the total 9 proteins, the compound 1-1 of the present invention exhibited color and fluorescence intensities, which can be identified by the naked eye, superior to or comparable to the GE Cy3 dye. In addition, the compound 1-1 exhibited more considerable fluorescence performance at low dye concentrations, as compared to the dye of GE.

For more detailed comparison, the fluorescence intensity program GelTools (ver.3.07.14) installed in the Geliance 600 apparatus was used to compare 9 proteins, and the results thus obtained are shown in FIGS. 7A to 7I. In FIGS. 7A to 7I, "GE" is obtained from the GE dye, and "KIST" is obtained from the compound 1-1. As shown in FIGS. 7A to 7I, the compound 1-1 exhibited superior fluorescence performance for all 9 proteins, as compared to the dye marker protein of GE. In particular, difference in fluorescence performance increases, as the molecular weight of the compound 1-1 increases to 50 kD or higher, which means that the compound of the present invention exhibits superior high-molecular compound staining performance.

Comparative Test (3)

Each tube of prosieve protein markers (Code No. 50547) available from Takara Bio Inc. contained proteins (at a concentration of 550 μg/500 μl, total volume of 500 μl), a tris-buffer solution, EDTA, NaCl and glycerol. Although the kinds of proteins contained in each prosieve protein marker are not mentioned in detail, 10 kinds of proteins having molecular weights of 225 kD, 150 kD, 100 kD, 75 kD, 50 kD, 35 kD, 25 kD, 15 kD, 10 kD and 5 kD, wherein the protein having a molecular weight of 50 kD is present in an amount of 100 μg and the remaining proteins were present in an amount of 50 μg, are known. This protein solution was filtered using a VIVASPIN 500 (10 kD, Sartorius) and the filtering was repeated several times with addition of 500 μl of water, to remove the materials except the proteins. A 2 μl aliquot of the residue was placed in each of 12 e-tubes.

1 mg of the product (dye available from GE health care) used in Comparative Example 2 (hereinafter, referred to as "GE Cy3"), 1 mg of the product used in Comparative Example 1 (hereinafter, referred to as "GE Cy5"), and 1 mg of the product, Amershame™ Cy™7 Mono NHS Ester (PA17101, hereinafter, referred to as "GE Cy7") were dissolved in 100 μl of DMF.

Meanwhile, 1 mg of the compounds 1-7, 1-1, 1-4, 1-10, 1-13, 1-19, 1-16, 1-2 and 1-3 was dissolved in 100 μl of DMF, to prepare a solution of compound 1-7 (hereinafter, referred to as "3-1"), a solution of the compound 1-1 (hereinafter, referred to as "3-2"), a solution of the compound 1-4 (hereinafter, referred to as "3-3"), a solution of the compound 1-10 (hereinafter, referred to as "3-4"), a solution of the compound 1-13 (hereinafter, referred to as "3-5"), a solution of the compound 1-19 (hereinafter, referred to as "3-6"), a solution of the compound I-16 (hereinafter, referred to as "3-7"), a solution of the compound 1-2 (hereinafter, referred to as "5-1") and a solution of the compound 1-3 (hereinafter, referred to as "7-1").

18 μl of a phosphate buffer solution (pH 9.5, 0.1 M) was placed in each of the previously prepared 12 e-tubes, 1 μl of GE Cy3, 3-1, 3-2, 3-3, 3-4, 3-5, 3-6, 3-7, GE Cy5, 5-1, GE Cy7 and 7-1 was placed in the respective e-tubes and the resulting solutions were homogeneously mixed using a vortex shaker and a centrifuge. The resulting mixture was reacted in a heating block at 36.5° C. for 6 hours.

Figure 8A:
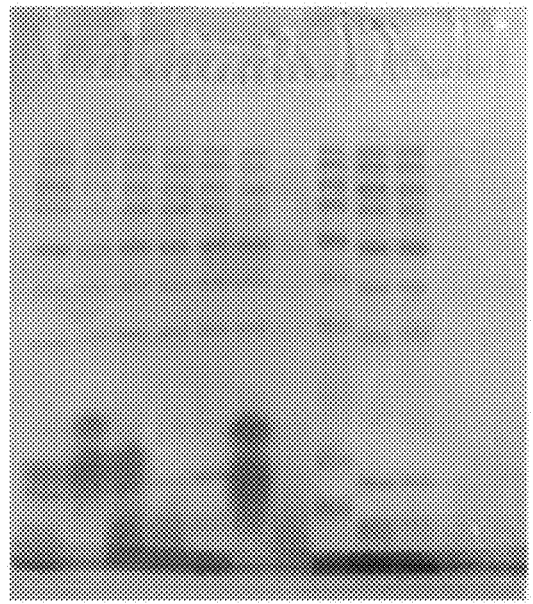
FIG. 8A is an image wherein proteins, which were labeled in Comparative Test (3) and subjected to development by gel electrophoresis, were observed by the naked eye.
Figure 8B:
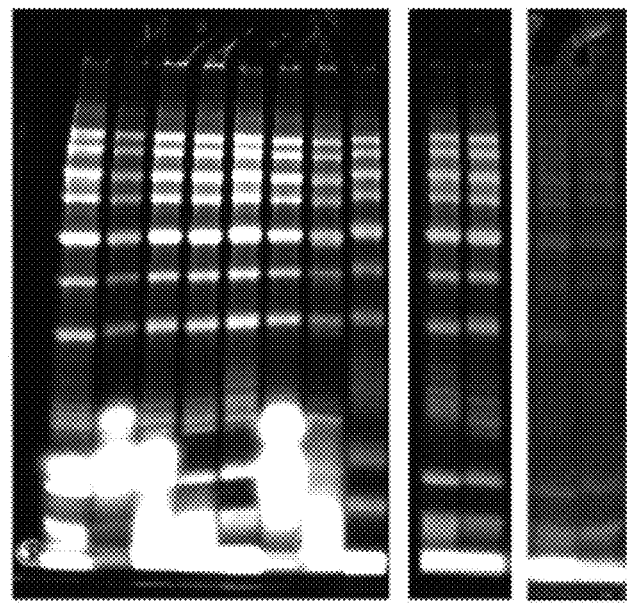
FIG. 8B is a fluorescence image of the proteins.

Gel electrophoresis was carried out as in Example 23 and an image observed by the naked eye (FIG. 8A), and a fluorescence image measured using a Geliance 600 (FIG. 8B) are shown in FIG. 8. FIGS. 8A and 8B show color and fluorescence of GE Cy3-, 3-1-, 3-2-, 3-3-, 3-4-, 3-5-, 3-6-, 3-7-, GE Cy5-, 5-1-, GE Cy7- and 7-1-marked proteins from left to right, respectively. 3-2, 3-3 and 3-4 expressed considerably superior fluorescence, which means that proteins were marked with a larger amount of dye, as compared to GE Cy3. GE Cy5 and 5-1 exhibited substantially identical fluorescence, GE Cy7 and 7-1 had absorbance or fluorescence wavelengths in the range of near infrared rays, and thus cannot be observed by the naked eye, but exhibit substantially identical fluorescence performance.

As apparent from the afore-going, the present invention enables biomolecular researchers to handle dyes more stably, when performing labeling tests. In particular, binding of biomolecules to dyes does not cause by-products, thus eliminating the necessity of additional purification processes. In addition, the compound of the present invention enables easy long-term storage due to superior stability and is more applicable to users who stain large molecular-weight biomolecules for a long period and handle more complicated biomolecules.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A cyanine compound represented by Formula 1 below:

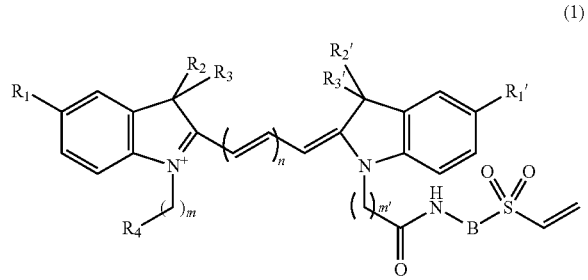
(1)

wherein $R_1$ and $R_1'$ are each independently hydrogen, a sulfonic acid group or a sulfonic acid base;

$R_2$, $R_2'$, $R_3$ and $R_3'$ are each independently hydrogen or a $C_1$-$C_6$ alkyl group;

$R_4$ is hydrogen, a $C_1$-$C_6$ alkyl group, a carboxyl group, —CONH(CH$_2$)$_L$SO$_2$CH=CH$_2$, —CONH-para-(C$_6$H$_4$)SO$_2$CH=CH$_2$ or —CONH-meta-(C$_6$H$_4$)SO$_2$CH=CH$_2$;

B is (CH$_2$)$_l$, para-(C$_6$H$_4$) or meta-(C$_6$H$_4$);

m and m' are each independently an integer of 1 to 5; and

L, l and n are each independently an integer of 1 to 5.

2. The compound according to claim 1, wherein the compound is selected from the group consisting of:

1-1
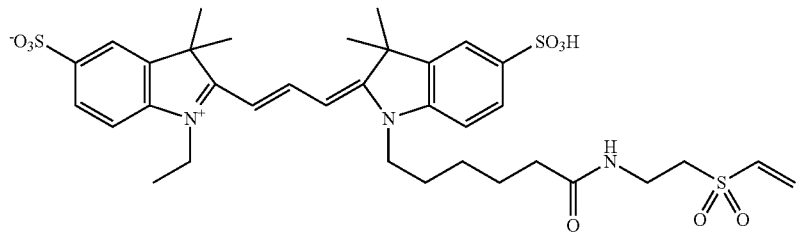

1-2
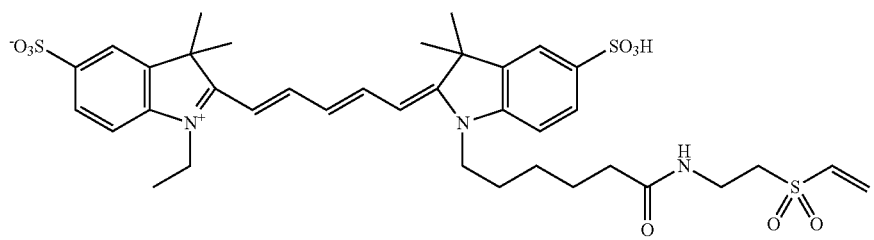

1-3
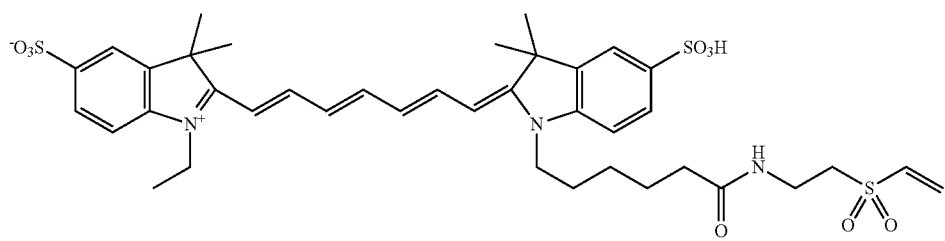

1-4
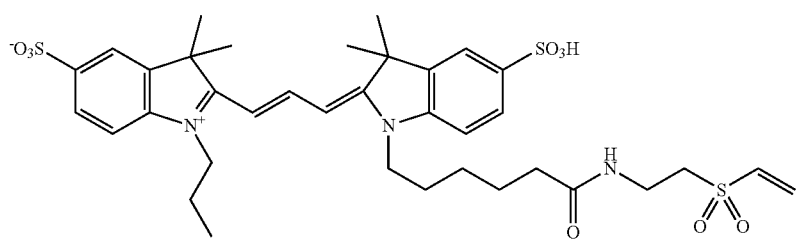

1-5
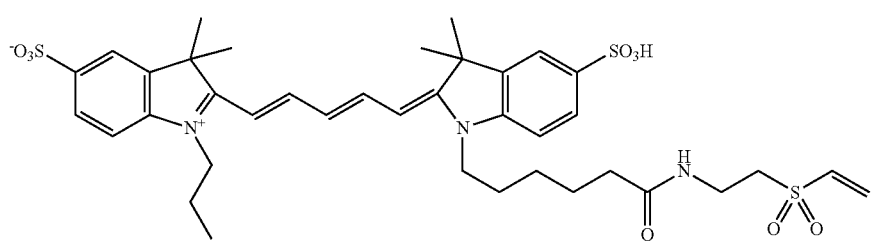

1-6
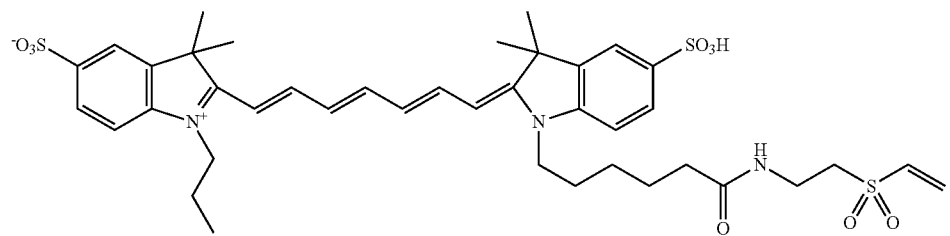
1-7
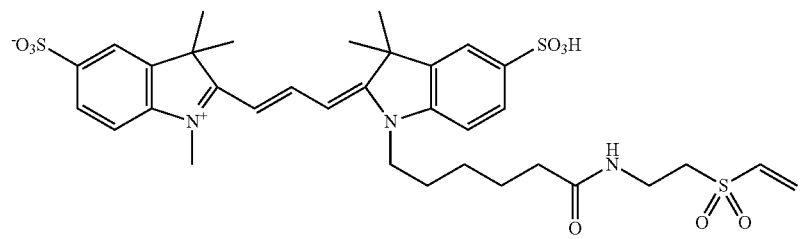
1-8
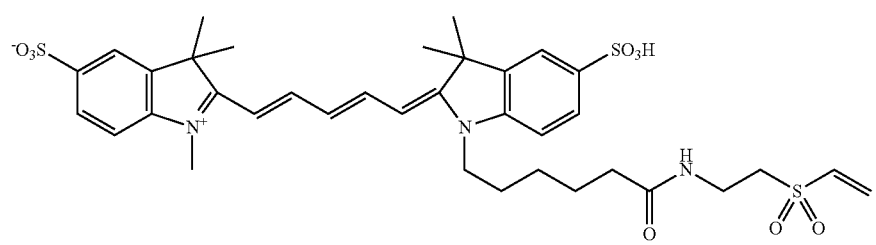
1-9
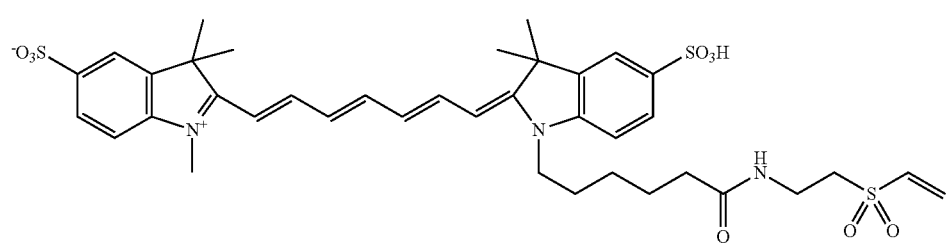
1-10
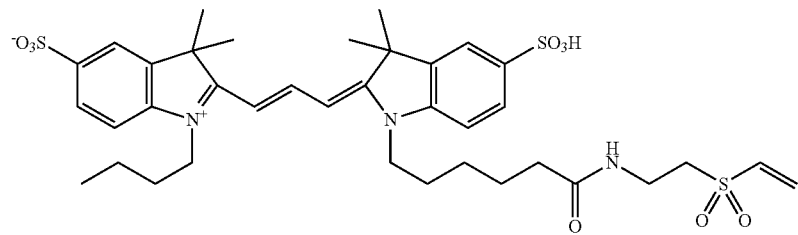
1-11
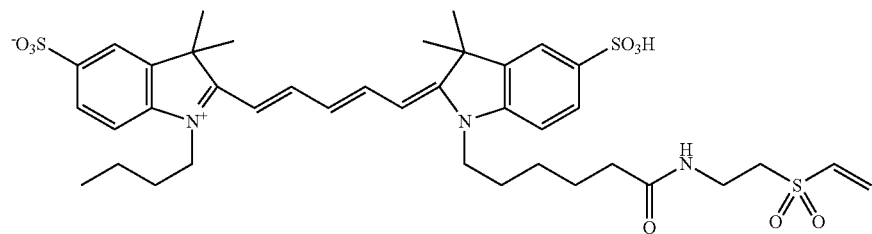

1-12
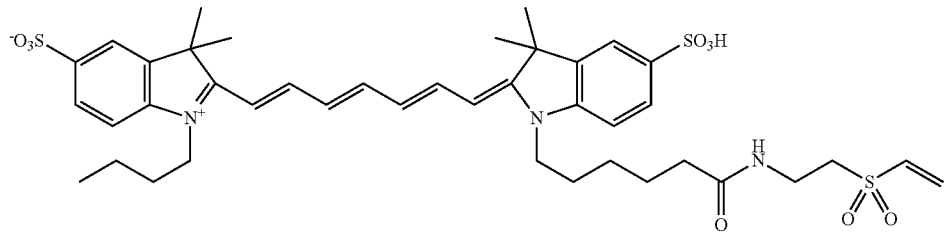
1-13
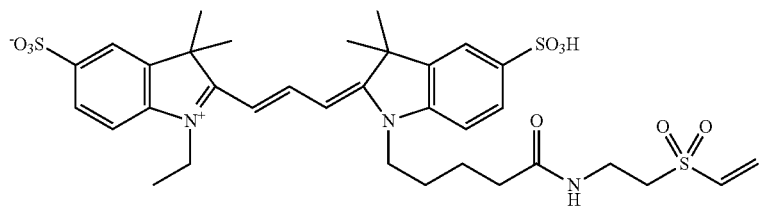
1-14
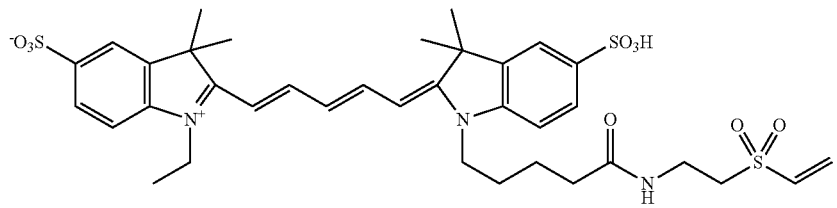
1-15
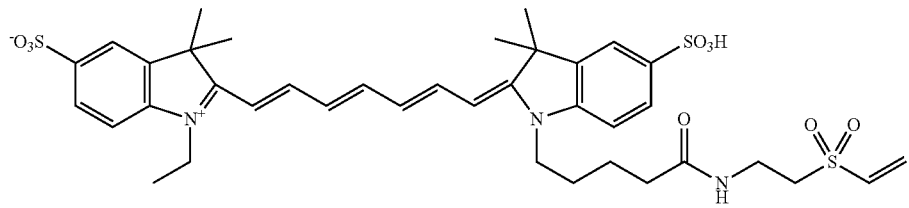
1-16
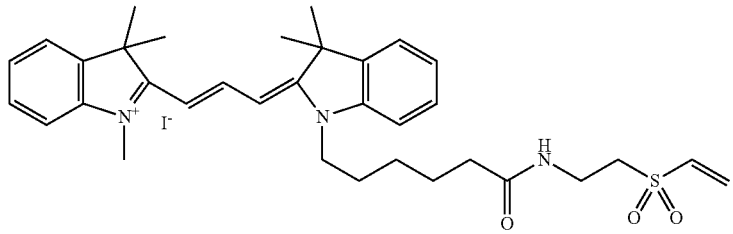
1-17
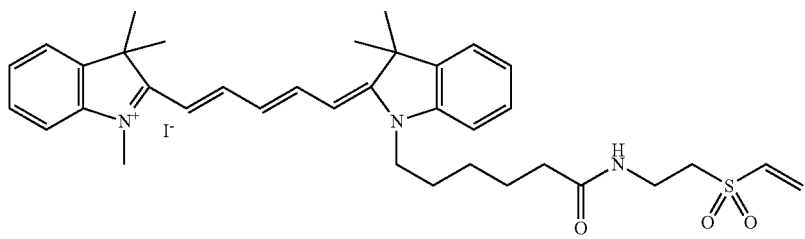

1-18

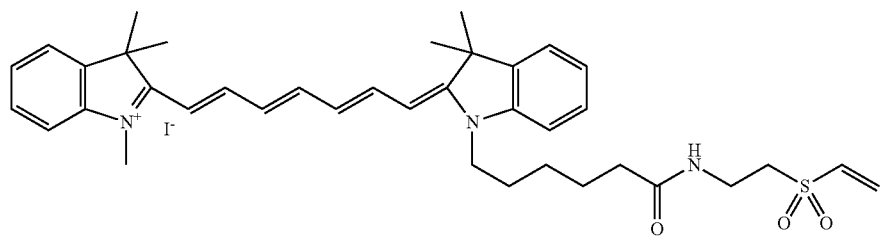

1-19

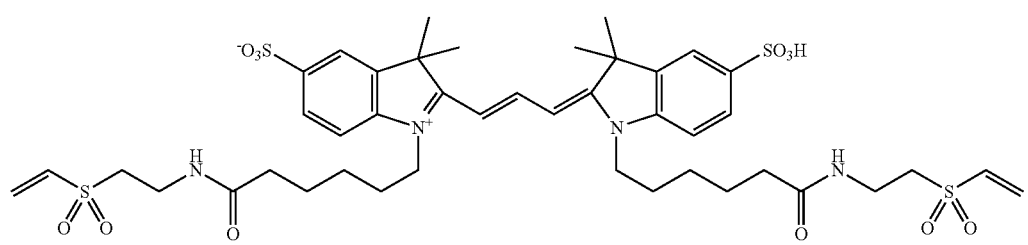

1-20

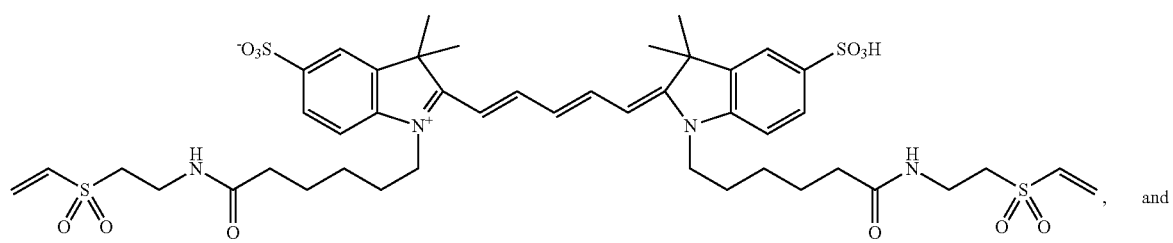, and 1-21

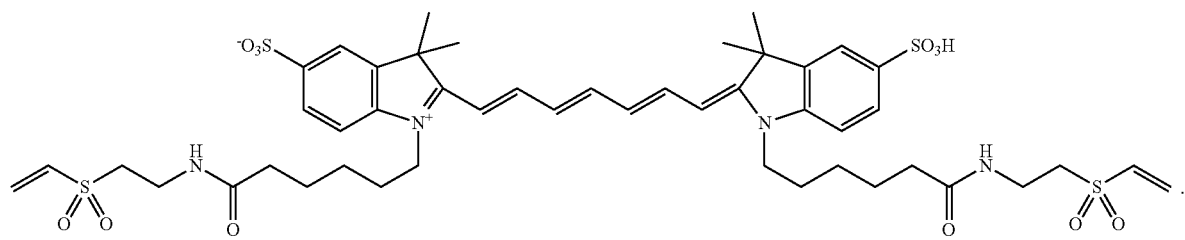.

3. The compound according to claim 1, wherein the compound fluoresces at a wavelength of 500 to 800 nm.

4. A method for labeling biomolecules, nanoparticles, or organic compounds containing an amine group, a hydroxyl group or a thiol group with the compound of Formula 1 according to claim 1,
wherein the labeling is carried out by binding vinyl sulfone present in the compound of Formula 1 to the amine, hydroxyl or thiol group present in the biomolecules, nanoparticles or organic compounds through reaction of the vinyl sulfone with the amine, hydroxyl or thiol group.

5. The method according to claim 4, wherein the biomolecule is selected from the group consisting of proteins, peptides, carbohydrates, sugars, lipids, antibodies, proteoglycans, glycoproteins and siRNA.

6. The method according to claim 4, wherein the solvent for labeling is selected from the group consisting of (i) a buffer solution selected from the group consisting of a phosphate buffer solution, (ii) a carbonate buffer solution and a tris buffer solution, an organic solvent selected from the group consisting of dimethyl sulfoxide, dimethyl formamide, methanol, ethanol and acetonitrile, and (iii) water.

7. The method according to claim 4, wherein the labeling is carried out at pH 5 to 12.

8. The method according to claim 4, wherein the labeling is carried out by reacting the compound of Formula 1 with biomolecules, nanoparticles or organic compounds at a temperature of 20 to 80° C. for 30 minutes to 48 hours.

9. A material selected from biomolecules, nanoparticles and organic compounds labeled with the compound of Formula 1 according to claim 1.

10. The material according to claim 9, wherein the biomolecule is selected from the group consisting of proteins, peptides, carbohydrates, sugars, lipids, antibodies, proteoglycans, glycoproteins and siRNA.

11. A method for preparing a compound of Formula 1, comprising:

reacting a compound of Formula 4 with a compound of Formula 5 or 7, to obtain a compound of Formula 6a;

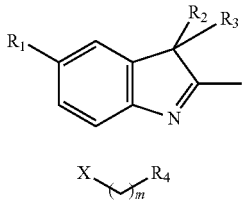
(4)

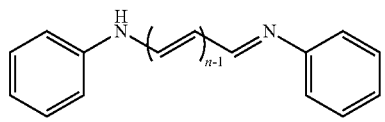
(5)

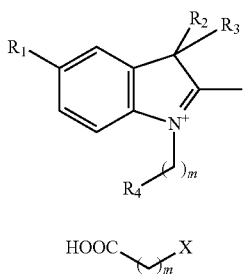
(6a)

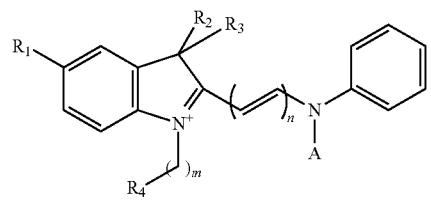
(7)

reacting the compound of Formula 6a with a compound of Formula 8 to obtain a compound of Formula 9;

(8)

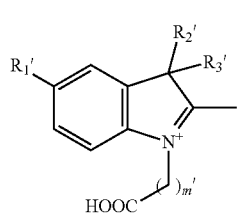
(9)

reacting the compound of Formula 9 with a compound of Formula 6b to obtain a compound represented by Formula 10;

(6b)

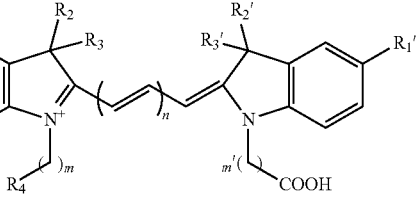
(10)

reacting the compound of Formula 10 with 1,1'-carbonyl diimidazole or N,N-disuccinimidyl carbonate to obtain a compound of Formula 11a or 11b; and

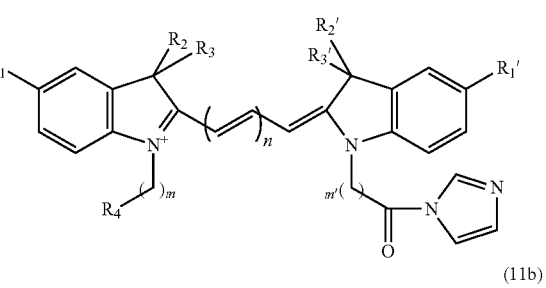
(11a)

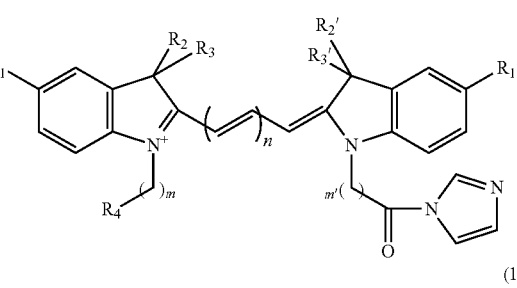
(11b)

reacting the compound of Formula 11a or 11b with a compound represented by Formula 12 in the presence of a Hunig's base to obtain the compound of Formula 1;

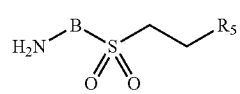
(12)

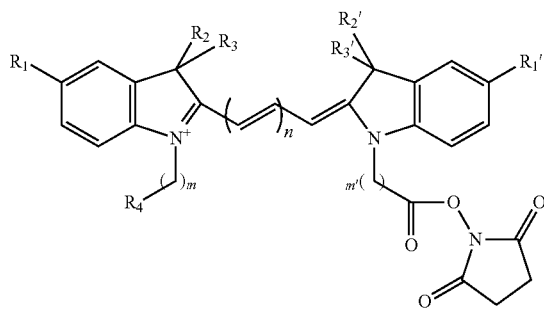
(1)

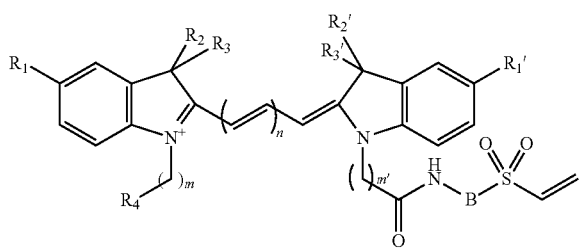

wherein
$R_1$ and $R_1'$ are each independently hydrogen, a sulfonic acid group or a sulfonic acid base;
$R_2$, $R_2'$, $R_3$ and $R_3'$ are each independently hydrogen or a $C_1$-$C_6$ alkyl group;

$R_4$ is hydrogen, a $C_1$-$C_6$ alkyl group, a carboxyl group, —CONH$(CH_2)_L$SO$_2$CH=CH$_2$, —CONH-para-$(C_6H_4)$SO$_2$CH=CH$_2$ or —CONH-Meta-$(C_6H_4)$SO$_2$CH=CH$_2$;

$R_5$ is a halogen atom selected from the group consisting of fluorine, chlorine, bromine and iodine, or a sulfato group (—OSO$_3$H);

A is hydrogen or an acetyl group;

B is $(CH_2)_l$, para-$(C_6H_4)$ or meta-$(C_6H_4)$;

X is a halogen atom selected from the group consisting of fluorine, chlorine, bromine and iodine;

m and m' are each independently an integer of 1 to 5; and

L, l and n are each independently an integer of 1 to 5.

* * * * *

UNITED STATES PATENT AND TRADEMARK OFFICE
CERTIFICATE OF CORRECTION

PATENT NO. : 8,729,276 B2
APPLICATION NO. : 13/264258
DATED : May 20, 2014
INVENTOR(S) : Kim et al.

It is certified that error appears in the above-identified patent and that said Letters Patent is hereby corrected as shown below:

In the Claims

Column 62,
Lines 8 and 9, "CONH-para-$(C_6H_4)SO_2CH=CH_2$" should read --CONH-*para*-$(C_6H_4)SO_2CH=CH_2$--;
Lines 9 and 10, "CONH-meta-$(C_6H_4)SO_2CH=CH_2$" should read --CONH-*meta*-$(C_6H_4)SO_2CH=CH_2$--;
Line 11, "$(CH_2)_l$, para-$(C_6H_4)$ or meta-$(C_6H_4)$" should read --$(CH_2)_l$, *para*-$(C_6H_4)$ or *meta*-$(C_6H_4)$--.

Column 71,
Lines 2 and 3, "CONH-para-$(C_6H_4)SO_2CH=CH_2$" should read --CONH-*para*-$(C_6H_4)SO_2CH=CH_2$--;
Lines 3 and 4, "CONH-Meta-$(C_6H_4)SO_2CH=CH_2$" should read --CONH-*meta*-$(C_6H_4)SO_2CH=CH_2$--;
Line 9, "$(CH_2)_l$, para-$(C_6H_4)$ or meta-$(C_6H_4)$" should read --$(CH_2)_l$, *para*-$(C_6H_4)$ or *meta*-$(C_6H_4)$--.

Signed and Sealed this
Twenty-sixth Day of August, 2014

Michelle K. Lee
*Deputy Director of the United States Patent and Trademark Office*